(12) United States Patent
Yamazaki et al.

(10) Patent No.: US 11,888,122 B2
(45) Date of Patent: Jan. 30, 2024

(54) ELECTROLYTE SOLUTION, ELECTROCHEMICAL DEVICE, LITHIUM ION SECONDARY BATTERY AND MODULE

(71) Applicant: DAIKIN INDUSTRIES, LTD., Osaka (JP)

(72) Inventors: Shigeaki Yamazaki, Osaka (JP); Hiroyuki Arima, Osaka (JP); Kenzou Takahashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/950,036

(22) Filed: Sep. 21, 2022

(65) Prior Publication Data
US 2023/0102163 A1 Mar. 30, 2023

Related U.S. Application Data

(63) Continuation of application No. 16/497,559, filed as application No. PCT/JP2018/002421 on Jan. 26, 2018, now Pat. No. 11,489,204.

(30) Foreign Application Priority Data

Mar. 31, 2017 (JP) ................. 2017-073088

(51) Int. Cl.
| | |
|---|---|
| H01M 10/0569 | (2010.01) |
| C07C 69/63 | (2006.01) |
| C07C 69/96 | (2006.01) |
| C07D 317/38 | (2006.01) |
| H01G 11/60 | (2013.01) |
| H01M 10/0525 | (2010.01) |

(52) U.S. Cl.
CPC ......... *H01M 10/0569* (2013.01); *C07C 69/63* (2013.01); *C07C 69/96* (2013.01); *C07D 317/38* (2013.01); *H01G 11/60* (2013.01); *H01M 10/0525* (2013.01); *H01M 2300/0037* (2013.01)

(58) Field of Classification Search
CPC ..... H01M 10/0568; C07C 69/63; C07C 69/96
See application file for complete search history.

(56) References Cited

U.S. PATENT DOCUMENTS

| | | | |
|---|---|---|---|
| 2010/0062344 A1 | 3/2010 | Koh et al. | |
| 2010/0081063 A1* | 4/2010 | Yamamoto .......... | H01M 10/052 429/338 |
| 2010/0310943 A1 | 12/2010 | Koh et al. | |
| 2011/0159382 A1 | 6/2011 | Mstsui et al. | |
| 2013/0252113 A1 | 9/2013 | Yu et al. | |
| 2015/0072248 A1 | 3/2015 | Watanabe et al. | |
| 2015/0086877 A1 | 3/2015 | Yamazaki et al. | |
| 2015/0118576 A1 | 4/2015 | Chiga et al. | |
| 2017/0077552 A1 | 3/2017 | Taeda et al. | |
| 2017/0200974 A1 | 7/2017 | Maruo et al. | |
| 2017/0346071 A1 | 11/2017 | Ogata et al. | |
| 2018/0090790 A1 | 3/2018 | Nakatsutsumi et al. | |
| 2020/0020982 A1 | 1/2020 | Yamazaki et al. | |
| 2020/0036043 A1 | 1/2020 | Ishikawa et al. | |

FOREIGN PATENT DOCUMENTS

| | | |
|---|---|---|
| EP | 0 806 804 A1 | 11/1997 |
| EP | 3 070 778 A1 | 9/2016 |
| JP | 2006-294403 A | 10/2006 |
| JP | 2006-338892 A | 12/2006 |
| JP | 2008-123714 A | 5/2008 |

(Continued)

OTHER PUBLICATIONS

Communication dated Dec. 2, 2020, from the European Patent Office in European Application No. 18778039.0.
Communication dated Mar. 15, 2021, from the European Patent Office in application No. 18778039.0.
International Preliminary Report on Patentability dated Oct. 1, 2019 and translation of the Written Opinion from the International Bureau in counterpart International Application No. PCT/JP2018/002421.
International Search Report for PCT/JP2018/002421 dated Apr. 17, 2018 [PCT/ISA/210].

*Primary Examiner* — Amanda C. Walke
(74) *Attorney, Agent, or Firm* — Sughrue Mion, PLLC

(57) ABSTRACT

An electrolyte solution including a solvent, the solvent containing a compound (1a) represented by the following formula (1a); and

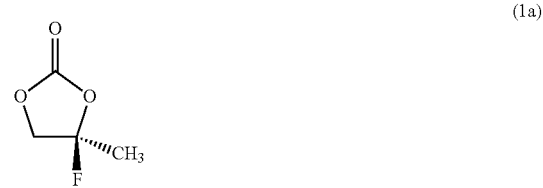

a compound (2) represented by the following formula (2):

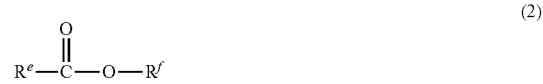

wherein $R^e$ is a C1-C5 linear or branched alkyl group optionally containing an ether bond; $R^f$ is a C1-C5 linear or branched alkyl group optionally containing an ether bond; and at least one of $R^e$ or $R^f$ contains a fluorine atom. Also disclosed is an electrochemical device including the electrolyte solution, a lithium-ion secondary battery including the electrolyte solution, and a module including the electrochemical device or the lithium-ion secondary battery.

8 Claims, No Drawings

(56) References Cited

FOREIGN PATENT DOCUMENTS

| | | | |
|---|---|---|---|
| JP | 2008-257988 A | | 10/2008 |
| JP | 2009-086582 A | | 4/2009 |
| JP | 2009-206072 A | | 9/2009 |
| JP | 4392726 B2 | | 1/2010 |
| JP | 2010024216 A | * | 2/2010 |
| JP | 2010-126477 A | | 6/2010 |
| JP | 20100310943 A1 | | 12/2010 |
| JP | 2017004690 A | | 5/2017 |
| WO | 2010/128584 A1 | | 11/2010 |
| WO | 2013/157503 A1 | | 10/2013 |
| WO | 2016/009923 A1 | | 1/2016 |
| WO | 2016/151983 A1 | | 9/2016 |
| WO | 2017/047020 A1 | | 3/2017 |

* cited by examiner

ELECTROLYTE SOLUTION, ELECTROCHEMICAL DEVICE, LITHIUM ION SECONDARY BATTERY AND MODULE

CROSS-REFERENCE TO RELATED APPLICATIONS

This application is a Rule 53(b) Continuation of U.S. application Ser. No. 16/497,559 filed Sep. 25, 2019, which is a National Stage of International Application No. PCT/JP2018/002421 filed Jan. 26, 2018, claiming priority based on Japanese Patent Application No. 2017-073088 filed Mar. 31, 2017. The respective disclosures of the above-identified applications are incorporated herein by reference in their entirety.

TECHNICAL FIELD

The invention relates to electrolyte solutions, electrochemical devices, lithium-ion secondary batteries, and modules.

BACKGROUND ART

Current electric appliances demonstrate a tendency to have a reduced weight and a smaller size, which leads to development of electrochemical devices such as lithium-ion secondary batteries having a high energy density. Further, electrochemical devices such as lithium-ion secondary batteries are desired to have improved characteristics as they are applied to more various fields. Improvement in battery characteristics will become more and more important particularly when lithium-ion secondary batteries are put in use for automobiles.

For example, Patent Literature 1 discloses an electrolyte solution containing a solvent and an electrolyte salt, the solvent containing a cyclic carbonate ester represented by the following formula:

[Chem. 1]

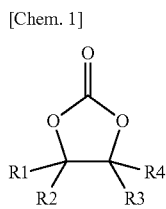

(wherein R1 to R4 are each a hydrogen group, a fluorine group, an alkyl group, or a fluorinated alkyl group, they are the same as or different from each other, and at least one of them is a fluorine group or a fluorinated alkyl group) and an acyclic carbonate ester represented by the following formula:

[Chem. 2]

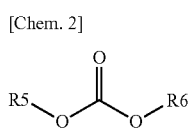

(wherein R5 and R6 are each a hydrogen group, a fluorine group, an alkyl group, or a fluorinated alkyl group, they are the same as or different from each other, and at least one of them is a fluorine group or a fluorinated alkyl group).

Patent Literature 2 discloses a nonaqueous electrolyte solution containing: a solvent (I) for dissolving an electrolyte salt that contains a fluorine-containing ester solvent (A) represented by the following formula:

(wherein $R^1$ is a hydrogen atom, a fluorine atom, or a C1-C3 alkyl group in which a hydrogen atom is optionally replaced by a fluorine atom; X is a hydrogen atom or a fluorine atom; when $R^1$ is a fluorine atom or a perfluoroalkyl group, X is a hydrogen atom; and $R^2$ is a C1-C4 alkyl group) and a fluorine-containing solvent (B) other than the fluorine-containing ester solvent (A); and an electrolyte salt (II).

Patent Literature 3 discloses an electrolyte solution containing a solvent and an electrolyte salt, the solvent containing a fluorine-containing compound represented by any of the following formulae:

wherein $Rf^1$ is a C1-C4 fluorine-containing alkyl group; and R is a C1-C4 non-fluorinated alkyl group; and

wherein $Rf^2$ and $Rf^3$ are the same as or different from each other, and are each a C1-C4 fluorine-containing alkyl group.

Patent Literature 4 discloses a non-aqueous electrolyte solution containing: [A] a non-aqueous solvent that contains a fluorinate carbonate, a cyclic carbonate, and an acyclic carbonate, with (i) the cyclic carbonate being contained in an amount of 2 to 63 mol %, (ii) the acyclic carbonate being contained in an amount of 2 to 63 mol %, and (iii) the fluorinated carbonate being contained in an amount of 60 to 96 mol % (the sum of (i) to (iii) being smaller than 100 mol %), the fluorinated carbonate being represented by the following formula [1]:

[Chem. 3]

[1]

(wherein $R^1$ and $R^2$ are the same as or different from each other; one of them is a C1-C4 hydrocarbon group in which one or more hydrogen atoms being replaced by fluorine atoms, and the other is a C1-C4 hydrocarbon group or a 1-4 hydrocarbon group in which one or more hydrogen atoms being replaced by fluorine atoms, with such hydrocarbon groups including groups containing a hetero atom such as oxygen or nitrogen); and [B] an electrolyte.

CITATION LIST

Patent Literature

Patent Literature 1: JP 2008-123714 A
Patent Literature 2: JP 2008-257988 A
Patent Literature 3: WO 2013/157503
Patent Literature 4: JP 4392726 B

SUMMARY OF INVENTION

Technical Problem

Conventional electrolyte solutions containing a fluorine-based solvent give excellent battery cycle characteristics, but tend to give a higher resistance than electrolyte solutions containing non-fluorine-based solvent. Those capable of reducing generation of gas during cycles are awaited.

The invention is made in view of the above state of the art, and aims to provide an electrolyte solution that can give a low resistance to an electrochemical device while maintaining the cycle characteristics of the electrochemical device and can reduce generation of gas during cycles although the electrolyte solution contains a fluorine-based solvent, and an electrochemical device containing the electrolyte solution.

Solution to Problem

The inventors found that an electrolyte solution containing a fluorinated cyclic carbonate having a specific structure and a fluorinated acyclic ester or carbonate having a specific structure can give a low resistance to an electrochemical device while maintaining the cycle characteristics of the electrochemical device and can reduce generation of gas during cycles although the electrolyte solution contains a fluorine-based solvent.

Specifically, the invention relates to an electrolyte solution containing a solvent, the solvent containing: a compound (1) represented by the following formula (1):

[Chem. 4]

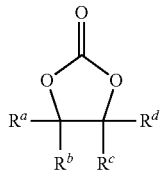

(1)

(wherein $R^a$, $R^b$, $R^c$, and $R^d$ are the same as or different from each other, and are each —H, —F, —$CH_3$, or —$CF_3$; at least one of $R^a$, $R^b$, $R^c$, or $R^d$ is F or —$CF_3$; and at least one of $R^a$, $R^b$, $R^c$, or $R^d$ is —$CH_3$); and a compound (2) represented by the following formula (2):

[Chem. 5]

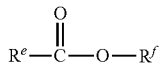

(2)

(wherein $R^e$ is a C1-05 linear or branched alkyl or alkoxy group optionally containing an ether bond; $R^f$ is a C1-05 linear or branched alkyl group optionally containing an ether bond; and at least one of $R^e$ or $R^f$ contains a fluorine atom).

In the electrolyte solution of the invention, the compound (1) is preferably contained in an amount of 0.001 to 99.999% by volume relative to the solvent and the compound (2) is preferably contained in an amount of 0.001 to 99.999% by volume relative to the solvent.

The compound (1) preferably includes at least one selected from the group consisting of compounds represented by any of the following formulae (1a), (1b), (1c), (1d), (1e), and (1f).

[Chem. 6]

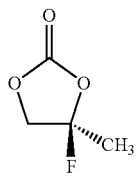

(1a)

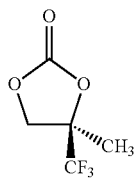

(1b)

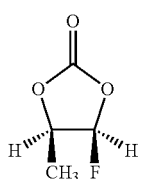

(1c)

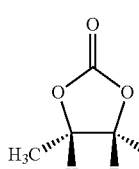

(1d)

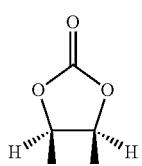

(1e)

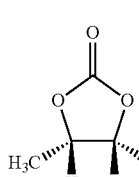

(1f)

The electrolyte solution of the invention preferably further contains an electrolyte salt.

The invention also relates to an electrochemical device including the electrolyte solution. The invention also relates to a lithium-ion secondary battery including the electrolyte solution.

The invention also relates to a module including the electrochemical device or the lithium-ion secondary battery.

Advantageous Effects of Invention

The electrolyte solution of the invention has any of the above structures, and thus can give a low resistance to an electrochemical device while maintaining the cycle characteristics of the electrochemical device and can reduce generation of gas during cycles although the electrolyte solution contains a fluorine-based solvent. An electrochemical device containing the electrolyte solution has excellent cycle characteristics and a low resistance, and less generates gas during cycles.

DESCRIPTION OF EMBODIMENTS

The invention will be specifically described hereinbelow.

The electrolyte solution of the invention contains a solvent.

The solvent contains a compound (1) represented by the following formula (1):

[Chem. 7]

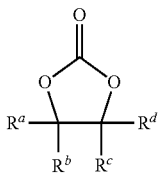

(1)

wherein $R^a$, $R^b$, $R^c$, and $R^d$ are the same as or different from each other, and are each —H, —F, —CH$_3$, or —CF$_3$; at least one of $R^a$, $R^b$, $R^c$, or $R^d$ is —F or —CF$_3$; and at least one of $R^a$, $R^b$, $R^c$, or $R^d$ is —CH$_3$.

The compound (1) represented by the formula (1) may include one compound or may include a combination of two or more compounds.

In order to give more improved cycle characteristics and a much lower resistance and to further reduce generation of gas, the compound (1) preferably includes at least one selected from the group consisting of compounds represented by any of the following formulae (1a), (1b), (1c), (1d), (1e), and (1f).

[Chem. 8]

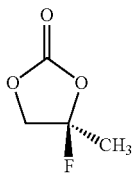

(1a)

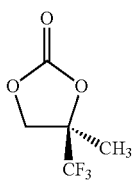

(1b)

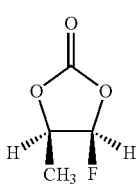

(1c)

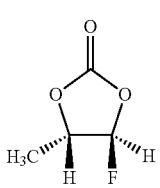

(1d)

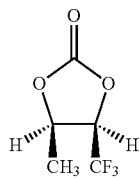

(1e)

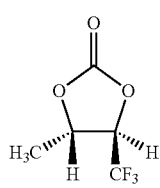

(1f)

In order to give a much lower resistance to an electrochemical device, particularly preferred among the compounds represented by any of the formulae (1a) to (1f) is at least one selected from the group consisting of the compound represented by the formula (1a) and the compound represented by the formula (1c).

The compound represented by the formula (1a) among the compounds (1) can be synthesized by charging hydroxyacetone, pyridine, and methylene chloride into an autoclave, introducing carbonyl fluoride thereinto, and heating the components.

The compound represented by the formula (1b) can be synthesized by adding tetrahydrofuran to trifluoromethyl ethylene carbonate, stirring the components, adding potassium t-butoxide and iodomethane, and stirring the components.

The compounds (1) other than the compound represented by the formula (1a) and the compound represented by the formula (1b) each can be synthesized using an appropriate starting material instead of hydroxyacetone or trifluoromethyl ethylene carbonate. A known synthesis method may be used.

The solvent contains a compound (2) represented by the following formula (2):

[Chem. 9]

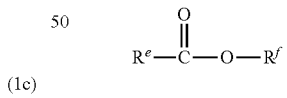

(2)

wherein $R^e$ is a C1-C5 linear or branched alkyl or alkoxy group optionally containing an ether bond; $R^f$ is a C1-C5 linear or branched alkyl group optionally containing an ether bond; and at least one of $R^e$ or $R^f$ contains a fluorine atom.

The compound (2) preferably has a fluorine content of 10 to 70% by mass. The compound (2) having a fluorine content within the above range can lead to improved high-temperature storage characteristics and cycle characteristics of an electrochemical device. The lower limit of the fluorine content is more preferably 15% by mass, still more preferably 25% by mass, particularly preferably 33% by mass. The upper limit of the fluorine content is more preferably 60% by mass, still more preferably 45% by mass.

The fluorine content is a value calculated based on the structural formula of the compound (2) by the following formula:

{(Number of fluorine atoms×19)/(molecular weight of compound (2))}×100(%).

When $R^e$ is an alkoxy group, examples of $R^e$ include fluorine-containing alkoxy groups such as $CF_3O—$, $CF_3CH_2O—$, $H_2CFCH_2O—$, $CF_2HCH_2O—$, $HCF_2CF_2CH_2O—$, $CF_3CF_2CH_2O—$, $(CF_3)_2CHO—$, $H(CF_2CF_2)_2CH_2O—$, $CF_3CF_2O—$, and $FCH_2O—$, fluorine-containing alkoxy groups containing an ether bond such as $C_2F_5OCF(CF_3)CH_2O—$ and $CF_3OCF(CF_3)CH_2O—$, and fluorine-free alkoxy groups such as $CH_3O—$, $C_2H_5O—$, $C_3H_7O—$, and $C_4H_5O—$.

When $R^e$ is an alkoxy group, examples of $R^f$ include fluorine-containing alkyl groups such as $CF_3—$, $CH_2F—$, $CF_2H—$, $CF_3CH_2—$, $H_2CFCH_2—$, $HCF_2CH_2—$, $HCF_2CF_2CH_2—$, $CF_3CF_2CH_2—$, $(CF_3)_2CH—$, $H(CF_2CF_2)_2CH_2—$, and $CF_3CF_2—$, fluorine-containing alkyl groups containing an ether bond such as $CF_3OCH_2CH_2—$, $CF_3CH_2OCH_2—$, $C_2F_5OCF(CF_3)CH_2—$, and $CF_3OCF(CF_3)CH_2—$, and fluorine-free alkyl groups such as $CH_3—$, $C_2H_5—$, $C_3H_7—$, and $C_4H_5—$.

Any combination of the above groups is selected so as to give a fluorine content within the above range.

When $R^e$ is an alkoxy group, specific examples of the compound (2) include $H_2CFOCOOCH_3$, $HCF_2OCOOCH_3$, $CF_3OCOOCH_3$, $H_2CFCH_2OCOOCH_3$, $HCF_2CH_2OCOOCH_3$, $CF_3CH_2OCOOCH_3$, $(CF_3CH_2O)_2CO$, $(HCF_2CF_2CH_2O)_2CO$, $(CF_3CF_2CH_2O)_2CO$, $((CF_3)_2CHO)_2CO$, $(H(CF_2CF_2)_2CH_2O)_2CO$, $CH_3OCOOCH_2CF_2CF_3$, $CH_3OCOOCH_2CF_2CF_2H$, $C_2H_5OCOOCH_2CF_2CF_2H$, $C_2H_5OCOOCH_2CF_3$, $CF_3CF_2CH_2OCOOCH_2CF_2CF_2H$, $HCF_2CF_2CH_2OCOOC_3H_7$, and $(CF_3)_2CHOCOOCH_3$.

Preferred among these is at least one selected from the group consisting of $H_2CFOCOOCH_3$, $(CF_3CH_2O)_2CO$, $(HCF_2CF_2CH_2O)_2CO$, $(CF_3CF_2CH_2O)_2CO$, $((CF_3)_2CHO)_2CO$, $(H(CF_2CF_2)_2CH_2O)_2CO$, $CH_3OCOOCH_2CF_2CF_3$, $CH_3OCOOCH_2CF_2CF_2H$, $C_2H_5OCOOCH_2CF_2CF_2H$, $CH_3OCOOCH_2CF_3$, $C_2H_5OCOOCH_2CF_3$, $CF_3CF_2CH_2OCOOCH_2CF_2CF_2H$, $HCF_2CF_2CH_2OCOOC_3H_7$, $(CF_3)_2CHOCOOCH_3$, and $CF_3CH_2OCOOCH_3$.

More preferred is at least one selected from the group consisting of $H_2CFOCOOCH_3$, $CF_3CH_2OCOOCH_3$, and $(CF_3CH_2O)_2CO$.

When $R^e$ is an alkyl group, examples of $R^e$ include $H_2CF—$, $HCF_2—$, $CF_3—$, $CF_3CF_2—$, $HCF_2CF_2—$, $CH_3CF_2—$, $HCF_2CH_2—$, $H_2CFCH_2—$, and $CF_3CH_2—$. In order to give a low resistance, good viscosity, and oxidation resistance to an electrochemical device, particularly preferred are $HCF_2—$, $CF_3—$, $CH_3CF_2—$, $CF_3CH_2—$, and $HCF_2CH_2—$.

When $R^e$ is an alkyl group, examples of $R^f$ include $CH_3—$, $C_2H_5—$, $CF_3—$, $CF_3CF_2—$, $(CF_3)_2CH—$, $CF_3CH_2—$, $CF_3CH_2CH_2—$, $CF_3CFHCF_2CH_2—$, $C_2F_5CH_2—$, $CF_2HCF_2CH_2—$, $C_2F_5CH_2CH_2—$, $CF_3CF_2CH_2—$, and $CF_3CF_2CF_2CH_2—$. In order to give a low resistance to an electrochemical device and to achieve good miscibility with other solvents, particularly preferred are $CH_3—$, $C_2H_5—$, $CF_3CH_2—$, and $CF_3CH_2CH_2—$.

When $R^e$ is an alkyl group, specific examples of the compound (2) include one or two or more of $CF_3CH_2C(=O)OCH_3$, $HCF_2C(=O)OCH_3$, $CF_3C(=O)OCH_2CH_2CF_3$, $HCF_2CH_2C(=O)OCH_3$, $CF_3C(=O)OCH_2C_2F_5$, $CF_3C(=O)OCH_2CF_2CF_2H$, $CF_3C(=O)OCH_2CF_3$, and $CF_3C(=O)OCH(CF_3)_2$. In order to give a low resistance and rate characteristics to an electrochemical device and to achieve good miscibility with other solvents, particularly preferred are $CF_3CH_2C(=O)OCH_3$, $HCF_2C(=O)OCH_3$, $CF_3C(=O)OCH_2C_2F_5$, $CF_3C(=O)OCH_2CF_2CF_2H$, $CF_3C(=O)OCH_2CF_3$, $CF_3C(=O)OCH(CF_3)_2$, and $HCF_2CH_2C(=O)OCH_3$.

The compound (2) represented by the formula (2) may include one compound or two or more compounds in combination.

The compound (2) can be synthesized by a conventionally known method.

The compound (1) is preferably contained in an amount of 0.001 to 99.999% by volume, more preferably 0.01 to 99.99% by volume, relative to the solvent. In order to give a much lower resistance to an electrochemical device, the amount thereof is still more preferably 0.1 to 70% by volume, further more preferably 1 to 60% by volume, still further more preferably 15 to 55% by volume, particularly preferably 20 to 50% by volume, relative to the solvent.

When two or more compounds are used in combination as the compound (1), the sum of the two or more compounds falls within the above range.

The compound (2) is preferably contained in an amount of 0.001 to 99.999% by volume, more preferably 0.01 to 99.99% by volume, relative to the solvent. In order to give a much lower resistance to an electrochemical device, the amount thereof is still more preferably 30 to 99.9% by volume, further more preferably 40 to 99% by volume, still further more preferably 45 to 85% by volume, particularly preferably 50 to 70% by volume, relative to the solvent.

When two or more compounds are used in combination as the compound (2), the sum of the two or more compounds falls within the above range.

The sum of the amounts of the compound (1) and the compound (2) is preferably 10 to 100% by volume relative to the solvent. In order to give a much lower resistance to an electrochemical device, the sum is more preferably 40 to 99% by volume, still more preferably 60 to 95% by volume, relative to the solvent.

The solvent in the invention may further contain at least one selected from the group consisting of a non-fluorinated saturated cyclic carbonate and a non-fluorinated acyclic carbonate.

Examples of the non-fluorinated saturated cyclic carbonate include non-fluorinated saturated cyclic carbonates containing a C2-C4 alkylene group.

In order to give a high permittivity and good viscosity, the non-fluorinated saturated cyclic carbonate preferably includes at least one selected from the group consisting of ethylene carbonate, propylene carbonate, and butylene carbonate.

The non-fluorinated saturated cyclic carbonates may be used alone or in any combination of two or more at any ratio.

Examples of the non-fluorinated acyclic carbonate include hydrocarbon-based acyclic carbonates such as $CH_3OCOOCH_3$ (dimethyl carbonate, DMC), $CH_3CH_2OCOOCH_2CH_3$ (diethyl carbonate, DEC), $CH_3CH_2OCOOCH_3$ (ethyl methyl carbonate, EMC), $CH_3OCOOCH_2CH_2CH_3$ (methyl propyl carbonate), methyl butyl carbonate, ethyl propyl carbonate, and ethyl butyl carbonate. Preferred is at least one selected from the group consisting of ethyl methyl carbonate, diethyl carbonate, and dimethyl carbonate.

The non-fluorinated acyclic carbonates may be used alone or in any combination of two or more at any ratio.

The non-fluorinated saturated cyclic carbonate is preferably in an amount of 0 to 90% by volume, more preferably 1 to 60% by volume, still more preferably 5 to 40% by volume, relative to the solvent.

The non-fluorinated acyclic carbonate is preferably in an amount of 0 to 90% by volume, more preferably 1 to 60% by volume, still more preferably 5 to 40% by volume, relative to the solvent.

The sum of the non-fluorinated saturated cyclic carbonate and the non-fluorinated acyclic carbonate is preferably 0 to 90% by volume, more preferably 1 to 60% by volume, still more preferably 5 to 40% by volume, relative to the solvent.

The solvent in the invention may further contain at least one selected from the group consisting of a non-fluorinated saturated cyclic ester and a non-fluorinated acyclic ester.

Examples of the non-fluorinated saturated cyclic ester include non-fluorinated saturated cyclic esters containing a C2-C4 alkylene group.

Specific examples of the non-fluorinated saturated cyclic esters containing a C2-C4 alkylene group include β-propiolactone, γ-butyrolactone, and δ-valerolactone. In order to improve the degree of dissociation of lithium ions and to improve the load characteristics, particularly preferred are γ-butyrolactone and δ-valerolactone.

The non-fluorinated saturated cyclic esters may be used alone or in any combination of two or more at any ratio.

Examples of the non-fluorinated acyclic ester include methyl acetate, ethyl acetate, butyl acetate, methyl propionate, ethyl propionate, propyl propionate, and butyl propionate.

Preferred among these are ethyl propionate and propyl propionate, particularly preferred is ethyl propionate.

The non-fluorinated acyclic esters may be used alone or in any combination of two or more at any ratio.

The non-fluorinated saturated cyclic ester is preferably in an amount of 0 to 90% by volume, more preferably 0.001 to 90% by volume, still more preferably 1 to 60% by volume, particularly preferably 5 to 40% by volume, relative to the solvent.

The non-fluorinated acyclic ester is preferably in an amount of 0 to 90% by volume, more preferably 0.001 to 90% by volume, still more preferably 1 to 60% by volume, particularly preferably 5 to 40% by volume, relative to the solvent.

The sum of the non-fluorinated saturated cyclic ester and the non-fluorinated acyclic ester is preferably 0 to 90% by volume, more preferably 1 to 60% by volume, still more preferably 5 to 40% by volume, relative to the solvent.

The solvent in the invention may further contain a fluorinated saturated cyclic carbonate other than the above compound (1).

The fluorinated saturated cyclic carbonate other than the above compound (1) is a saturated cyclic carbonate containing a fluorine atom. Specific examples thereof include a fluorinated saturated cyclic carbonate (A) (other than the compound (1)) represented by the following formula (A):

[Chem. 10]

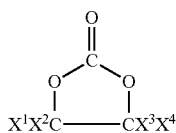

(A)

(wherein $X^1$ to $X^4$ are the same as or different from each other, and are each —H, —$CH_3$, —$C_2H_5$, —F, a fluorinated alkyl group optionally containing an ether bond, or a fluorinated alkoxy group optionally containing an ether bond; at least one of $X^1$ to $X^4$ is —F, a fluorinated alkyl group optionally containing an ether bond, or a fluorinated alkoxy group optionally containing an ether bond). Examples of the fluorinated alkyl group include —$CF_3$, —$CF_2H$, and —$CH_2F$.

The presence of the fluorinated saturated cyclic carbonate (A) in the electrolyte solution of the invention when applied to a lithium-ion secondary battery, for example, can lead to improved oxidation resistance of the electrolyte solution, providing stable, excellent charge and discharge characteristics.

The term "ether bond" herein means a bond represented by —O—.

In the formula (A), in order to achieve good permittivity and oxidation resistance, one or two of $X^1$ to $X^4$ is/are each preferably —F, a fluorinated alkyl group optionally containing an ether bond, or a fluorinated alkoxy group optionally containing an ether bond.

In the formula (A), in anticipation of a decrease in viscosity at low temperature, an increase in flash point, and improvement in solubility of an electrolyte salt, $X^1$ to $X^4$ are each preferably —H, —F, a fluorinated alkyl group (a), a fluorinated alkyl group (b) containing an ether bond, or a fluorinated alkoxy group (c).

The fluorinated alkyl group (a) is an alkyl group in which at least one hydrogen atom is replaced by a fluorine atom. The fluorinated alkyl group (a) preferably has a carbon number of 1 to 20, more preferably 2 to 17, still more preferably 2 to 7, particularly preferably 2 to 5.

Too large a carbon number may cause poor low-temperature characteristics and low solubility of the electrolyte salt. Too small a carbon number may cause low solubility of the electrolyte salt, low discharge efficiency, and increased viscosity, for example.

Examples of the fluorinated alkyl group (a) having a carbon number of 1 include $CFH_2$—, $CF_2H$—, and $CF_3$—.

In order to achieve good solubility of the electrolyte salt, preferred examples of the fluorinated alkyl group (a) having a carbon number of 2 or greater include fluorinated alkyl groups represented by the following formula (a-1):

wherein $R^1$ is an alkyl group having a carbon number of 1 or greater and optionally containing a fluorine atom; $R^2$ is a C1-C3 alkylene group optionally containing a fluorine atom; and at least one selected from $R^1$ and $R^2$ contains a fluorine atom.

$R^1$ and $R^2$ each may further contain an atom other than carbon, hydrogen, and fluorine atoms.

$R^1$ is an alkyl group having a carbon number of 1 or greater and optionally containing a fluorine atom. $R^1$ is preferably a C1-C16 linear or branched alkyl group. The carbon number of $R^1$ is more preferably 1 to 6, still more preferably 1 to 3.

Specifically, for example, $CH_3$—, $CH_3CH_2$—, $CH_3CH_2CH_2$—, $CH_3CH_2CH_2CH_2$—, and groups represented by the following formulae:

[Chem. 11]

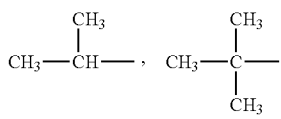

may be mentioned as linear or branched alkyl groups for $R^1$.

Examples of $R^1$ which is a linear alkyl group containing a fluorine atom include $CF_3$—, $CF_3CH_2$—, $CF_3CF_2$—, $CF_3CH_2CH_2$—, $CF_3CF_2CH_2$—, $CF_3CF_2CF_2$—, $CF_3CH_2CF_2$—, $CF_3CH_2CH_2CH_2$—, $CF_3CF_2CH_2CH_2$—, $CF_3CH_2CF_2CH_2$—, $CF_3CF_2CF_2CH_2$—, $CF_3CF_2CF_2CF_2$—, $CF_3CF_2CH_2CF_2$—, $CF_3CH_2CH_2CH_2CH_2$—, $CF_3CF_2CH_2CH_2CH_2$—, $CF_3CH_2CF_2CH_2CH_2$—, $CF_3CF_2CF_2CH_2CH_2$—, $CF_3CF_2CF_2CF_2CH_2$—, $CF_3CH_2CF_2CF_2CH_2$—, $CF_3CF_2CH_2CH_2CH_2CH_2$—, $CF_3CF_2CF_2CF_2CH_2CH_2$—, $CF_3CF_2CH_2CF_2CH_2CH_2$—, $HCF_2$—, $HCF_2CH_2$—, $HCF_2CF_2$—, $HCF_2CH_2CH_2$—, $HCF_2CF_2CH_2$—, $HCF_2CH_2CF_2$—, $HCF_2CF_2CH_2CH_2$—, $HCF_2CH_2CF_2CH_2$—, $HCF_2CF_2CF_2CF_2$—, $HCF_2CF_2CH_2CH_2CH_2$—, $HCF_2CH_2CF_2CH_2CH_2$—, $HCF_2CF_2CF_2CH_2CH_2$—, $HCF_2CF_2CF_2CF_2CH_2CH_2$—, $FCH_2$—, $FCH_2CH_2$—, $FCH_2CF_2$—, $FCH_2CF_2CH_2$—, $FCH_2CF_2CF_2$—, $CH_3CF_2CH_2$—, $CH_3CF_2CF_2$—, $CH_3CH_2CH_2$—, $CH_3CF_2CH_2CF_2$—, $CH_3CF_2CF_2CF_2$—, $CH_3CH_2CF_2CF_2$—, $CH_3CF_2CH_2CF_2CH_2$—, $CH_3CF_2CF_2CF_2CH_2$—, $CH_3CF_2CF_2CH_2CH_2$—, $CH_3CH_2CF_2CF_2CH_2$—, $CH_3CF_2CH_2CF_2CH_2$—, $CH_3CF_2CH_2CF_2CH_2CH_2$—, $CH_3CF_2CH_2CF_2CH_2CH_2$—, $HCFClCF_2CH_2$—, $HCF_2CFClCH_2$—, $HCF_2CFClCF_2CFClCH_2$—, and $HCFClCF_2CFClCF_2CH_2$—.

Examples of $R^1$ which is a branched alkyl group containing a fluorine atom include those represented by the following formulae.

[Chem. 12]

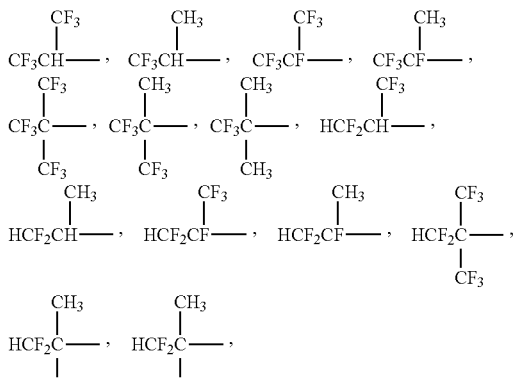

[Chem. 13]

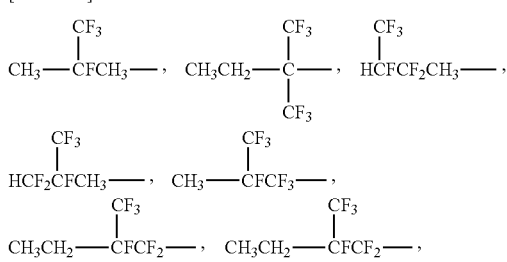

[Chem. 14 - continued]

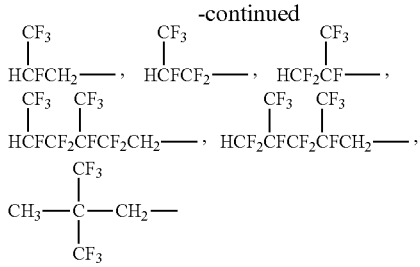

The presence of a branch such as —$CH_3$ or —$CF_3$ may easily cause high viscosity. Thus, the number of such branches is more preferably small (one) or zero.

$R^2$ is a C1-C3 alkylene group optionally containing a fluorine atom. $R^2$ may be either linear or branched. Examples of a minimum structural unit constituting such a linear or branched alkylene group are shown below. $R^2$ is constituted by one or combination of these units.

(i) Linear Minimum Structural Units

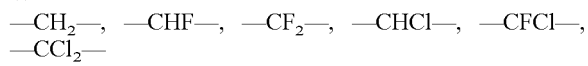

(ii) Branched Minimum Structural Units

[Chem. 14]

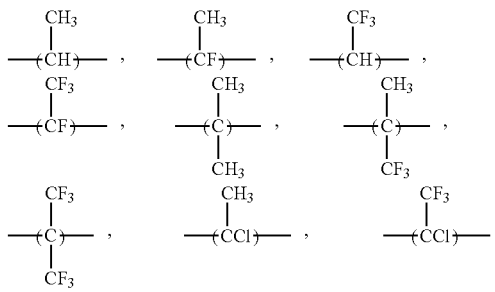

Preferred among these exemplified units are Cl-free structural units because such units may not be dehydrochlorinated by a base, and thus may be more stable.

$R^2$ which is a linear group consists only of any of the above linear minimum structural units, and is preferably —$CH_2$—, —$CH_2CH_2$—, or $CF_2$—. In order to further improve the solubility of the electrolyte salt, —$CH_2$— or —$CH_2CH_2$— is more preferred.

$R^2$ which is a branched group includes at least one of the above branched minimum structural units. A preferred example thereof is a group represented by —$(CX^aX^b)$—, wherein $X^a$ is H, F, $CH_3$, or $CF_3$; $X^b$ is $CH_3$ or $CF_3$; when $X^b$ is $CF_3$, $X^a$ is H or $CH_3$. Such a group can much further improve the solubility of the electrolyte salt.

For example, $CF_3CF_2$—, $HCF_2CF_2$—, $H_2CFCF_2$—, $CH_3CF_2$—, $CF_3CF_2CF_2$—, $HCF_2CF_2CF_2$—, $H_2CFCF_2CF_2$—, $CH_3CF_2CF_2$—, and those represented by the following formulae:

[Chem. 15]

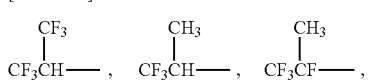

-continued

[Chem. 16]

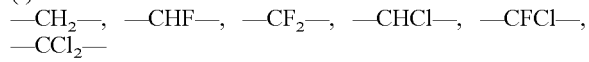

may be mentioned as preferred examples of the fluorinated alkyl group (a).

The fluorinated alkyl group (b) containing an ether bond is an alkyl group containing an ether bond in which at least one hydrogen atom is replaced by a fluorine atom. The fluorinated alkyl group (b) containing an ether bond preferably has a carbon number of 2 to 17. Too large a carbon number may cause high viscosity of the fluorinated saturated cyclic carbonate (A). This may also cause the presence of many fluorine-containing groups, resulting in poor solubility of the electrolyte salt due to reduction in permittivity, and poor miscibility with other solvents. Accordingly, the carbon number of the fluorinated alkyl group (b) containing an ether bond is preferably 2 to 10, more preferably 2 to 7.

The alkylene group which constitutes the ether moiety of the fluorinated alkyl group (b) containing an ether bond is a linear or branched alkylene group. Examples of a minimum structural unit constituting such a linear or branched alkylene group are shown below.

(i) Linear Minimum Structural Units

—CH$_2$—, —CHF—, —CF$_2$—, —CHCl—, —CFCl—, —CCl$_2$—

(ii) Branched Minimum Structural Units

[Chem. 17]

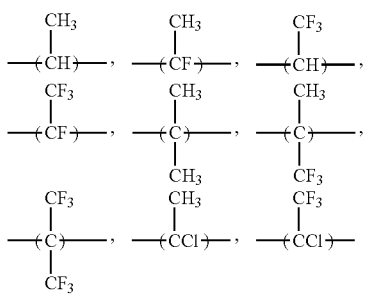

The alkylene group may be constituted by one of these minimum structural units, or may be constituted by multiple linear units (i), by multiple branched units (ii), or by a combination of a linear unit (i) and a branched unit (ii). Preferred examples will be mentioned in detail later.

Preferred among these exemplified units are Cl-free structural units because such units may not be dehydrochlorinated by a base, and thus may be more stable.

A still more preferred example of the fluorinated alkyl group (b) containing an ether bond is a group represented by the following formula (b-1):

$$R^3—(OR^4)_{n1}— \quad (b-1)$$

wherein $R^3$ is preferably a C1-C6 alkyl group optionally containing a fluorine atom; $R^4$ is preferably a C1-C4 alkylene group optionally containing a fluorine atom; n1 is an integer of 1 to 3; and at least one selected from $R^3$ and $R^4$ contains a fluorine atom.

Examples of $R^3$ and $R^4$ include the following groups, and any appropriate combination of these groups can provide the fluorinated alkyl group (b) containing an ether bond represented by the formula (b-1). Still, the groups are not limited thereto.

(1) $R^3$ is preferably an alkyl group represented by $X^c{}_3C—(R^5)_{n2}—$, wherein three $X^c$s are the same as or different from each other, and are each H or F; $R^5$ is a C1-C5 alkylene group optionally containing a fluorine atom; and n2 is 0 or 1.

When n2 is 0, $R^3$ may be CH$_3$—, CF$_3$—, HCF$_2$—, or H$_2$CF—, for example.

When n2 is 1, specific examples of $R^3$ which is a linear group include CF$_3$CH$_2$—, CF$_3$CF$_2$—, CF$_3$CH$_2$CH$_2$—, CF$_3$CF$_2$CH$_2$—, CF$_3$CF$_2$CF$_2$—, CF$_3$CH$_2$CF$_2$—, CF$_3$CH$_2$CH$_2$CH$_2$—, CF$_3$CF$_2$CH$_2$CH$_2$—, CF$_3$CH$_2$CF$_2$CH$_2$—, CF$_3$CF$_2$CF$_2$CH$_2$—, CF$_3$CF$_2$CF$_2$CF$_2$—, CF$_3$CF$_2$CH$_2$CF$_2$—, CF$_3$CH$_2$CH$_2$CH$_2$CH$_2$—, CF$_3$CF$_2$CH$_2$CH$_2$CH$_2$—, CF$_3$CH$_2$CF$_2$CH$_2$CH$_2$—, CF$_3$CF$_2$CF$_2$CH$_2$CH$_2$—, CF$_3$CF$_2$CF$_2$CF$_2$CH$_2$—, CF$_3$CF$_2$CH$_2$CF$_2$CH$_2$—, CF$_3$CF$_2$CH$_2$CH$_2$CH$_2$CH$_2$—, CF$_3$CF$_2$CF$_2$CF$_2$CH$_2$CH$_2$—, CF$_3$CF$_2$CH$_2$CF$_2$CH$_2$CH$_2$—, HCF$_2$CH$_2$—, HCF$_2$CF$_2$—, HCF$_2$CH$_2$CH$_2$—, HCF$_2$CF$_2$CH$_2$—, HCF$_2$CH$_2$CF$_2$—, HCF$_2$CF$_2$CH$_2$CH$_2$—, HCF$_2$CH$_2$CF$_2$CH$_2$—, HCF$_2$CF$_2$CF$_2$CF$_2$—, HCF$_2$CF$_2$CH$_2$CH$_2$CH$_2$—, HCF$_2$CH$_2$CF$_2$CH$_2$CH$_2$—, HCF$_2$CF$_2$CF$_2$CF$_2$CH$_2$—, HCF$_2$CF$_2$CF$_2$CF$_2$CH$_2$CH$_2$—, FCH$_2$CH$_2$—, FCH$_2$CF$_2$—, FCH$_2$CF$_2$CH$_2$—, CH$_3$CF$_2$—, CH$_3$CH$_2$—, CH$_3$CF$_2$CH$_2$—, CH$_3$CF$_2$CF$_2$—, CH$_3$CH$_2$CH$_2$—, CH$_3$CF$_2$CH$_2$CF$_2$—, CH$_3$CF$_2$CF$_2$CF$_2$—, CH$_3$CH$_2$CF$_2$CF$_2$—, CH$_3$CH$_2$CH$_2$CH$_2$—, CH$_3$CF$_2$CH$_2$CF$_2$CH$_2$—, CH$_3$CF$_2$CF$_2$CF$_2$CH$_2$—, CH$_3$CF$_2$CF$_2$CH$_2$CH$_2$—, CH$_3$CH$_2$CF$_2$CF$_2$CH$_2$—, CH$_3$CF$_2$CH$_2$CF$_2$CH$_2$—, and CH$_3$CH$_2$CF$_2$CF$_2$CH$_2$CH$_2$—.

When n2 is 1, those represented by the following formulae:

[Chem. 18]

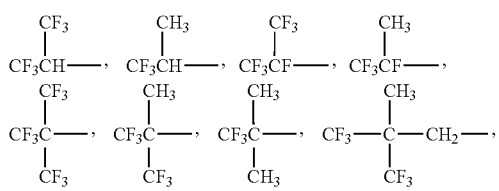

-continued

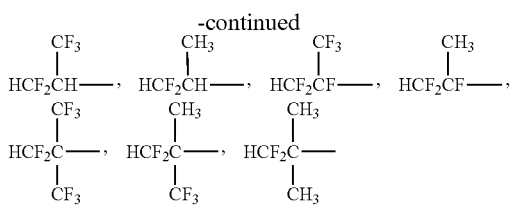

may be mentioned as examples of $R^3$ which is a branched group.

A group having a branch such as —$CH_3$ or —$CF_3$ may easily cause high viscosity. Thus, $R^3$ is more preferably a linear group.

(2) In —$(OR^4)_{n1}$— of the formula (b-1), n1 is an integer of 1 to 3, preferably 1 or 2. When n1 is 2 or 3, $R^4$s may be the same as or different from each other.

Preferred specific examples of $R^4$ include the following linear or branched groups.

Examples of the linear groups include —$CH_2$—, —CHF—, —$CF_2$—, —$CH_2CH_2$—, —$CF_2CH_2$—, —$CF_2CF_2$—, —$CH_2CF_2$—, —$CH_2CH_2CH_2$—, —$CH_2CH_2CF_2$—, —$CH_2CF_2CH_2$—, —$CH_2CF_2CF_2$—, —$CF_2CH_2CH_2$—, —$CF_2CF_2CH_2$—, —$CF_2CH_2CF_2$—, and —$CF_2CF_2CF_2$—.

Those represented by the following formulae:

[Chem. 19]

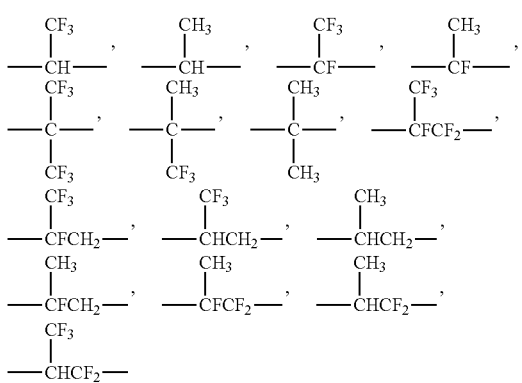

may be mentioned as examples of the branched groups.

The fluorinated alkoxy group (c) is an alkoxy group in which at least one hydrogen atom is replaced by a fluorine atom. The fluorinated alkoxy group (c) preferably has a carbon number of 1 to 17. The carbon number is more preferably 1 to 6.

The fluorinated alkoxy group (c) is particularly preferably a fluorinated alkoxy group represented by $X^d_3C$—$(R^6)_{n3}$—O—, wherein three $X^d$s are the same as or different from each other, and are each H or F; $R^6$ is preferably a C1-C5 alkylene group optionally containing a fluorine atom; n3 is 0 or 1; and any of the three $X^d$s contain a fluorine atom.

Specific examples of the fluorinated alkoxy group (c) include fluorinated alkoxy groups in which an oxygen atom binds to an end of an alkyl group mentioned as an example for $R^1$ in the formula (a-1).

The fluorinated alkyl group (a), the fluorinated alkyl group (b) containing an ether bond, and the fluorinated alkoxy group (c) in the fluorinated saturated cyclic carbonate (A) each preferably have a fluorine content of 10% by mass or more. Too low a fluorine content may cause a failure in sufficiently achieving an effect of increasing the flash point. Thus, the fluorine content is more preferably 20% by mass or more, still more preferably 30% by mass or more. The upper limit thereof is usually 85% by mass.

The fluorine content of each of the fluorinated alkyl group (a), the fluorinated alkyl group (b) containing an ether bond, and the fluorinated alkoxy group (c) is a value calculated based on the corresponding structural formula by the following formula:

{(Number of fluorine atoms×19)/(formula weight of group)}×100(%).

The fluorine content in the whole fluorinated saturated cyclic carbonate (A) is preferably 5% by mass or more, more preferably 10% by mass or more. The upper limit thereof is usually 76% by mass. In order to achieve good permittivity and oxidation resistance, the fluorine content in the whole fluorinated saturated cyclic carbonate (A) is preferably 10 to 70% by mass, more preferably 15 to 60% by mass.

The fluorine content in the fluorinated saturated cyclic carbonate (A) is a value calculated based on the structural formula of the fluorinated saturated cyclic carbonate (A) by the following formula:

{(Number of fluorine atoms×19)/(molecular weight of fluorinated saturated cyclic carbonate (A)}×100(%).

Specific examples of the fluorinated saturated cyclic carbonate (A) include the following.

In the formula (A), specific examples of the fluorinated saturated cyclic carbonate (A) in which at least one of $X^1$ to $X^4$ is —F include those represented by the following formulae.

[Chem. 20]

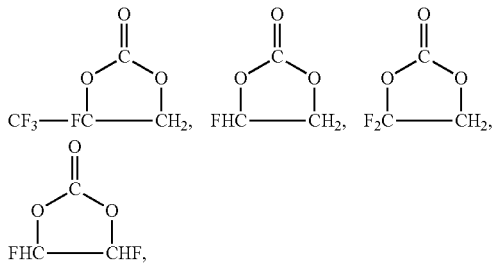

These compounds have a high withstand voltage and give good solubility of the electrolyte salt.

Alternatively, those represented by the following formulae:

[Chem. 21]

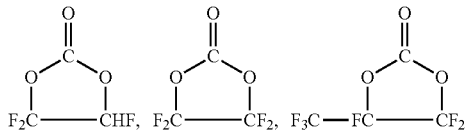

may also be used.

Those represented by the following formulae:

[Chem. 22]

$$\text{H}_2\text{C}-\text{CH}-\text{CH}_2\text{CF}_2\text{CF}_3 \text{ (cyclic carbonate)},$$

$$\text{H}_2\text{C}-\text{CH}-\text{CH}_2\text{CF}(\text{CF}_3)_2 \text{ (cyclic carbonate)}, \quad \text{H}_2\text{C}-\text{CH}-\text{CF}_3 \text{ (cyclic carbonate)},$$

$$\text{H}_2\text{C}-\text{CH}-\text{CH}_2\text{F} \text{ (cyclic carbonate)}, \quad \text{H}_2\text{C}-\text{CH}-\text{CF}_2\text{H} \text{ (cyclic carbonate)},$$

$$\text{H}_2\text{C}-\text{C}(\text{CF}_3)_2 \text{ (cyclic carbonate)}, \quad \text{H}_2\text{C}-\text{CH}-\text{CH}_2\text{CF}_2\text{CF}_2\text{CF}_2\text{CF}_3 \text{ (cyclic carbonate)},$$

$$\text{H}_2\text{C}-\text{CH}-\text{CH}_2\text{CF}_3 \text{ (cyclic carbonate)},$$

[Chem. 23]

$$\text{CF}_3\text{CF}_2-\text{CH}-\text{CH}_2 \text{ (cyclic carbonate)}, \quad \text{HCF}_2\text{CF}_2-\text{CH}-\text{CH}_2 \text{ (cyclic carbonate)},$$

$$\text{H}_2\text{CFCF}_2-\text{CH}-\text{CH}_2 \text{ (cyclic carbonate)}, \quad \text{CH}_3\text{CF}_2-\text{CH}-\text{CH}_2 \text{ (cyclic carbonate)},$$

$$\text{CF}_3\text{CF}_2\text{CF}_2-\text{CH}-\text{CH}_2 \text{ (cyclic carbonate)}, \quad \text{CF}_3\text{CF}_2\text{CF}_2\text{CF}_2-\text{CH}-\text{CH}_2 \text{ (cyclic carbonate)},$$

$$\text{HCF}_2\text{CF}_2\text{CF}_2-\text{CH}-\text{CH}_2 \text{ (cyclic carbonate)},$$

$$\text{HCF}_2\text{CF}_2\text{CF}_2\text{CF}_2-\text{CH}-\text{CH}_2 \text{ (cyclic carbonate)},$$

[Chem. 24]

$$\text{H}_2\text{CFCF}_2\text{CF}_2-\text{CH}-\text{CH}_2 \text{ (cyclic carbonate)},$$

$$\text{CH}_3\text{CF}_2\text{CF}_2-\text{CH}-\text{CH}_2 \text{ (cyclic carbonate)},$$

may be mentioned as specific examples of the fluorinated saturated cyclic carbonate in which at least one of $X^1$ to $X^4$ is a fluorinated alkyl group (a) and the others thereof are —H.

Those represented by the following formulae:

[Chem. 25]

$$\text{CF}_3\text{O}-\text{CH}-\text{CH}_2 \text{ (cyclic carbonate)}, \quad \text{CF}_3-\text{OCH}_2-\text{CH}-\text{CH}_2 \text{ (cyclic carbonate)},$$

$$\text{HCF}_2-\text{OCH}_2-\text{CH}-\text{CH}_2 \text{ (cyclic carbonate)},$$

$$\text{CF}_3\text{CH}_2-\text{OCH}_2-\text{CH}-\text{CH}_2 \text{ (cyclic carbonate)},$$

$$\text{CF}_3\text{CF}_2\text{CH}_2-\text{OCH}_2-\text{CH}-\text{CH}_2 \text{ (cyclic carbonate)},$$

$$\text{CF}_3\text{CF}_2\text{CF}_3-\text{OCH}_2-\text{CH}-\text{CH}_2 \text{ (cyclic carbonate)},$$

$$\text{CF}_3(\text{CF}_3)\text{CH}-\text{OCH}_2-\text{CH}-\text{CH}_2 \text{ (cyclic carbonate)},$$

$$(\text{CF}_3)_3\text{C}-\text{OCH}_2-\text{CH}-\text{CH}_2 \text{ (cyclic carbonate)},$$

$$\text{CH}_3(\text{CF}_3)_2\text{CCH}_2-\text{OCH}_2-\text{CH}-\text{CH}_2 \text{ (cyclic carbonate)},$$

[Chem. 26]

$$\text{FCH}_2\text{CF}_2\text{CF}_2-\text{OCH}_2-\text{CH}-\text{CH}_2 \text{ (cyclic carbonate)},$$

-continued
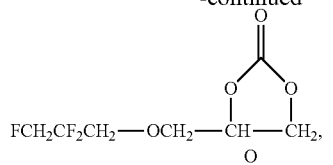
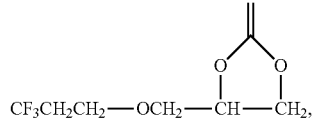
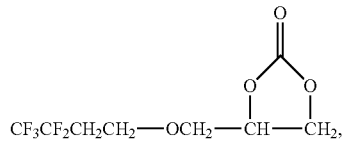
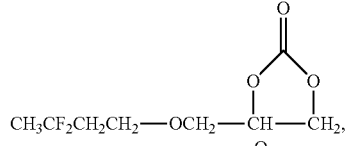
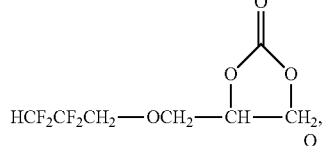
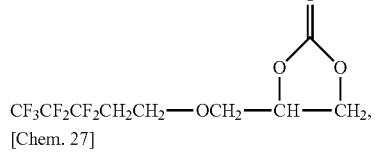
[Chem. 27]
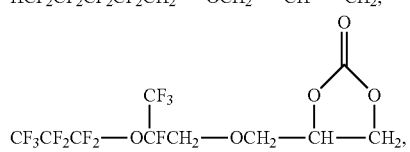
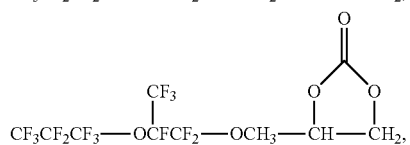
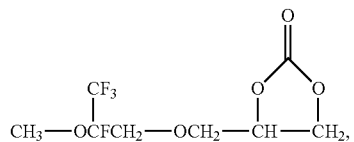
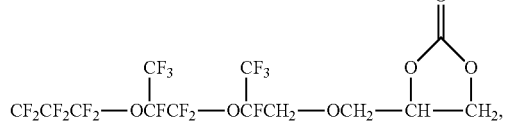
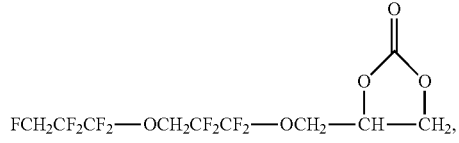
-continued
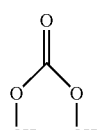
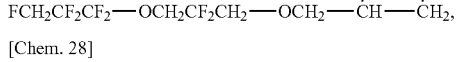
[Chem. 28]
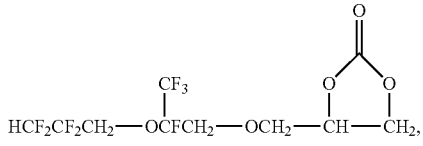
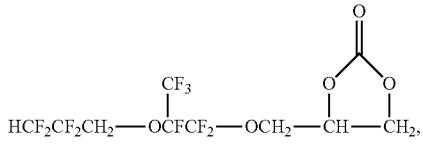
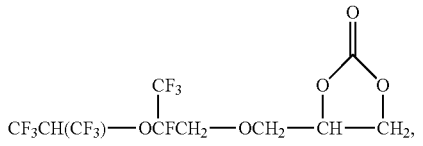
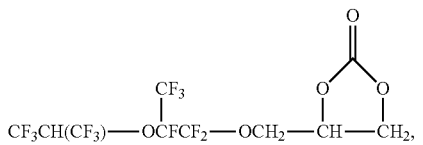
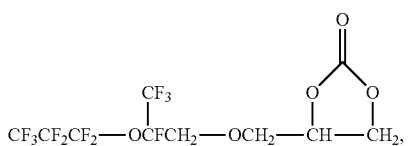
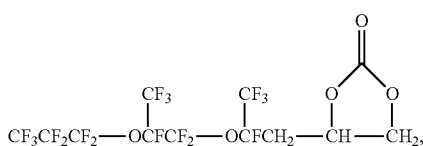
[Chem. 29]
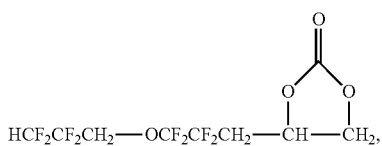
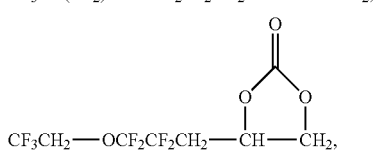

-continued

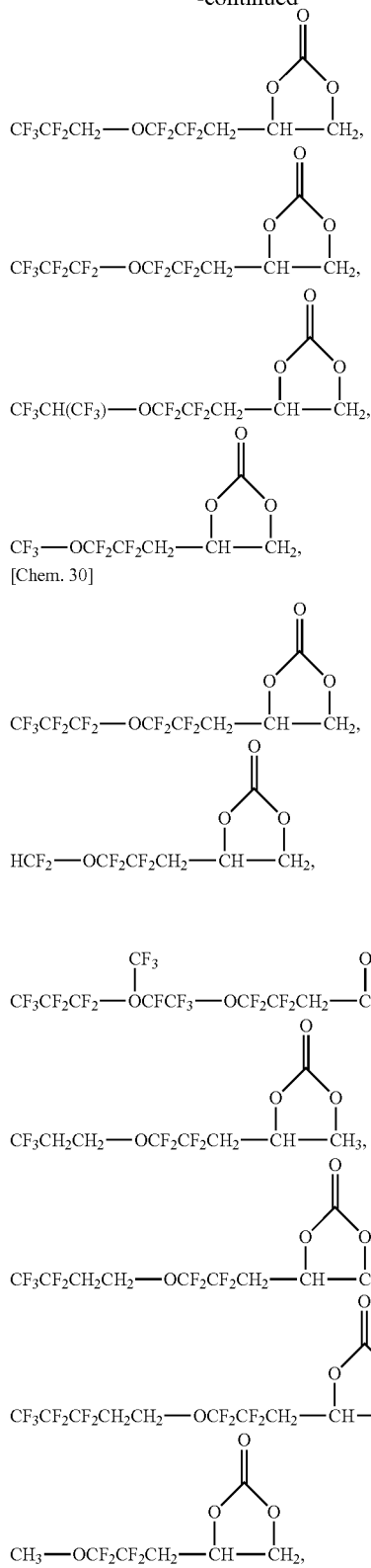

[Chem. 30]

may be mentioned as specific examples of the fluorinated saturated cyclic carbonate in which at least one of $X^1$ to $X^4$ is a fluorinated alkyl group (b) containing an ether bond or a fluorinated alkoxy group (c) and the others thereof are —H.

In particular, the fluorinated saturated cyclic carbonate is preferably any of the following compounds.

[Chem. 31]

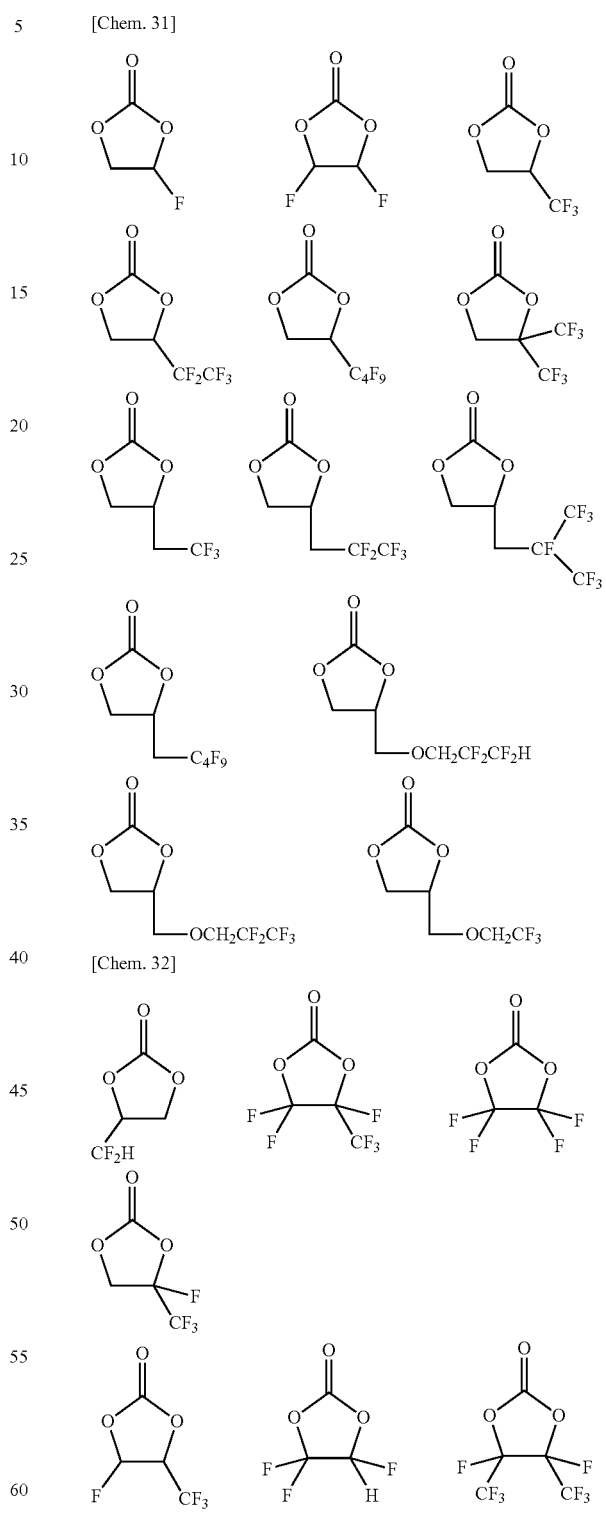

[Chem. 32]

The fluorinated saturated cyclic carbonate (A) is preferably fluoroethylene carbonate, difluoroethylene carbonate, or 4-trifluoromethyl-ethylene carbonate.

The fluorinated saturated cyclic carbonate (A) is not limited to the above specific examples. The above fluorinated saturated cyclic carbonates (A) may be used alone or in any combination of two or more at any ratio.

In the electrolyte solution of the invention, the fluorinated saturated cyclic carbonate (A) is preferably in an amount of 0 to 50% by volume, more preferably 1 to 50% by volume, still more preferably 5 to 30% by volume, particularly preferably 10 to 20% by volume, relative to the solvent. The fluorinated saturated cyclic carbonate (A) in an amount within the above range can improve the oxidation resistance of the electrolyte solution.

The solvent in the invention may further contain a fluorinated acyclic carbonate other than the compound (2). Examples of such a fluorinated acyclic carbonate include $(C_3F_7OCF(CF_3)$ $CF_2OCF(CF_3)CH_2O)_2CO_3$ $(C_3F_7OCF(CF_3)CH_2O)_2CO$, $C_3F_7OCF(CF_3)CH_2OCOOC_3H_7$, and $(C_3F_7OCF(CF_3)CH_2O)_2CO$.

The solvent in the invention may further contain a fluorinated acyclic ester other than the compound (2).

In the solvent, preferably, the amount of the compound (1) is 0.5 to 65% by volume, the amount of the compound (2) is 35 to 85% by volume, and the amount of the compound other than the compounds (1) and (2) is 0 to 35% by volume.

The compound other than the compounds (1) and (2) preferably includes at least one selected from the group consisting of the aforementioned non-fluorinated saturated cyclic carbonate, non-fluorinated acyclic carbonate, non-fluorinated acyclic ester, and fluorinated cyclic carbonate (A), more preferably include at least one selected from the group consisting of ethylene carbonate, propylene carbonate, ethyl methyl carbonate, dimethyl carbonate, ethyl propionate, fluoroethylene carbonate, trifluoromethyl ethylene carbonate, and difluoroethylene carbonate.

When the solvent consists only of the compound (1) and the compound (2), preferably, the amount of the compound (1) is 15 to 40% by volume and the amount of the compound (2) is 60 to 85% by volume relative to the solvent.

When the solvent contains a compound other than the compound (1) and the compound (2), preferably, the amount of the compound (1) is 0.5 to 30% by volume, the amount of the compound (2) is 50 to 70% by volume, and the amount of the compound other than the compounds (1) and (2) is 10 to 35% by volume, relative to the solvent.

The solvent is preferably a non-aqueous solvent, and the electrolyte solution of the invention is preferably a non-aqueous electrolyte solution.

The electrolyte solution of the invention preferably further contains an electrolyte salt. Examples of the electrolyte salt used include lithium salts, ammonium salts, and metal salts, as well as any of those to be used for an electrolyte solution such as liquid salts (ionic liquids), inorganic polymer salts, and organic polymer salts.

The electrolyte salt of the electrolyte solution for a lithium-ion secondary battery is preferably a lithium salt.

Any lithium salt may be used. Specific examples thereof include the following:

inorganic lithium salts such as $LiPF_6$, $LiBF_4$, $LiClO_4$, $LiAlF_4$, $LiSbF_6$, $LiTaF_6$, and $LiWF_7$;

lithium tungstates such as $LiWOF_5$;

lithium carboxylates such as $HCO_2Li$, $CH_3CO_2Li$, $CH_2FCO_2Li$, $CHF_2CO_2Li$, $CF_3CO_2Li$, $CF_3CH_2CO_2Li$, $CF_3CF_2CO_2Li$, $CF_3CF_2CF_2CO_2Li$, and $CF_3CF_2CF_2CF_2CO_2Li$;

lithium sulfonates such as $FSO_3Li$, $CH_3SO_3Li$, $CH_2FSO_3Li$, $CHF_2SO_3Li$, $CF_3SO_3Li$, $CF_3CF_2SO_3Li$, $CF_3CF_2CF_2SO_3Li$, and $CF_3CF_2CF_2CF_2SO_3Li$;

lithium imide salts such as $LiN(FCO)_2$, $LiN(FCO)(FSO_2)$, $LiN(FSO_2)_2$, $LiN(FSO_2)(CF_3SO_2)$, $LiN(CF_3SO_2)_2$, $LiN(C_2F_5SO_2)_2$, lithium cyclic 1,2-perfluoroethanedisulfonylimide, lithium cyclic 1,3-perfluoropropanedisulfonylimide, and $LiN(CF_3SO_2)(C_4F_9SO_2)$;

lithium methide salts such as $LiC(FSO_2)_3$, $LiC(CF_3SO_2)_3$, and $LiC(C_2F_5SO_2)_3$;

lithium oxalatoborates such as lithium difluorooxalatoborate and lithium bis(oxalato)borate;

lithium oxalatophosphates such as lithium tetrafluorooxalatophosphate, lithium difluorobis(oxalato)phosphate, and lithium tris(oxalato)phosphate; and fluorine-containing organic lithium salts such as salts represented by the formula: $LiPF_a(C_nF_{2n+1})_{6-a}$ (wherein a is an integer of 0 to 5; and n is an integer of 1 to 6) (e.g., $LiPF_4(CF_3)_2$, $LiPF_4(C_2F_5)_2$, $LiPF_4(CF_3SO_2)_2$, $LiPF_4(C_2F_5SO_2)_2$. $LiBF_3CF_3$, $LiBF_3C_2F_5$, $LiBF_3C_3F_7$, $LiBF_2(CF_3)_2$, $LiBF_2(C_2F_5)_2$, $LiBF_2(CF_3SO_2)_2$, and $LiBF_2(C_2F_5SO_2)_2$.

In order to give a low resistance and to achieve an effect of improving characteristics such as high-rate charge and discharge characteristics, high-temperature storage characteristics, and cycle characteristics, particularly preferred among these are $LiPF_6$, $LiBF_4$, $FSO_3Li$, $CF_3SO_3Li$, $LiN(FSO_2)_2$, $LiN(CF_3SO_2)_2$, lithium cyclic 1,2-perfluoroethane disulfonyl imide, lithium cyclic 1,3-perfluoropropane disulfonyl imide, $LiC(FSO_2)_3$, $LiC(CF_3SO_2)_3$, $LiC(C_2F_5SO_2)_3$, lithium bis(oxalato)borate, lithium difluorooxalatoborate, lithium tetrafluorooxalatophosphate, lithium difluorobis(oxalato)phosphate, $LiBF_3CF_3$, $LiBF_3C_2F_5$, $LiPF_3(CF_3)_3$, and $LiPF_3(C_2F_5)_3$.

These lithium salts may be used alone or in combination of two or more. In combination use of two or more thereof, preferred examples thereof include a combination of $LiPF_6$ and $LiBF_4$ and a combination of $LiPF_6$ and $FSO_3Li$, which has an effect of improving the load characteristics and the cycle characteristics.

In this case, $LiBF_4$ or $FSO_3Li$ may be used in any amount that does not significantly impair the effects of the invention in 100% by mass of the whole electrolyte solution. The amount thereof is usually 0.01% by mass or more, preferably 0.5% by mass or more, while usually 30% by mass or less, preferably 15% by mass or less, relative to the electrolyte solution of the invention.

In another example, an inorganic lithium salt and an organic lithium salt are used in combination. Such a combination has an effect of reducing deterioration due to high-temperature storage. The organic lithium salt is preferably $CF_3SO_3Li$, $LiN(FSO_2)_2$, $LiN(FSO_2)(CF_3SO_2)$, $LiN(CF_3SO_2)_2$. $LiN(C_2F_5SO_2)_2$, lithium cyclic 1,2-perfluoroethanedisulfonylimide, lithium cyclic 1,3-perfluoropropanedisulfonylimide, $LiC(FSO_2)_3$, $LiC(CF_3SO_2)_3$. $LiC(C_2F_5SO_2)_3$, lithium bis(oxalato)borate, lithium difluorooxalatoborate, lithium tetrafluorooxalatophosphate, lithium difluorobis(oxalato)phosphate, $LiBF_3CF_3$, $LiBF_3C_2F_5$, $LiPF_3(CF_3)_3$, $LiPF_3(C_2F_5)_3$, or the like. In this case, the proportion of the organic lithium salt is preferably 0.1% by mass or more, particularly preferably 0.5% by mass or more, while preferably 30% by mass or less, particularly preferably 20% by mass or less, in 100% by mass of the whole electrolyte solution.

The lithium salt in the electrolyte solution may have any concentration that does not impair the effects of the invention. In order to make the electric conductivity of the electrolyte solution within a favorable range and to ensure good battery performance, the lithium in the electrolyte solution preferably has a total mole concentration of 0.3 mol/L or higher, more preferably 0.5 mol/L or higher, still more preferably 0.7 mol/L or higher, while preferably 4.0 mol/L or lower, more preferably 2.0 mol/L or lower, still more preferably 1.5 mol/L or lower.

Too low a total mole concentration of lithium may cause insufficient electric conductivity of the electrolyte solution, while too high a concentration may cause a viscosity increase and then reduce the electric conductivity, impairing the battery performance.

The electrolyte salt in the electrolyte solution for an electric double layer capacitor is preferably an ammonium salt.

Examples of the ammonium salt include the following salts (IIa) to (IIe).

(IIa) Tetraalkyl Quaternary Ammonium Salts

Preferred examples thereof include tetraalkyl quaternary ammonium salts represented by the following formula (IIa):

[Chem. 33]

$$R^{2a}-\overset{R^{1a}}{\underset{R^{3a}}{\overset{|}{N^{\oplus}}}}-R^{4a} \quad X^{\ominus} \qquad (IIa)$$

(wherein $R^{1a}$, $R^{2a}$, $R^{3a}$, and $R^{4a}$ are the same as or different from each other, and are each a C1-C6 alkyl group optionally containing an ether bond; and $X^-$ is an anion). In order to improve the oxidation resistance, any or all of the hydrogen atoms in the ammonium salt are also preferably replaced by a fluorine atom and/or a C1-C4 fluorine-containing alkyl group.

Preferred specific examples thereof include tetraalkyl quaternary ammonium salts represented by the following formula (IIa-1):

[Chem. 34]

$$(R^1)_x(R^{2a})_y N^{\oplus} X^{\ominus} \qquad (IIa-1)$$

wherein $R^{1a}$, $R^{2a}$, and $X^-$ are defined in the same manner as described above; x and y are the same as or different from each other, and are each an integer of 0 to 4 with x+y=4, and alkyl ether group-containing trialkyl ammonium salts represented by the following formula (IIa-2):

[Chem. 35]

$$(R^{5a})_3 \overset{\oplus}{N} \quad X^{\ominus} \qquad (IIa-2)$$
$$\underset{|}{(R^{6a})_z-O-R^{7a}}$$

wherein $R^{5a}$ is a C1-C6 alkyl group; $R^{6a}$ is a C1-C6 divalent hydrocarbon group; $R^{7a}$ is a C1-C4 alkyl group; z is 1 or 2; and $X^-$ is an anion.

Introduction of an alkyl ether group enables reduction in viscosity.

The anion $X^-$ may be either an inorganic anion or an organic anion. Examples of the inorganic anion include $AlCl_4^-$, $BF_4^-$, $PF_6^-$, $AsF_6^-$, $TaF_6^-$, $I^-$, and $SbF_6^-$. Examples of the organic anion include a bis(oxalato)borate anion, a difluoro(oxalato)borate anion, a tetrafluoro(oxalato)phosphate anion, a difluorobis(oxalato)phosphate anion, $CF_3COO^-$, $CF_3SI_3^-$, $(CF_3SO_2)_2N^-$, and $(C_2F_5SO_2)_2N^-$.

In order to achieve good oxidation resistance and ionic dissociation, $BF_4^-$, $PF_6^-$, $AsF_6^-$, and $SbF_6^-$ are preferred.

Preferred specific examples of the tetraalkyl quaternary ammonium salts to be used include $Et_4NBF_4$, $Et_4NClO_4$, $Et_4NPF_6$, $Et_4NAsF_6$, $Et_4NSbF_6$, $Et_4NCF_3SO_3$, $Et_4N(CF_3SO_2)_2N$, $Et_4NC_4F_9SO_3$, $Et_3MeNBF_4$, $Et_3MeNClO_4$, $Et_3MeNPF_6$, $Et_3MeNAsF_6$, $Et_3MeNSbF_6$, $Et_3MeNCF_3SO_3$, $Et_3MeN(CF_3SO_2)_2N$, and $Et_3MeNC_4F_9SO_3$. In particular, $Et_4NBF_4$, $Et_4NPF_6$, $Et_4NSbF_6$, $Et_4NAsF_6$, $Et_3MeNBF_4$, and an N,N-diethyl-N-methyl-N-(2-methoxyethyl)ammonium salt may be mentioned as examples.

(IIb) Spirocyclic Bipyrrolidinium Salts

Preferred examples thereof include spirocyclic bipyrrolidinium salts represented by the following formula (IIb-1):

[Chem. 36]

$$\text{(structure with } (R^{9a})_{n2}, (R^{8a})_{n1}, X^{\ominus}\text{)} \qquad (IIb-1)$$

wherein $R^{8a}$ and $R^{9a}$ are the same as or different from each other, and are each a C1-C4 alkyl group; $X^-$ is an anion; n1 is an integer of 0 to 5; and n2 is an integer of 0 to 5, spirocyclic bipyrrolidinium salts represented by the following formula (IIb-2):

[Chem. 37]

$$\text{(structure with } (R^{11a})_{n4}, (R^{10a})_{n3}, X^{\ominus}\text{)} \qquad (IIb-2)$$

wherein $R^{10a}$ and $R^{11a}$ are the same as or different from each other, and are each a C1-C4 alkyl group; $X^-$ is an anion; n3 is an integer of 0 to 5; and n4 is an integer of 0 to 5, and spirocyclic bipyrrolidinium salts represented by the following formula (IIb-3):

[Chem. 38]

$$\text{(structure with } (R^{13a})_{n6}, (R^{12a})_{n5}, X^{\ominus}\text{)} \qquad (IIb-3)$$

wherein $R^{12a}$ and $R^{13a}$ are the same as or different from each other, and are each a C1-C4 alkyl group; $X^-$ is an anion; n5 is an integer of 0 to 5; and n6 is an integer of 0 to 5.

In order to improve the oxidation resistance, any or all of the hydrogen atoms in the spirocyclic bipyrrolidinium salt are also preferably replaced by a fluorine atom and/or a C1-C4 fluorine-containing alkyl group.

Preferred specific examples of the anion $X^-$ are the same as those mentioned for the salts (IIa). In order to achieve good dissociation and a low internal resistance under high voltage, $BF_4^-$, $PF_6^-$, $(CF_3SO_2)_2N^-$, or $(C_2F_5SO_2)_2N^-$ is particularly preferred.

For example, those represented by the following formulae:

[Chem. 39]

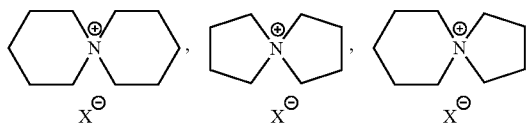

may be mentioned as preferred specific examples of the spirocyclic bipyrrolidinium salts.

These spirocyclic bipyrrolidinium salts are excellent in solubility in a solvent, oxidation resistance, and ion conductivity.

(IIc) Imidazolium Salts

Preferred examples thereof include imidazolium salts represented by the following formula (IIc):

[Chem. 40]

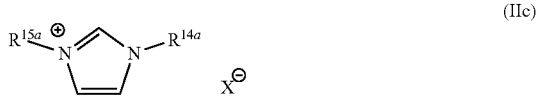

(IIc)

(wherein $R^{14a}$ and $R^{15a}$ are the same as or different from each other, and are each a C1-C6 alkyl group; and $X^-$ is an anion). In order to improve the oxidation resistance, any or all of the hydrogen atoms in the imidazolium salt are also preferably replaced by a fluorine atom and/or a C1-C4 fluorine-containing alkyl group.

Preferred specific examples of the anion $X^-$ are the same as those mentioned for the salts (IIa).

For example, one represented by the following formula:

[Chem. 41]

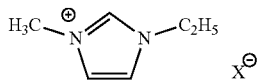

may be mentioned as a preferred specific example thereof.

This imidazolium salt is excellent in that it has low viscosity and good solubility.

(IId) N-Alkylpyridinium Salts

Preferred examples thereof include N-alkylpyridinium salts represented by the following formula (IId):

[Chem. 42]

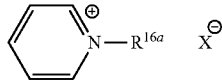

(IId)

(wherein $R^{16a}$ is a C1-C6 alkyl group; and $X^-$ is an anion). In order to improve oxidation resistance, any or all of the hydrogen atoms in the N-alkylpyridinium salt are also preferably replaced by a fluorine atom and/or a C1-C4 fluorine-containing alkyl group.

Preferred specific examples of the anion $X^-$ are the same as those mentioned for the salts (IIa).

For example, those represented by the following formulae:

[Chem. 43]

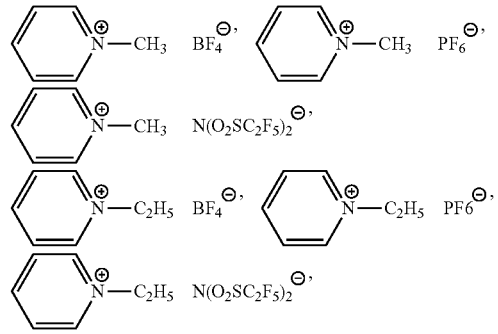

may be mentioned as preferred specific examples thereof.

These N-alkylpyridinium salts are excellent in that they have low viscosity and good solubility.

(IIe) N,N-Dialkylpyrrolidinium Salts

Preferred examples thereof include N,N-dialkylpyrrolidinium salts represented by the following formula (IIe):

[Chem. 44]

(IIe)

wherein $R^{17a}$ and $R^{18a}$ are the same as or different from each other, and are each a C1-C6 alkyl group; and $X^-$ is an anion.

In order to improve the oxidation resistance, any or all of the hydrogen atoms in the N,N-dialkylpyrrolidinium salt are also preferably replaced by a fluorine atom and/or a C1-C4 fluorine-containing alkyl group.

Preferred specific examples of the anion $X^-$ are the same as those mentioned for the salts (IIa).

For example, those represented by the following formulae:

[Chem. 45]

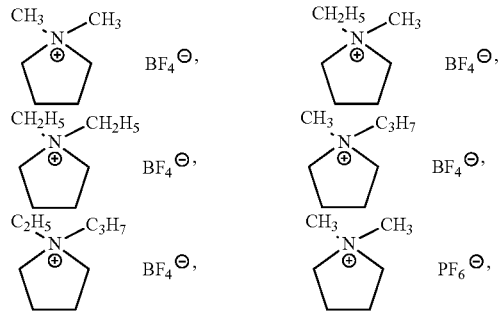

-continued

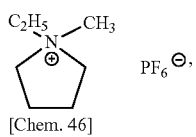

[Chem. 46]

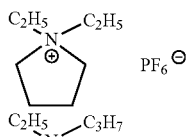

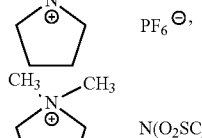

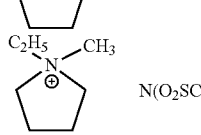

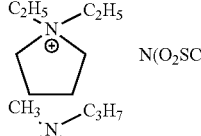

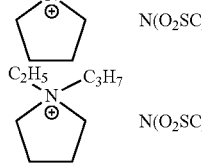

may be mentioned as preferred specific examples thereof.

These N,N-dialkylpyrrolidinium salts are excellent in that they have low viscosity and good solubility.

Preferred among these ammonium salts are those represented by the formula (IIa), (IIb), or (IIc) because they can have good solubility, oxidation resistance, and ion conductivity. More preferred are those represented by the following formulae:

[Chem. 47]

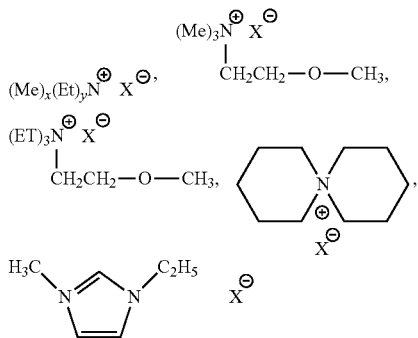

wherein Me is a methyl group; Et is an ethyl group; and $X^-$, x, and y are defined in the same manner as in the formula (IIa-1).

A lithium salt may be used as an electrolyte salt for an electric double layer capacitor. Preferred examples thereof include $LiPF_6$, $LiBF_4$, $LiN(FSO_2)_2$, $LiAsF_6$, $LiSbF_6$, and $LiN(SO_2C_2H_5)_2$.

In order to further increase the capacity, a magnesium salt may be used. Preferred examples of the magnesium salt include $Mg(ClO_4)_2$ and $Mg(OOC_2H_5)_2$.

The ammonium salt serving as an electrolyte salt is preferably used at a concentration of 0.7 mol/L or higher. The ammonium salt at a concentration lower than 0.7 mol/L may cause not only poor low-temperature characteristics but also high initial internal resistance. The concentration of the electrolyte salt is more preferably 0.9 mol/L or higher.

In order to achieve good low-temperature characteristics, the upper limit of the concentration is preferably 2.0 mol/L or lower, more preferably 1.5 mol/L or lower.

In order to achieve excellent low-temperature characteristics, the ammonium salt which is triethyl methyl ammonium tetrafluoroborate ($TEMABF_4$) is preferably used at a concentration of 0.7 to 1.5 mol/L.

Spirobipyrrolidinium tetrafluoroborate ($SBPBF_4$) is preferably used at a concentration of 0.7 to 2.0 mol/L.

The electrolyte solution of the invention may contain at least one selected from the group consisting of nitrile compounds represented by any of the following formulae (1a), (1b), and (1c):

[Chem. 48]

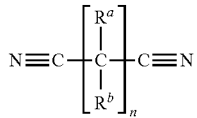

(1a)

(wherein $R^a$ and $R^b$ are each individually a hydrogen atom, a cyano group (CN), a halogen atom, an alkyl group, or a group obtained by replacing at least one hydrogen atom of an alkyl group with a halogen atom; and n is an integer of 1 to 10);

[Chem. 49]

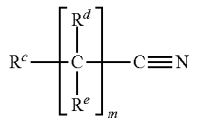

(1b)

(wherein $R^c$ is a hydrogen atom, a halogen atom, an alkyl group, a group obtained by replacing at least one hydrogen atom of an alkyl group with a halogen atom, or a group represented by $NC-R^{c1}-X^{c1}-$ (wherein $R^{c1}$ is an alkylene group; and $X^{c1}$ is an oxygen atom or a sulfur atom); $R^d$ and $R^e$ are each individually a hydrogen atom, a halogen atom, an alkyl group, or a group obtained by replacing at least one hydrogen atom of an alkyl group with a halogen atom; and m is an integer of 1 to 10); and

[Chem. 50]

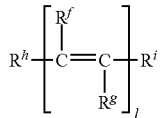

(1c)

(wherein $R^f$, $R^g$, $R^h$, and $R^i$ are each individually a group containing a cyano group (CN), a hydrogen atom (H), a halogen atom, an alkyl group, or a group obtained by replacing at least one hydrogen atom of an alkyl group with a halogen atom; at least one of $R^f$, $R^g$, $R^h$, or $R^i$ is a group containing a cyano group; and l is an integer of 1 to 3).

This can improve the high-temperature storage characteristics of an electrochemical device. The nitrile compounds may be used alone or in any combination of two or more at any ratio.

In the formula (1a), $R^a$ and $R^b$ are each individually a hydrogen atom, a cyano group (CN), a halogen atom, an alkyl group, or a group obtained by replacing at least one hydrogen atom of an alkyl group with a halogen atom.

Examples of the halogen atom include a fluorine atom, a chlorine atom, a bromine atom, and an iodine atom. Preferred among these is a fluorine atom.

The alkyl group is preferably a C1-C5 alkyl group. Specific examples of the alkyl group include a methyl group, an ethyl group, a propyl group, an isopropyl group, a butyl group, an isobutyl group, and a tert-butyl group.

Examples of the group obtained by replacing at least one hydrogen atom of an alkyl group with a halogen atom include groups in which at least one hydrogen atom of the above alkyl group with the above halogen atom.

When $R^a$ and $R^b$ are alkyl groups or groups obtained by replacing at least one hydrogen atom of an alkyl group with a halogen atom, $R^a$ and $R^b$ may be bonded to each other to form a ring structure (e.g., cyclohexane ring).

$R^a$ and $R^b$ are preferably hydrogen atoms or alkyl groups.

In the formula (1a), n is an integer of 1 to 10. When n is 2 or greater, all of n $R^a$s may be the same as each other, or at least some of them may be different from each other. The same applies to $R^b$. In the formula, n is preferably an integer of 1 to 7, more preferably an integer of 2 to 5.

The nitrile compound represented by the formula (1a) is preferably a dinitrile or a tricarbonitrile.

Specific examples of the dinitrile include malononitrile, succinonitrile, glutaronitrile, adiponitrile, pimelonitrile, suberonitrile, azelanitrile, sebaconitrile, undecanedinitrile, dodecanedinitrile, methyl malononitrile, ethyl malononitrile, isopropyl malononitrile, tert-butyl malononitrile, methyl succinonitrile, 2,2-dimethyl succinonitrile, 2,3-dimethyl succinonitrile, 2,3,3-trimethyl succinonitrile, 2,2,3,3-tetramethyl succinonitrile, 2,3-diethyl-2,3-dimethyl succinonitrile, 2,2-diethyl-3,3-dimethyl succinonitrile, bicyclohexyl-1,1-dicarbonitrile, bicyclohexyl-2,2-dicarbonitrile, bicyclohexyl-3,3-dicarbonitrile, 2,5-dimethyl-2,5-hexanedicarbonitrile, 2,3-diisobutyl-2,3-dimethyl succinonitrile, 2,2-diisobutyl-3,3-dimethyl succinonitrile, 2-methyl glutaronitrile, 2,3-dimethyl glutaronitrile, 2,4-dimethyl glutaronitrile, 2,2,3,3-tetramethyl glutaronitrile, 2,2,4,4-tetramethyl glutaronitrile, 2,2,3,4-tetramethyl glutaronitrile, 2,3,3,4-tetramethyl glutaronitrile, 1,4-dicyanopentane, 2,6-dicyanoheptane, 2,7-dicyanooctane, 2,8-dicyanononane, and 1,6-dicyanodecane. Particularly preferred among these are succinonitrile, glutaronitrile, and adiponitrile.

Specific examples of the tricarbonitrile include pentanetricarbonitrile, propanetricarbonitrile, 1,3,5-hexanetricarbonitrile, 1,3,5-cyclohexanetricarbonitrile, 1,3,6-hexanetricarbonitrile, heptanetricarbonitrile, 1,2,3-propanetricarbonitrile, and 1,3,5-pentanetricarbonitrile. Particularly preferred are 1,3,5-hexanetricarbonitrile and 1,3,6-hexanetricarbonitrile.

In the formula (1b), $R^c$ is a hydrogen atom, a halogen atom, an alkyl group, a group obtained by replacing at least one hydrogen atom of an alkyl group with a halogen atom, or a group represented by NC—$R^{c1}$—$X^{c1}$— (wherein $R^{c1}$ is an alkylene group; and $X^{c1}$ is an oxygen atom or a sulfur atom), and $R^d$ and $R^e$ are each individually a hydrogen atom, a halogen atom, an alkyl group, or a group obtained by replacing at least one hydrogen atom of an alkyl group with a halogen atom.

Examples of the halogen atom, the alkyl group, and the group obtained by replacing at least one hydrogen atom of an alkyl group with a halogen atom include those mentioned as examples for the formula (1a).

$R^{c1}$ in NC—$R^{c1}$—$X^{c1}$— is an alkylene group. The alkylene group is preferably a C1-C3 alkylene group.

$R^c$, $R^d$, and $R^e$ are preferably each individually a hydrogen atom, a halogen atom, an alkyl group, or a group obtained by replacing at least one hydrogen atom of an alkyl group with a halogen atom.

At least one of $R^c$, $R^d$, or $R^e$ is preferably a halogen atom or a group obtained by replacing at least one hydrogen atom of an alkyl group with a halogen atom, more preferably a fluorine atom or a group obtained by replacing at least one hydrogen atom of an alkyl group with a fluorine atom.

When $R^d$ and $R^e$ are alkyl groups or groups obtained by replacing at least one hydrogen atom of an alkyl group with a halogen atom, $R^d$ and $R^e$ may be bonded to each other to form a ring structure (e.g., cyclohexane ring).

In the formula (1b), m is an integer of 1 to 10. When m is 2 or greater, all of m $R^d$s may be the same as each other, or at least some of them may be different from each other. The same applies to $R^e$. In the formula, m is preferably an integer of 2 to 7, more preferably an integer of 2 to 5.

Examples of the nitrile compound represented by the formula (1b) include acetonitrile, propionitrile, butyronitrile, isobutyronitrile, valeronitrile, isovaleronitrile, lauronitrile, 2-methyl butyronitrile, trimethyl acetonitrile, hexanenitrile, cyclopentanecarbonitrile, cyclohexanecarbonitrile, fluoroacetonitrile, difluoroacetonitrile, trifluoroacetonitrile, 2-fluoropropionitrile, 3-fluoropropionitrile, 2,2-difluoropropionitrile, 2,3-difluoropropionitrile, 3,3-difluoropropionitrile, 2,2,3-trifluoropropionitrile, 3,3,3-trifluoropropionitrile, 3,3'-oxydipropionitrile, 3,3'-thiodipropionitrile, and pentafluoropropionitrile. Particularly preferred among these is 3,3,3-trifluoropropionitrile.

In the formula (1c), $R^f$, $R^g$, $R^h$, and $R^i$ are each individually a group containing a cyano group (CN), a hydrogen atom, a halogen atom, an alkyl group, or a group obtained by replacing at least one hydrogen atom of an alkyl group with a halogen atom.

Examples of the halogen atom, the alkyl group, and the group obtained by replacing at least one hydrogen atom of an alkyl group with a halogen atom include those mentioned as examples for the formula (1a).

Examples of the group containing a cyano group include a cyano group and groups obtained by replacing at least one hydrogen atom of an alkyl group with a cyano group. Examples of the alkyl group in this case include those mentioned as examples for the formula (1a).

At least one of $R^f$, $R^g$, $R^h$, or $R^i$ is a group containing a cyano group. At least two selected from $R^f$, $R^g$, $R^h$, and $R^i$ are preferably groups containing a cyano group. More preferably, $R^h$ and $R^i$ are groups containing a cyano group. When $R^h$ and $R^i$ are groups containing a cyano group, $R^f$ and $R^g$ are preferably hydrogen atoms.

In the formula (1c), l is an integer of 1 to 3. When l is 2 or greater, all of l $R^f$s may be the same as each other, or at least some of them may be different from each other. The same applies to $R^g$. Preferably, l is an integer of 1 or 2.

Examples of the nitrile compound represented by the formula (1c) include 3-hexenedinitrile, mucononitrile, maleonitrile, fumaronitrile, acrylonitrile, methacrylonitrile, crotononitrile, 3-methyl crotononitrile, 2-methyl-2-butenenitrile, 2-pentenenitrile, 2-methyl-2-pentenenitrile, 3-methyl-2-pentenenitrile, and 2-hexenenitrile. Preferred are 3-hexenedinitrile and mucononitrile, particularly preferred is 3-hexenedinitrile.

The nitrile compound is preferably contained in an amount of 0.2 to 7% by mass relative to the electrolyte solution. This can further improve the high-temperature storage characteristics and the safety of an electrochemical device at high voltage. The lower limit of the sum of the amounts of the nitrile compounds is more preferably 0.3% by mass, still more preferably 0.5% by mass. The upper limit thereof is more preferably 5% by mass, still more preferably 2% by mass, particularly preferably 0.5% by mass.

The electrolyte solution of the invention may further contain a compound (B) represented by the formula (B).

The formula (B) is as follows.

[Chem. 51]

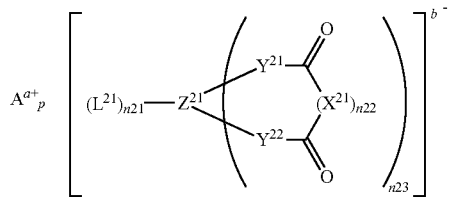

In the formula, $A^{a+}$ is a metal ion, a hydrogen ion, or an onium ion;

a is an integer of 1 to 3;

b is an integer of 1 to 3;

p is b/a;

$n^{23}$ is an integer of 1 to 4;

$n^{21}$ is an integer of 0 to 8;

$n^{22}$ is 0 or 1;

$Z^{21}$ is a transition metal or an element in group III, group IV, or group V of the Periodic Table;

$X^{21}$ is O, S, a C1-C10 alkylene group, a C1-C10 halogenated alkylene group, a C6-C20 arylene group, or a C6-C20 halogenated arylene group, with the alkylene group, the halogenated alkylene group, the arylene group, and the halogenated arylene group each optionally containing a substituent and/or a hetero atom in the structure thereof, and when $n^{22}$ is 1 and $n^{23}$ is 2 to 4, $n^{23}$ $X^{21}$s optionally bind to each other;

$L^{21}$ is a halogen atom, a cyano group, a C1-C10 alkyl group, a C1-C10 halogenated alkyl group, a C6-C20 aryl group, a C6-C20 halogenated aryl group, or —$Z^{23}Y^{23}$, with the alkylene group, the halogenated alkylene group, the arylene group, and the halogenated arylene group each optionally containing a substituent and/or a hetero atom in the structure thereof, and when $n^{21}$ is 2 to 8, $n^{21}$ $L^{21}$s optionally bind to each other to form a ring;

$Y^{21}$, $Y^{22}$, and $Z^{23}$ are each individually O, S, $NY^{24}$, a hydrocarbon group, or a fluorinated hydrocarbon group;

$Y^{23}$ and $Y^{24}$ are each individually H, F, a C1-C10 alkyl group, a C1-C10 halogenated alkyl group, a C6-C20 aryl group, or a C6-C20 halogenated aryl group, with the alkyl group, the halogenated alkyl group, the aryl group, and the halogenated aryl group each optionally containing a substituent and/or a hetero atom in the structure thereof, and when multiple $Y^{23}$s or multiple $Y^{24}$s are present, they optionally bind to each other to form a ring.

Examples of $A^{a+}$ include a lithium ion, a sodium ion, a potassium ion, a magnesium ion, a calcium ion, a barium ion, a caesium ion, a silver ion, a zinc ion, a copper ion, a cobalt ion, an iron ion, a nickel ion, a manganese ion, a titanium ion, a lead ion, a chromium ion, a vanadium ion, a ruthenium ion, an yttrium ion, lanthanoid ions, actinoid ions, a tetrabutyl ammonium ion, a tetraethyl ammonium ion, a tetramethyl ammonium ion, a triethyl methyl ammonium ion, a triethyl ammonium ion, a pyridinium ion, an imidazolium ion, a hydrogen ion, a tetraethyl phosphonium ion, a tetramethyl phosphonium ion, a tetraphenyl phosphonium ion, a triphenyl sulfonium ion, and a triethyl sulfonium ion.

In applications such as electrochemical devices, $A^{a+}$ is preferably a lithium ion, a sodium ion, a magnesium ion, a tetraalkyl ammonium ion, or a hydrogen ion, particularly preferably a lithium ion. The valence a of the cation $A^{a+}$ is an integer of 1 to 3. If the valence a is greater than 3, the crystal lattice energy is high and the compound (B) has difficulty in dissolving in a solvent. Thus, the valence a is more preferably 1 when good solubility is needed. The valence b of the anion is also an integer of 1 to 3, particularly preferably 1. The constant p that represents the ratio between the cation and the anion is naturally defined by the ratio b/a between the valences a and b thereof.

Next, the ligands in the formula (B) are described. Herein, organic or inorganic groups binding to $Z^{21}$ in the formula (B) are referred to as ligands.

$Z^{21}$ is preferably Al, B, V, Ti, Si, Zr, Ge, Sn, Cu, Y, Zn, Ga, Nb, Ta, Bi, P, As, Sc, Hf, or Sb, more preferably Al, B, or P.

$X^{21}$ is O, S, a C1-C10 alkylene group, a C1-C10 halogenated alkylene group, a C6-C20 arylene group, or a C6-C20 halogenated arylene group. These alkylene groups and arylene groups each may have a substituent and/or a hetero atom in the structure. Specifically, instead of a hydrogen atom in the alkylene group or the arylene group, the structure may have a halogen atom, a linear or cyclic alkyl group, an aryl group, an alkenyl group, an alkoxy group, an aryloxy group, a sulfonyl group, an amino group, a cyano group, a carbonyl group, an acyl group, an amide group, or a hydroxy group as a substituent; or, instead of a carbon atom in the alkylene or the arylene, the structure may have nitrogen, sulfur, or oxygen introduced therein. When $n^{22}$ is 1 and $n^{23}$ is 2 to 4, $n^{23}$ $X^{21}$s may bind to each other. One such example is a ligand such as ethylenediaminetetraacetic acid.

$L^{21}$ is a halogen atom, a cyano group, a C1-C10 alkyl group, a C1-C10 halogenated alkyl group, a C6-C20 aryl group, a C6-C20 halogenated aryl group, or —$Z^{23}Y^{23}$ ($Z^{23}$ and $Y^{23}$ will be described later). Similar to $X^{21}$, the alkyl groups and the aryl groups each may have a substituent and/or a hetero atom in the structure, and when $n^{21}$ is 2 to 8, $n^{21}$ $L^{21}$s may bind to each other to form a ring. Ln is preferably a fluorine atom or a cyano group. This is because a fluorine atom can improve the solubility and the degree of dissociation of a salt of an anion compound, thereby improving the ion conductivity. This is also because a fluorine atom can improve the oxidation resistance, reducing occurrence of side reactions.

$Y^{21}$, $Y^{22}$, and $Z^{23}$ are each individually O, S, $NY^{24}$, a hydrocarbon group, or a fluorinated hydrocarbon group. $Y^{21}$ and $Y^{22}$ are each preferably O, S, or $NY^{24}$, more preferably O. The compound (B) characteristically has a bond between $Y^{21}$ and $Z^{21}$ and a bond between $Y^{22}$ and $Z^{21}$ in the same ligand. Such a ligand forms a chelate structure with $Z^{21}$. The effect of this chelate improves the heat resistance, the chemical stability, and the hydrolysis resistance of this compound. The constant $n^{22}$ of the ligand is 0 or 1. In particular, $n^{22}$ is preferably 0 because the chelate ring becomes a five-membered ring, leading to the most strongly exerted chelate effect and improved stability.

The term "fluorinated hydrocarbon group" as used herein means a hydrocarbon group in which at least one hydrogen atom is replaced by a fluorine atom.

$Y^{23}$ and $Y^{24}$ are each individually H, F, a C1-C10 alkyl group, a C1-C10 halogenated alkyl group, a C6-C20 aryl group, or a C6-C20 halogenated aryl group. These alkyl groups and aryl groups each may contain a substituent or a hetero atom in the structure. When multiple $Y^{23}$s or multiple $Y^{24}$s are present, they may bind to each other to form a ring.

The constant $n^{23}$ relating to the number of the aforementioned ligands is an integer of 1 to 4, preferably 1 or 2, more preferably 2. The constant $n^{21}$ relating to the number of the aforementioned ligands is an integer of 0 to 8, preferably an integer of 0 to 4, more preferably 0, 2, or 4. In addition, when $n^{23}$ is 1, $n^{21}$ is preferably 2; and when $n^{23}$ is 2, $n^{21}$ is preferably 0.

In the formula (B), the alkyl group, the halogenated alkyl group, the aryl group, and the halogenated aryl group include those having any other functional groups such as branches, hydroxy groups, and ether bonds.

The compound (B) is preferably a compound represented by the following formula:

[Chem. 52]

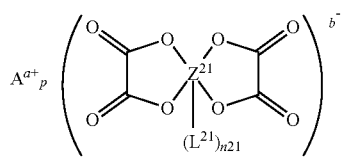

(wherein $A^{a+}$, a, b, p, $n^{21}$, $Z^{21}$, and $L^{21}$ are defined in the same manner as described above), or a compound represented by the following formula:

[Chem. 53]

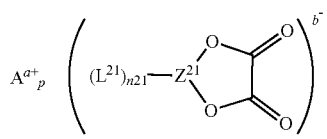

(wherein $A^{a+}$, a, b, p, $n^{21}$, $Z^{21}$, and $L^{21}$ are defined in the same manner as described above).

The compound (B) may be a lithium (oxalato)borate salt. Examples thereof include lithium bis(oxalato)borate (LI-BOB) represented by the following formula:

[Chem. 54]

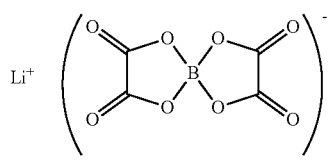

and lithium difluoro(oxalato)borate (LIDFOB) represented by the following formula:

[Chem. 55]

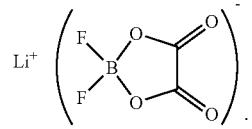

Examples of the compound (B) also include lithium difluoro(oxalato)phosphanite (LIDFOP) represented by the following formula:

[Chem. 56]

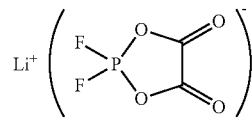

lithium tetrafluoro(oxalato)phosphanite (LITFOP) represented by the following formula:

[Chem. 57]

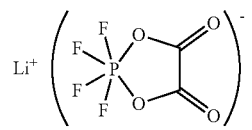

and lithium bis(oxalato)difluorophosphanite represented by the following formula:

[Chem. 58]

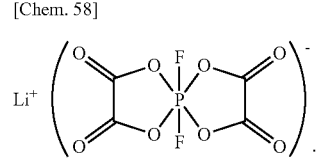

In order to achieve much better cycle characteristics, the compound (B) is preferably contained in an amount of 0.001% by mass or more, more preferably 0.01% by mass or more, while preferably 10% by mass or less, more preferably 3% by mass or les, relative to the solvent.

The electrolyte solution of the invention may include polyethylene oxide that has a weight average molecular weight of 2000 to 4000 and has —OH, —OCOOH, or —COOH at an end.

The presence of such a compound can improve the stability at the interfaces with the respective electrodes, improving the characteristics of an electrochemical device.

Examples of the polyethylene oxide include polyethylene oxide monool, polyethylene oxide carboxylate, polyethylene oxide diol, polyethylene oxide dicarboxylate, polyethylene oxide triol, and polyethylene oxide tricarboxylate. These may be used alone or in combination of two or more.

In order to achieve better characteristics of an electrochemical device, preferred are a mixture of polyethylene oxide monool and polyethylene oxide diol and a mixture of polyethylene carboxylate and polyethylene dicarboxylate.

The polyethylene oxide having too small a weight average molecular weight may be easily oxidatively decomposed. The weight average molecular weight is more preferably 3000 to 4000.

The weight average molecular weight can be determined by gel permeation chromatography (GPC) in polystyrene equivalent.

The amount of the polyethylene oxide is preferably $1 \times 10^{-6}$ to $1 \times 10^{-2}$ mol/kg in the electrolyte solution. Too large an amount of the polyethylene oxide may cause poor characteristics of an electrochemical device.

The amount of the polyethylene oxide is more preferably $5 \times 10^{-6}$ mol/kg or more.

The electrolyte solution of the invention may further contain other components such as an unsaturated cyclic carbonate, an overcharge inhibitor, and a known different aid. This can reduce impairment of the characteristics of an electrochemical device.

Examples of the unsaturated cyclic carbonate include vinylene carbonates, ethylene carbonates substituted with a substituent that contains an aromatic ring, a carbon-carbon double bond, or a carbon-carbon triple bond, phenyl carbonates, vinyl carbonates, allyl carbonates, and catechol carbonates.

Examples of the vinylene carbonates include vinylene carbonate, methyl vinylene carbonate, 4,5-dimethyl vinylene carbonate, phenyl vinylene carbonate, 4,5-diphenyl vinylene carbonate, vinyl vinylene carbonate, 4,5-divinyl vinylene carbonate, allyl vinylene carbonate, 4,5-diallyl vinylene carbonate, 4-fluorovinylene carbonate, 4-fluoro-5-methyl vinylene carbonate, 4-fluoro-5-phenyl vinylene carbonate, 4-fluoro-5-vinyl vinylene carbonate, and 4-allyl-5-fluorovinylene carbonate.

Specific examples of the ethylene carbonates substituted with a substituent that contains an aromatic ring, a carbon-carbon double bond, or a carbon-carbon triple bond include vinyl ethylene carbonate, 4,5-divinyl ethylene carbonate, 4-methyl-5-vinyl ethylene carbonate, 4-allyl-5-vinyl ethylene carbonate, ethynyl ethylene carbonate, 4,5-diethynyl ethylene carbonate, 4-methyl-5-ethynyl ethylene carbonate, 4-vinyl-5-ethynyl ethylene carbonate, 4-allyl-5-ethynyl ethylene carbonate, phenyl ethylene carbonate, 4,5-diphenyl ethylene carbonate, 4-phenyl-5-vinyl ethylene carbonate, 4-allyl-5-phenyl ethylene carbonate, allyl ethylene carbonate, 4,5-diallyl ethylene carbonate, 4-methyl-5-allyl ethylene carbonate, 4-methylene-1,3-dioxolan-2-one, and 4,5-dimethylene-1,3-dioxolan-2-one.

The unsaturated cyclic carbonate is preferably vinylene carbonate, methyl vinylene carbonate, 4,5-dimethyl vinylene carbonate, vinyl vinylene carbonate, 4,5-vinyl vinylene carbonate, allyl vinylene carbonate, 4,5-diallyl vinylene carbonate, vinyl ethylene carbonate, 4,5-divinyl ethylene carbonate, 4-methyl-5-vinyl ethylene carbonate, allyl ethylene carbonate, 4,5-diallyl ethylene carbonate, 4-methyl-5-allyl ethylene carbonate, 4-allyl-5-vinyl ethylene carbonate, ethynyl ethylene carbonate, 4,5-diethynyl ethylene carbonate, 4-methyl-5-ethynyl ethylene carbonate, and 4-vinyl-5-ethynyl ethylene carbonate. In order to form a more stable interface protecting film, particularly preferred are vinylene carbonate, vinyl ethylene carbonate, and ethynyl ethylene carbonate.

The unsaturated cyclic carbonate may have any molecular weight that does not significantly impair the effects of the invention. The molecular weight is preferably 80 or higher and 250 or lower. The unsaturated cyclic carbonate having a molecular weight within this range can easily ensure its solubility in the electrolyte solution and can easily lead to sufficient achievement of the effects of the invention. The molecular weight of the unsaturated cyclic carbonate is more preferably 85 or higher, while more preferably 150 or lower.

The unsaturated cyclic carbonate may be produced by any production method, and may be produced by a known method selected as appropriate.

The unsaturated cyclic carbonates may be used alone or in any combination of two or more at any ratio.

The unsaturated cyclic carbonate may be contained in any amount that does not significantly impair the effects of the invention. The amount of the unsaturated cyclic carbonate is preferably 0.001% by mass or more, more preferably 0.01% by mass or more, still more preferably 0.1% by mass or more, of 100% by mass of the solvent in the invention. The amount is preferably 5% by mass or less, more preferably 4% by mass or less, still more preferably 3% by mass or less. The unsaturated cyclic carbonate in an amount within the above range allows an electrochemical device containing the electrolyte solution to easily exhibit an effect of improving the cycle characteristics, and can easily avoid a situation with reduced high-temperature storage characteristics, generation of a large amount of gas, and a reduced discharge capacity retention.

In addition to the aforementioned non-fluorinated unsaturated cyclic carbonates, a fluorinated unsaturated cyclic carbonate may also suitably be used as an unsaturated cyclic carbonate.

The fluorinated unsaturated cyclic carbonate is a cyclic carbonate containing an unsaturated bond and a fluorine atom. The number of fluorine atoms in the fluorinated unsaturated cyclic carbonate may be any number that is 1 or greater. The number of fluorine atoms is usually 6 or smaller, preferably 4 or smaller, most preferably 1 or 2.

Examples of the fluorinated unsaturated cyclic carbonate include fluorinated vinylene carbonate derivatives and fluorinated ethylene carbonate derivatives substituted with a substituent containing an aromatic ring or a carbon-carbon double bond.

Examples of the fluorinated vinylene carbonate derivatives include 4-fluorovinylene carbonate, 4-fluoro-5-methyl vinylene carbonate, 4-fluoro-5-phenyl vinylene carbonate, 4-allyl-5-fluorovinylene carbonate, and 4-fluoro-5-vinyl vinylene carbonate.

Examples of the fluorinated ethylene carbonate derivatives substituted with a substituent containing an aromatic ring or a carbon-carbon double bond include 4-fluoro-4-vinyl ethylene carbonate, 4-fluoro-4-allyl ethylene carbonate, 4-fluoro-5-vinyl ethylene carbonate, 4-fluoro-5-allyl ethylene carbonate, 4,4-difluoro-4-vinyl ethylene carbonate, 4,4-difluoro-4-allyl ethylene carbonate, 4,5-difluoro-4-vinyl ethylene carbonate, 4,5-difluoro-4-allyl ethylene carbonate, 4-fluoro-4,5-divinyl ethylene carbonate, 4-fluoro-4,5-diallyl ethylene carbonate, 4,5-difluoro-4,5-divinyl ethylene carbonate, 4,5-difluoro-4,5-diallyl ethylene carbonate, 4-fluoro-4-phenyl ethylene carbonate, 4-fluoro-5-phenyl ethylene carbonate, 4,4-difluoro-5-phenyl ethylene carbonate, and 4,5-difluoro-4-phenyl ethylene carbonate.

In order to form a stable interface protecting film, more preferred as the fluorinated unsaturated cyclic carbonate are 4-fluorovinylene carbonate, 4-fluoro-5-methyl vinylene carbonate, 4-fluoro-5-vinyl vinylene carbonate, 4-allyl-5-fluorovinylene carbonate, 4-fluoro-4-vinyl ethylene carbonate, 4-fluoro-4-allyl ethylene carbonate, 4-fluoro-5-vinyl ethylene carbonate, 4-fluoro-5-allyl ethylene carbonate, 4,4-difluoro-4-vinyl ethylene carbonate, 4,4-difluoro-4-allyl ethylene carbonate, 4,5-difluoro-4-vinyl ethylene carbonate, 4,5-difluoro-4-allyl ethylene carbonate, 4-fluoro-4,5-divinyl ethylene carbonate, 4-fluoro-4,5-diallyl ethylene carbonate, 4,5-difluoro-4,5-divinyl ethylene carbonate, and 4,5-difluoro-4,5-diallyl ethylene carbonate.

The fluorinated unsaturated cyclic carbonate may have any molecular weight that does not significantly impair the effects of the invention. The molecular weight is preferably 50 or higher and 250 or lower. The fluorinated unsaturated cyclic carbonate having a molecular weight within this range can easily ensure the solubility of the fluorinated unsaturated cyclic carbonate in the electrolyte solution.

The fluorinated unsaturated cyclic carbonate may be produced by any method, and may be produced by any known method selected as appropriate. The molecular weight is more preferably 100 or higher and more preferably 200 or lower.

The fluorinated unsaturated cyclic carbonates may be used alone or in any combination of two or more at any ratio. The fluorinated unsaturated cyclic carbonate may be contained in any amount that does not significantly impair the effects of the invention. The amount of the fluorinated unsaturated cyclic carbonate is usually preferably 0.01% by mass or more, more preferably 0.1% by mass or more, still more preferably 0.2% by mass or more, while preferably 5% by mass or less, more preferably 4% by mass or less, still more preferably 3% by mass or less, of 100% by mass of the electrolyte solution. The fluorinated unsaturated cyclic carbonate in an amount within this range allows an electrochemical device containing the electrolyte solution to exhibit an effect of sufficiently improving the cycle characteristics and can easily avoid the situation with reduced high-temperature storage characteristics, generation of a large amount of gas, and a reduced discharge capacity retention.

In order to effectively reduce burst or combustion of batteries in case of overcharge, for example, of an electrochemical device containing the electrolyte solution, the electrolyte solution of the invention may contain an overcharge inhibitor.

Examples of the overcharge inhibitor include aromatic compounds such as biphenyl, alkyl biphenyl, terphenyl, partially hydrogenated terphenyl, cyclohexyl benzene, t-butyl benzene, t-amyl benzene, diphenyl ether, and dibenzofuran; partially fluorinated aromatic compounds such as 2-fluorobiphenyl, o-cyclohexyl fluorobenzene, and p-cyclohexyl fluorobenzene; and fluoroanisole compounds such as 2,4-difluoroanisole, 2,5-difluoroanisole, 2,6-difluoroanisole, and 3,5-difluoroanisole. Preferred are aromatic compounds such as biphenyl, alkyl biphenyl, terphenyl, partially hydrogenated terphenyl, cyclohexyl benzene, t-butyl benzene, t-amyl benzene, diphenyl ether, and dibenzofuran. These compounds may be used alone or in combination of two or more. For combination use of two or more compounds, in order to achieve good balance between the overcharge inhibiting characteristics and the high-temperature storage characteristics, preferred is a combination of cyclohexyl benzene and t-butyl benzene or t-amyl benzene, or a combination of at least one oxygen-free aromatic compound selected from biphenyl, alkyl biphenyl, terphenyl, partially hydrogenated terphenyl, cyclohexyl benzene, t-butyl benzene, t-amyl benzene, and the like and at least one oxygen-containing aromatic compound selected from diphenyl ether, dibenzofuran, and the like.

The electrolyte solution of the invention may further contain a known different aid. Examples of the different aid include carbonate compounds such as erythritan carbonate, spiro-bis-dimethylene carbonate, and methoxyethyl-methyl carbonate; carboxylic anhydrides such as succinic anhydride, glutaric anhydride, maleic anhydride, citraconic anhydride, glutaconic anhydride, itaconic anhydride, diglycolic anhydride, cyclohexanedicarboxylic anhydride, cyclopentanetetracarboxylic dianhydride, and phenylsuccinic anhydride; Spiro compounds such as 2,4,8,10-tetraoxaspiro[5.5]undecane and 3,9-divinyl-2,4,8,10-tetraoxaspiro[5.5]undecane; sulfur-containing compounds such as ethylene sulfite, 1,3-propanesultone, 1-fluoro-1,3-propanesultone, 2-fluoro-1,3-propanesultone, 3-fluoro-1,3-propanesultone, 1-propene-1,3-sultone, 1-fluoro-1-propene-1,3-sultone, 2-fluoro-1-propene-1,3-sultone, 3-fluoro-1-propene-1,3-sultone, 1,4-butanesultone, 1-butene-1,4-sultone, 3-butene-1,4-sultone, methyl fluorosulfonate, ethyl fluorosulfonate, methyl methanesulfonate, ethyl methanesulfonate, busulfan, sulfolene, diphenyl sulfone, N,N-dimethylmethanesulfonamide, N,N-diethylmethanesulfonamide, methyl vinyl sulfonate, ethyl vinyl sulfonate, allyl vinyl sulfonate, propargyl vinyl sulfonate, methyl allyl sulfonate, ethyl allyl sulfonate, allyl allyl sulfonate, propargyl allyl sulfonate, and 1,2-bis(vinylsulfonyloxy)ethane; nitrogen-containing compounds such as 1-methyl-2-pyrrolidinone, 1-methyl-2-piperidone, 3-methyl-2-oxazolidinone, 1,3-dimethyl-2-imidazolidinone, and N-methylsuccinimide; phosphorus-containing compounds such as trimethyl phosphite, triethyl phosphite, triphenyl phosphite, trimethyl phosphate, triethyl phosphate, triphenyl phosphate, dimethyl methyl phosphonate, diethyl ethyl phosphonate, dimethyl vinyl phosphonate, diethyl vinyl phosphonate, ethyl diethyl phosphonoacetate, methyl dimethyl phosphinate, ethyl diethyl phosphinate, trimethylphosphine oxide, and triethylphosphine oxide; hydrocarbon compounds such as heptane, octane, nonane, decane, and cycloheptane; and fluorine-containing aromatic compounds such as fluorobenzene, difluorobenzene, hexafluorobenzene, and benzotrifluoride. These compounds may be used alone or in combination of two or more. These aids can improve the capacity retention characteristics and the cycle characteristics after high-temperature storage.

The different aid may be used in any amount that does not significantly impair the effects of the invention. The amount of the different aid is preferably 0.01% by mass or more and 5% by mass or less in 100% by mass of the electrolyte solution. The different aid in an amount within this range can easily sufficiently exhibit the effects thereof and can easily avoid the situation with reduction in battery characteristics such as high-load discharge characteristics. The amount of the different aid is more preferably 0.1% by mass or more, still more preferably 0.2% by mass or more, while more preferably 3% by mass or less, still more preferably 1% by mass or less.

The electrolyte solution of the invention may further contain any of additives such as a cyclic carboxylate, an ether compound, a nitrogen-containing compound, a boron-containing compound, an organosilicon-containing compound, a fireproof agent (flame retardant), a surfactant, an additive for increasing the permittivity, and an improver for cycle characteristics or rate characteristics, to the extent that does not impair the effects of the invention.

Examples of the cyclic carboxylate include those having a carbon number of 3 to 12 in total in the structural formula. Specific examples thereof include gamma-butyrolactone, gamma-valerolactone, gamma-caprolactone, and epsilon-caprolactone. In order to improve the characteristics of an electrochemical device owing to improvement in the degree of dissociation of lithium ions, gamma-butyrolactone is particularly preferred.

In general, the amount of the cyclic carboxylate as an additive is preferably 0.1% by mass or more, more preferably 1% by mass or more, in 100% by mass of the electrolyte solution. The cyclic carboxylate in an amount within this range can easily improve the electric conductivity of the electrolyte solution, improving the large-current discharge characteristics of an electrochemical device. The amount of the cyclic carboxylate is also preferably 10% by mass or less, more preferably 5% by mass or less. Such an upper limit may allow the electrolyte solution to have a viscosity within an appropriate range, may make it possible to avoid a reduction in the electric conductivity, may reduce an increase in the resistance of the negative electrode, and may allow the electrochemical device to have large-current discharge characteristics within a favorable range.

The cyclic carboxylate to be suitably used may also be a fluorinated cyclic carboxylate (fluorine-containing lactone). Examples of the fluorine-containing lactone include fluorine-containing lactones represented by the following formula (C):

[Chem. 59]

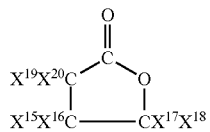

(C)

wherein $X^{15}$ to $X^{20}$ are the same as or different from each other, and are each —H, —F, —Cl, —CH$_3$, or a fluorinated alkyl group; and at least one of $X^{15}$ to $X^{20}$ is a fluorinated alkyl group.

Examples of the fluorinated alkyl group for $X^{15}$ to $X^{20}$ include —CFH$_2$, —CF$_2$H, —CF$_3$, —CH$_2$CF$_3$, —CF$_2$CF$_3$, —CH$_2$CF$_2$CF$_3$, and —CF(CF$_3$)$_2$. In order to achieve high oxidation resistance and an effect of improving the safety, —CH$_2$CF$_3$ and —CH$_2$CF$_2$CF$_3$ are preferred.

One of $X^{15}$ to $X^{20}$ or a plurality thereof may be replaced by —H, —F, —Cl, —CH$_3$, or a fluorinated alkyl group only when at least one of $X^{15}$ to $X^{20}$ is a fluorinated alkyl group. In order to achieve good solubility of the electrolyte salt, the number of substituents is preferably 1 to 3, more preferably 1 or 2.

The substitution of the fluorinated alkyl group may be at any of the above sites. In order to achieve a good synthesizing yield, the substitution site is preferably $X^{17}$ and/or $X^{18}$. In particular, $X^{17}$ or $X^{18}$ is preferably a fluorinated alkyl group, especially —CH$_2$CF$_3$ or —CH$_2$CF$_2$CF$_3$. The substituent for $X^{15}$ to $X^{20}$ other than the fluorinated alkyl group is —H, —F, —Cl, or CH$_3$. In order to achieve good solubility of the electrolyte salt, —H is preferred.

In addition to those represented by the above formula, the fluorine-containing lactone may also be a fluorine-containing lactone represented by the following formula (D):

[Chem. 60]

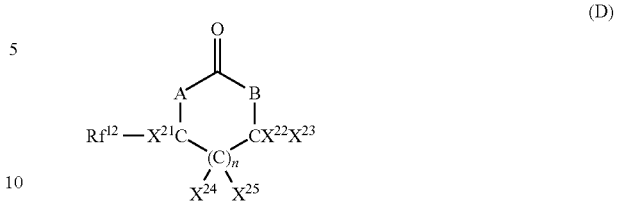

(D)

wherein one of A and B is $CX^{26}X^{27}$ (where $X^{26}$ and $X^{27}$ are the same as or different from each other, and are each —H, —F, —Cl, —CF$_3$, —CH$_3$, or an alkylene group in which a hydrogen atom is optionally replaced by a halogen atom and which optionally contains a hetero atom in the chain) and the other is an oxygen atom; $Rf^{12}$ is a fluorinated alkyl group or fluorinated alkoxy group optionally containing an ether bond; $X^{21}$ and $X^{22}$ are the same as or different from each other, and are each —H, —F, —Cl, —CF$_3$, or CH$_3$; $X^{23}$ to $X^{25}$ are the same as or different from each other, and are each —H, —F, —Cl, or an alkyl group in which a hydrogen atom is optionally replaced by a halogen atom and which optionally contains a hetero atom in the chain; and n=0 or 1.

A preferred example of the fluorine-containing lactone represented by the formula (D) is a 5-membered ring structure represented by the following formula (E):

[Chem. 61]

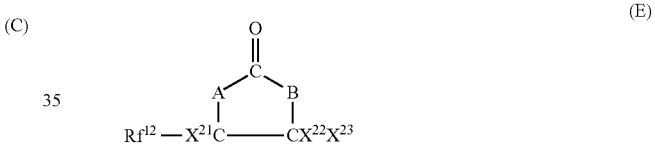

(E)

(wherein A, B, $Rf^{12}$, $X^{21}$, $X^{22}$, and $X^{23}$ are defined in the same manner as in the formula (D)) because it can be easily synthesized and can have good chemical stability. Further, in relation to the combination of A and B, fluorine-containing lactones represented by the following formula (F):

[Chem. 62]

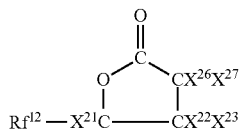

(F)

(wherein $Rf^{12}$, $X^{21}$, $X^{22}$, $X^{23}$, $X^{26}$, and $X^{27}$ are defined in the same manner as in the formula (D)) and fluorine-containing lactones represented by the following formula (G):

[Chem. 63]

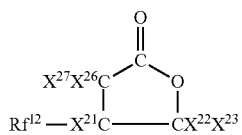

(G)

(wherein $Rf^{12}$, $X^{21}$, $X^{22}$, $X^{23}$, $X^{26}$, and $X^{27}$ are defined in the same manner as in the formula (D)) may be mentioned.

In order to particularly achieve excellent characteristics such as high permittivity and high withstand voltage, and to improve the characteristics of the electrolyte solution in the invention, for example, to achieve good solubility of the electrolyte salt and to reduce the internal resistance well, those represented by the following formulae:

[Chem. 64]

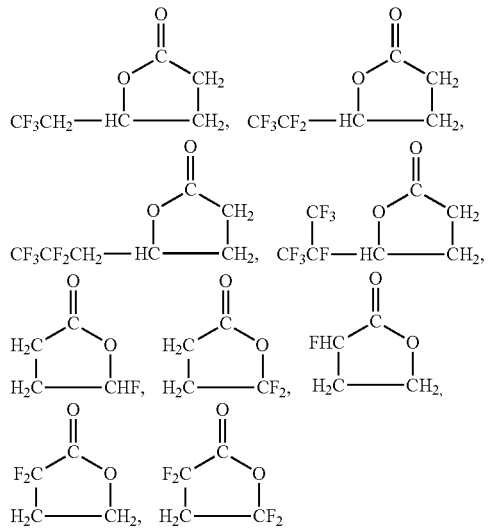

may be mentioned.

The presence of a fluorinated cyclic carboxylate can lead to, for example, effects of improving the ion conductivity, improving the safety, and improving the stability at high temperature.

The ether compound is preferably a C3-C10 acyclic ether or a C3-C6 cyclic ether.

Examples of the C3-C10 acyclic ether include diethyl ether, di-n-butyl ether, dimethoxymethane, methoxyethoxymethane, diethoxymethane, dimethoxyethane, methoxyethoxyethane, diethoxyethane, ethylene glycol di-n-propyl ether, ethylene glycol di-n-butyl ether, and diethylene glycol dimethyl ether.

Further, the ether compound may also suitably be a fluorinated ether.

An example of the fluorinated ether is a fluorinated ether (I) represented by the following formula (I):

(wherein $Rf^3$ and $Rf^4$ are the same as or different from each other, and are each a C1-C10 alkyl group or a C1-C10 fluorinated alkyl group; and at least one selected from $Rf^3$ and $Rf^4$ is a fluorinated alkyl group). The presence of the fluorinated ether (K) can improve the incombustibility of the electrolyte solution, as well as improve the stability and safety at high temperature under high voltage.

In the formula (I), at least one selected from $Rf^3$ and $Rf^4$ has only to be a C1-C10 fluorinated alkyl group. In order to further improve the incombustibility and the stability and safety at high temperature under high voltage of the electrolyte solution, both $Rf^3$ and $Rf^4$ are preferably C1-C10 fluorinated alkyl groups. In this case, $Rf^3$ and $Rf^4$ may be the same as or different from each other.

Particularly preferably, $Rf^3$ and $Rf^4$ are the same as or different from each other, and $Rf^3$ is a C3-C6 fluorinated alkyl group and $Rf^4$ is a C2-C6 fluorinated alkyl group.

If the sum of the carbon numbers of $Rf^3$ and $Rf^4$ is too small, the fluorinated ether may have too low a boiling point. Too large a carbon number of $Rf^3$ or $Rf^4$ may cause low solubility of the electrolyte salt, may start to adversely affect the miscibility with other solvents, and may cause high viscosity, resulting in poor rate characteristics. In order to achieve an excellent boiling point and rate characteristics, advantageously, the carbon number of $Rf^3$ is 3 or 4 and the carbon number of $Rf^4$ is 2 or 3.

The fluorinated ether (I) preferably has a fluorine content of 20 to 75% by mass. The fluorinated ether (K) having a fluorine content within this range may lead to particularly excellent balance between the non-flammability and the miscibility. The above range is also preferred for good oxidation resistance and safety.

The lower limit of the fluorine content is more preferably 30% by mass, still more preferably 40% by mass, particularly preferably 55% by mass. The upper limit thereof is more preferably 70% by mass, still more preferably 66% by mass.

The fluorine content of the fluorinated ether (I) is a value calculated based on the structural formula of the fluorinated ether (I) by the following formula:

$$\{(\text{Number of fluorine atoms} \times 19)/(\text{molecular weight of fluorinated ether }(I))\} \times 100(\%).$$

Examples of $Rf^3$ include $CF_3CF_2-$, $CF_3CH_2-$, $CF_2HCF_2-$, $CF_3CF_2CH_2-$, $CF_3CFHCF_2-$, $HCF_2CF_2CF_2-$, $HCF_2CF_2CH_2-$, $CF_3CF_2CH_2CH_2-$, $CF_3CFHCF_2CH_2-$, $HCF_2CF_2CF_2CF_2-$, $HCF_2CF_2CF_2CH_2-$, $HCF_2CF_2CH_2CH_2-$, and $HCF_2CF(CF_3)CH_2-$. Examples of $Rf^4$ include $-CH_2CF_2CF_3$, $-CF_2CFHCF_3$, $-CF_2CF_2CF_2H$, $-CH_2CF_2CF_2H$, $-CH_2CH_2CF_2CF_3$, $-CH_2CF_2CFHCF_3$, $-CF_2CF_2CF_2CF_2H$, $-CH_2CF_2CF_2CF_2H$, $-CH_2CH_2CF_2CF_2H$, $-CH_2CF(CF_3)$ $CF_2H$, $-CF_2CF_2H$, $-CH_2CF_2H$, and $-CF_2CH_3$.

Specific examples of the fluorinated ether (I) include $HCF_2CF_2CH_2OCF_2CF_2H$, $CF_3CF_2CH_2OCF_2CF_2H$, $HCF_2CF_2CH_2OCF_2CFHCF_3$, $CF_3CF_2CH_2OCF_2CFHCF_3$, $C_6F_{13}OCH_3$, $C_6F_{13}OC_2H_5$, $C_8F_{17}OCH_3$, $C_8F_{17}OC_2H_5$, $CF_3CFHCF_2CH(CH_3)$ $OCF_2CFHCF_3$, $HCF_2CF_2OCH$ $(C_2H_5)_2$, $HCF_2CF_2OC_4H_9$, $HCF_2CF_2OCH_2CH(C_2H_5)_2$, $HCF_2CF_2OCH_2CH(CH_3)_2$, $HCF_2CF_2OC_3H_7$, and $CF_3CH_2OCH_2CH_2OCH_3$.

In particular, those having $HCF_2-$ or $CF_3CFH-$ at one end or both ends can provide a fluorinated ether (I) having excellent polarizability and a high boiling point. The boiling point of the fluorinated ether (I) is preferably 67° C. to 120° C., more preferably 80° C. or higher, still more preferably 90° C. or higher.

Such a fluorinated ether (I) may include one or two or more of $CF_3CH_2OCF_2CFHCF_3$, $CF_3CF_2CH_2OCF_2CFHCF_3$, $HCF_2CF_2CH_2OCF_2CFHCF_3$, $HCF_2CF_2CH_2OCH_2CF_2CF_2H$, $CF_3CFHCF_2CH_2OCF_2CFHCF_3$, $HCF_2CF_2CH_2OCF_2CF_2H$, $CF_3CF_2CH_2OCF_2CF_2H$, and the like.

The fluorinated ether (I) is preferably at least one selected from the group consisting of $HCF_2CF_2CH_2OCF_2CFHCF_3$ (boiling point: 106° C.), $CF_3CF_2CH_2OCF_2CFHCF_3$ (boiling point: 82° C.), $HCF_2CF_2CH_2OCF_2CF_2H$ (boiling point: 92° C.), and $CF_3CF_2CH_2OCF_2CF_2H$ (boiling point: 68° C.), more preferably at least one selected from the group consisting of $HCF_2CF_2CH_2OCF_2CFHCF_3$ (boiling point: 106°

C.), and HCF$_2$CF$_2$CH$_2$OCF$_2$CF$_2$H (boiling point: 92° C.), because they can advantageously have a high boiling point and good miscibility with other solvents, and lead to good solubility of the electrolyte salt.

Examples of the C3-C6 cyclic ether include 1,3-dioxane, 2-methyl-1,3-dioxane, 4-methyl-1,3-dioxane, 1,4-dioxane, and fluorinated compounds thereof. Preferred are dimethoxymethane, diethoxymethane, ethoxymethoxymethane, ethylene glycol n-propyl ether, ethylene glycol di-n-butyl ether, and diethylene glycol dimethyl ether because they can have a high ability to solvate with lithium ions and improve the degree of ion dissociation. Particularly preferred are dimethoxymethane, diethoxymethane, and ethoxymethoxymethane because they can have low viscosity and give a high ion conductivity.

Examples of the nitrogen-containing compound include nitrile, fluorine-containing nitrile, carboxylic acid amide, fluorine-containing carboxylic acid amide, sulfonic acid amide, and fluorine-containing sulfonic acid amide. Also, 1-methyl-2-pyrrolidinone, 1-methyl-2-piperidone, 3-methyl-2-oxazilidinone, 1,3-dimethyl-2-imidazolidinone, and N-methylsuccinimide may be used. The nitrile compounds represented by any of the formulae (1a), (1b), and (1c) are not included in the nitrogen-containing compound.

Examples of the boron-containing compound include borates such as trimethyl borate and triethyl borate, boric acid ethers, and alkyl borates.

Examples of the organosilicon-containing compound include (CH$_3$)$_4$—Si and (CH$_3$)$_3$—Si—Si(CH$_3$)$_3$.

Examples of the fireproof agent (flame retardant) include organophosphates and phosphazene-based compounds. Examples of the organophosphates include fluorine-containing alkyl phosphates, non-fluorine-containing alkyl phosphates, and aryl phosphates. In order to achieve a flame retardant effect even at a small amount, fluorine-containing alkyl phosphates are particularly preferred.

Specific examples of the fluorine-containing alkyl phosphates include fluorine-containing dialkyl phosphates disclosed in JP H11-233141 A, cyclic alkyl phosphates disclosed in JP H11-283669 A, and fluorine-containing trialkyl phosphates.

Preferred examples of the fireproof agent (flame retardant) include (CH$_3$O)$_3$P=O, (CF$_3$CH$_2$O)$_3$P=O, (HCF$_2$CH$_2$O)$_3$P=O, (CF$_3$CF$_2$CH$_2$)$_3$P=O, (CF$_3$CH$_2$)$_3$P=O, and (HCF$_2$CF$_2$CH$_2$)$_3$P=O.

The surfactant may be any of cationic surfactants, anionic surfactants, nonionic surfactants, and amphoteric surfactants. In order to achieve good cycle characteristics and rate characteristics, the surfactant is preferably one containing a fluorine atom.

Preferred examples of such a surfactant containing a fluorine atom include fluorine-containing carboxylic acid salts represented by the following formula (3):

(wherein Rf$^5$ is a C3-C10 fluorine-containing alkyl group optionally containing an ether bond; M$^+$ is Li$^+$, Na$^+$, K$^+$, or NHR'$_3^+$, wherein R's are the same as or different from each other, and are each H or a C1-C3 alkyl group), and fluorine-containing sulfonic acid salts represented by the following formula (4):

(wherein Rf$^6$ is a C3-C10 fluorine-containing alkyl group optionally containing an ether bond; M$^+$ is Li$^+$, Na$^+$, K$^+$, or NHR'$_3^+$, wherein R's are the same as or different from each other, and are each H or a C1-C3 alkyl group).

In order to reduce the surface tension of the electrolyte solution without impairing the charge and discharge cycle characteristics, the amount of the surfactant is preferably 0.01 to 2% by mass in the electrolyte solution.

Examples of the additive for increasing the permittivity include sulfolane, methyl sulfolane, γ-butyrolactone, and γ-valerolactone.

Examples of the improver for cycle characteristics and rate characteristics include methyl acetate, ethyl acetate, tetrahydrofuran, and 1,4-dioxane.

The electrolyte solution of the invention may be combined with a polymer material and thereby formed into a gel-like (plasticized), gel electrolyte solution.

Examples of such a polymer material include conventionally known polyethylene oxide and polypropylene oxide, and modified products thereof (see JP H08-222270 A, JP 2002-100405 A); polyacrylate-based polymers, polyacrylonitrile, and fluororesins such as polyvinylidene fluoride and vinylidene fluoride-hexafluoropropylene copolymers (see JP H04-506726 T, JP H08-507407 T, JP H10-294131 A); and composites of any of these fluororesins and any hydrocarbon resin (see JP H11-35765 A, JP H11-86630 A). In particular, polyvinylidene fluoride or a vinylidene fluoride-hexafluoropropylene copolymer is preferably used as a polymer material for a gel electrolyte.

The electrolyte solution of the invention may also contain an ion conductive compound disclosed in Japanese Patent Application No. 2004-301934.

This ion conductive compound is an amorphous fluorine-containing polyether compound having a fluorine-containing group at a side chain and is represented by the following formula (1-1):

wherein D is represented by the following formula (2-1):

[wherein D1 is an ether unit containing a fluorine-containing ether group at a side chain and is represented by the following formula (2a):

[Chem. 65]

(wherein R$^f$ is a fluorine-containing ether group optionally containing a crosslinkable functional group; and R$^{10}$ is a group or a bond that links Rf and the main chain);

FAE is an ether unit containing a fluorinated alkyl group at a side chain and is represented by the following formula (2b):

[Chem. 66]

(wherein Rfa is a hydrogen atom or a fluorinated alkyl group optionally containing a crosslinkable functional group; and R$^{11}$ is a group or a bond that links Rfa and the main chain);

AE is an ether unit represented by the following formula (2c):

[Chem. 67]

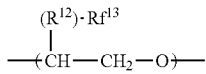
(2c)

(wherein $R^{13}$ is a hydrogen atom, an alkyl group optionally containing a crosslinkable functional group, an aliphatic cyclic hydrocarbon group optionally containing a crosslinkable functional group, or an aromatic hydrocarbon group optionally containing a crosslinkable functional group; and $R^{12}$ is a group or a bond that links $R^{13}$ and the main chain);

Y is a unit containing at least one selected from the following formulae (2d-1) to (2d-3):

[Chem. 68]

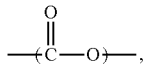
(2d-1)

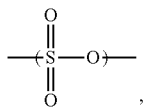
(2d-2)

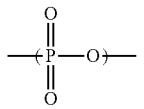
(2d-3)

n is an integer of 0 to 200;
m is an integer of 0 to 200;
p is an integer of 0 to 10000;
q is an integer of 1 to 100;
n+m is not 0; and
the bonding order of D1, FAE, AE, and Y is not specified]; and A and B are the same as or different from each other, and are each a hydrogen atom, an alkyl group optionally containing a fluorine atom and/or a crosslinkable functional group, a phenyl group optionally containing a fluorine atom and/or a crosslinkable functional group, a —COOH group, —OR (where R is a hydrogen atom or an alkyl group optionally containing a fluorine atom and/or a crosslinkable functional group), an ester group, or a carbonate group, and when an end of D is an oxygen atom, A and B are each none of a —COOH group, —OR, an ester group, and a carbonate group).

The electrolyte solution of the invention may further contain a different additive, if necessary. Examples of the different additive include metal oxides and glass.

The electrolyte solution of the invention preferably has a hydrogen fluoride (HF) content of 5 to 300 ppm. The presence of HF can promote formation of a film of the above additive. Too small an amount of HF tends to impair the ability to form a film on the negative electrode, impairing the characteristics of an electrochemical device. Too large an amount of HF tends to impair the oxidation resistance of the electrolyte solution due to the influence by HF. The electrolyte solution of the invention, even when containing HF in an amount within the above range, causes no reduction in capacity recovery in high-temperature storage of an electrochemical device.

The amount of HF is more preferably 10 ppm or more, still more preferably 20 ppm or more. The amount of HF is also more preferably 150 ppm or less, still more preferably 100 ppm or less, particularly preferably 50 ppm or less.

The amount of HF can be determined by neutralization titration.

The electrolyte solution of the invention may be prepared by any method using the aforementioned components.

The electrolyte solution of the invention can give a low resistance to an electrochemical device while maintaining the cycle characteristics of the electrochemical device and can reduce generation of gas during cycles although the electrolyte solution contains a fluorine-based solvent as a result of the presence of the compounds (1) and (2) in the solvent.

The electrolyte solution of the invention can be suitably applied to electrochemical devices such as lithium-ion secondary batteries and electric double layer capacitors. An electrochemical device including the electrolyte solution of the invention is also one aspect of the invention.

Examples of the electrochemical devices include lithium-ion secondary batteries, capacitors (electric double-layer capacitors), radical batteries, solar cells (in particular, dye-sensitized solar cells), fuel cells, various electrochemical sensors, electrochromic elements, electrochemical switching elements, aluminum electrolytic capacitors, and tantalum electrolytic capacitors. Preferred are lithium-ion secondary batteries and electric double-layer capacitors.

A module including the electrochemical device is also one aspect of the invention. A module including the lithium-ion secondary battery is also one aspect of the invention.

The invention also relates to a lithium-ion secondary battery including the electrolyte solution of the invention. The lithium-ion secondary battery of the invention may include a positive electrode, a negative electrode, and the above electrolyte solution.

<Positive Electrode>

The positive electrode includes a positive electrode active material layer containing a positive electrode active material and a current collector.

The positive electrode active material may be any material that can electrochemically occlude and release lithium ions. For example, a substance containing lithium and at least one transition metal is preferred. Specific examples thereof include lithium-containing transition metal complex oxides and lithium-containing transition metal phosphoric acid compounds. In particular, the positive electrode active material is preferably a lithium-containing transition metal complex oxide that generates high voltage.

The transition metal of the lithium-containing transition metal complex oxide is preferably V, Ti, Cr, Mn, Fe, Co, Ni, Cu, or the like. Specific examples thereof include lithium-cobalt complex oxides such as $LiCoO_2$, lithium-nickel complex oxides such as $LiNiO_2$, lithium-manganese complex oxides such as $LiMnO_2$, $LiMn_2O_4$, and $Li_2MnO_4$, and those obtained by substituting some of transition metal atoms as main components of these lithium transition metal complex oxides with another element such as Na, K, B, F, Al, Ti, V, Cr, Mn, Fe, Co, Li, Ni, Cu, Zn, Mg, Ga, Zr, Si, Nb, Mo, Sn, or W. Specific examples of those obtained by substitution include $LiNi_{0.5}Mn_{0.5}O_2$, $LiNi_{0.85}Co_{0.05}O_2$, $LiNi_{0.5}Co_{0.2}Mn_{0.3}O_2$, $LiNi_{0.6}Co_{0.2}Mn_{0.2}O_2$, $LiNi_{0.33}Co_{0.33}Mn_{0.33}O_2$, $LiNi_{0.45}Co_{0.10}Al_{0.45}O_2$, $LiMn_{1.8}Al_{0.2}O_4$, and $LiMn_{1.5}Ni_{0.5}O_4$.

The lithium-containing transition metal complex oxide is preferably any of $LiMn_{1.5}Ni_{0.5}O_4$, $LiNi_{0.5}Co_{0.2}Mn_{0.3}O_2$, and $LiNi_{0.6}Co_{0.2}Mn_{0.2}O_2$ each of which has a high energy density even at high voltage.

The transition metal of the lithium-containing transition metal phosphoric acid compound is preferably V, Ti, Cr, Mn, Fe, Co, Ni, Cu, or the like. Specific examples thereof include iron phosphates such as $LiFePO_4$, $Li_3Fe_2(PO_4)_3$, and $LiFeP_2O_7$, cobalt phosphates such as $LiCoPO_4$, and those obtained by substituting some of transition metal atoms as main components of these lithium transition metal phosphoric acid compounds with another element such as Al, Ti, V, Cr, Mn, Fe, Co, Li, Ni, Cu, Zn, Mg, Ga, Zr, Nb, or Si.

Examples of the lithium-containing transition metal complex oxide include lithium-manganese spinel complex oxides represented by the formula: $Li_aMn_{2-b}M^1{}_bO_4$ (wherein $0.9 \leq a$; $0 \leq b \leq 1.5$; and $M^1$ is at least one metal selected from the group consisting of Fe, Co, Ni, Cu, Zn, Al, Sn, Cr, V, Ti, Mg, Ca, Sr, B, Ga, In, Si, and Ge), lithium-nickel complex oxides represented by the formula: $LiNi_{1-c}M^2{}_cO_2$ (wherein $0 \leq c \leq 0.5$; and $M^2$ is at least one metal selected from the group consisting of Fe, Co, Mn, Cu, Zn, Al, Sn, Cr, V, Ti, Mg, Ca, Sr, B, Ga, In, Si, and Ge), and lithium-cobalt complex oxides represented by the formula: $LiCo_{1-d}M^3{}_dO_2$ (wherein $0 \leq d \leq 0.5$; and $M^3$ is at least one metal selected from the group consisting of Fe, Ni, Mn, Cu, Zn, Al, Sn, Cr, V, Ti, Mg, Ca, Sr, B, Ga, In, Si, and Ge).

In order to provide a high-power lithium-ion secondary battery having a high energy density, preferred is $LiCoO_2$, $LiMnO_2$, $LiNiO_2$, $LiMn_2O_4$, $LiNi_{0.8}Co_{0.15}Al_{0.05}O_2$, or $LiNi_{1/3}Co_{1/3}Mn_{1/3}O_2$.

Other examples of the positive electrode active material include $LiFePO_4$, $LiNi_{0.8}Co_{0.2}O_2$, $Li_{1.2}Fe_{0.4}Mn_{0.4}O_2$, $LiNi_{0.5}Mn_{0.5}O_2$, and $LiV_3O_6$.

In order to improve the continuous charge characteristics, the positive electrode active material preferably contains lithium phosphate. Lithium phosphate may be used in any manner, and is preferably used in admixture with the positive electrode active material. The lower limit of the amount of lithium phosphate used is preferably 0.1% by mass or more, more preferably 0.3% by mass or more, still more preferably 0.5% by mass or more, relative to the sum of the amounts of the positive electrode active material and lithium phosphate. The upper limit thereof is preferably 10% by mass or less, more preferably 8% by mass or less, still more preferably 5% by mass or less.

To a surface of the positive electrode active material may be attached a substance having a composition different from the positive electrode active material. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, and magnesium carbonate; and carbon.

Such a substance may be attached to a surface of the positive electrode active material by, for example, a method of dissolving or suspending the substance in a solvent, impregnating the solution or suspension into the positive electrode active material, and drying the impregnated material; a method of dissolving or suspending a precursor of the substance in a solvent, impregnating the solution or suspension into the positive electrode active material, and heating the material and the precursor to cause a reaction therebetween; or a method of adding the substance to a precursor of the positive electrode active material and simultaneously sintering the materials. In the case of attaching carbon, for example, a carbonaceous material in the form of activated carbon may be mechanically attached to the surface afterward.

For the amount of the substance attached to the surface in terms of the mass relative to the amount of the positive electrode active material, the lower limit thereof is preferably 0.1 ppm or more, more preferably 1 ppm or more, still more preferably 10 ppm or more, while the upper limit thereof is preferably 20% or less, more preferably 10% or less, still more preferably 5% or less. The substance attached to the surface can reduce oxidation of the electrolyte solution on the surface of the positive electrode active material, improving the battery life. Too small an amount of the substance may fail to sufficiently provide this effect. Too large an amount thereof may hinder the entrance and exit of lithium ions, increasing the resistance.

Particles of the positive electrode active material may have any shape conventionally used, such as a bulky shape, a polyhedral shape, a spherical shape, an ellipsoidal shape, a plate shape, a needle shape, or a pillar shape. The primary particles may agglomerate to form secondary particles.

The positive electrode active material has a tap density of preferably 0.5 g/cm$^3$ or higher, more preferably 0.8 g/cm$^3$ or higher, still more preferably 1.0 g/cm$^3$ or higher. The positive electrode active material having a tap density below the lower limit may cause an increased amount of a dispersion medium required and increased amounts of a conductive material and a binder required in formation of the positive electrode active material layer, as well as limitation on the packing fraction of the positive electrode active material in the positive electrode active material layer, resulting in limitation on the battery capacity. A complex oxide powder having a high tap density enables formation of a positive electrode active material layer with a high density. The tap density is preferably as high as possible and has no upper limit, in general. Still, too high a tap density may cause diffusion of lithium ions in the positive electrode active material layer with the electrolyte solution serving as a diffusion medium to function as a rate-determining step, easily impairing the load characteristics. Thus, the upper limit of the tap density is preferably 4.0 g/cm$^3$ or lower, more preferably 3.7 g/cm$^3$ or lower, still more preferably 3.5 g/cm$^3$ or lower.

In the invention, the tap density is determined as a powder packing density (tap density) g/cm$^3$ when 5 to 10 g of the positive electrode active material powder is packed into a 10-ml glass graduated cylinder and the cylinder is tapped 200 times with a stroke of about 20 mm.

The particles of the positive electrode active material have a median size d50 (or a secondary particle size when the primary particles agglomerate to form secondary particles) of preferably 0.3 µm or greater, more preferably 0.5 µm or greater, still more preferably 0.8 µm or greater, most preferably 1.0 µm or greater, while preferably 30 µm or smaller, more preferably 27 µm or smaller, still more preferably 25 µm or smaller, most preferably 22 µm or smaller. The particles having a median size below the lower limit may fail to provide a product with a high tap density. The particles having a median size greater than the upper limit may cause prolonged diffusion of lithium in the particles, impairing the battery performance and generating streaks in formation of the positive electrode for a battery, i.e., when the active material and components such as a conductive material and a binder are formed into slurry by adding a solvent and the slurry is applied in the form of a film, for example. Mixing two or more positive electrode active materials having different median sizes d50 can further improve the easiness of packing in formation of the positive electrode.

In the invention, the median size d50 is determined using a known laser diffraction/scattering particle size distribution analyzer. In the case of using LA-920 (Horiba, Ltd.) as the particle size distribution analyzer, the dispersion medium used in the measurement is a 0.1% by mass sodium hexametaphosphate aqueous solution and the measurement refractive index is set to 1.24 after 5-minute ultrasonic dispersion.

When the primary particles agglomerate to form secondary particles, the average primary particle size of the positive electrode active material is preferably 0.05 µm or greater, more preferably 0.1 µm or greater, still more preferably 0.2 µm or greater. The upper limit thereof is preferably 5 µm or smaller, more preferably 4 µm or smaller, still more preferably 3 µm or smaller, most preferably 2 µm or smaller. The primary particles having an average primary particle size greater than the upper limit may have difficulty in forming spherical secondary particles, adversely affecting the powder packing. Further, such primary particles may have a greatly reduced specific surface area, highly possibly impairing the battery performance such as increasing the resistance. In contrast, the primary particles having an average primary particle size below the lower limit may usually be insufficiently grown crystals, causing poor charge and discharge reversibility, for example.

In the invention, the primary particle size is measured by scanning electron microscopic (SEM) observation. Specifically, the primary particle size is determined as follows. A photograph at a magnification of 10000× is first taken. Any 50 primary particles are selected and the maximum length between the left and right boundary lines of each primary particle is measured along the horizontal line. Then, the average value of the maximum lengths is calculated, which is defined as the primary particle size.

The positive electrode active material has a BET specific surface area of preferably 0.1 $m^2/g$ or larger, more preferably 0.2 $m^2/g$ or larger, still more preferably 0.3 $m^2/g$ or larger. The upper limit thereof is preferably 50 $m^2/g$ or smaller, more preferably 40 $m^2/g$ or smaller, still more preferably 30 $m^2/g$ or smaller. The positive electrode active material having a BET specific surface area smaller than the above range may easily impair the battery performance. The positive electrode active material having a BET specific surface area larger than the above range may less easily have an increased tap density, easily causing a difficulty in applying the material in formation of the positive electrode active material layer.

In the invention, the BET specific surface area is defined by a value determined by single point BET nitrogen adsorption utilizing a gas flow method using a surface area analyzer (e.g., fully automatic surface area measurement device, Ohkura Riken Co., Ltd.), a sample pre-dried in nitrogen stream at 150° C. for 30 minutes, and a nitrogen-helium gas mixture with the nitrogen pressure relative to the atmospheric pressure being accurately adjusted to 0.3.

When the lithium-ion secondary battery of the invention is used as a large-size lithium-ion secondary battery for hybrid vehicles or distributed generation, it needs to achieve high output. Thus, the particles of the positive electrode active material preferably mainly composed of secondary particles.

The particles of the positive electrode active material preferably include 0.5 to 7.0% by volume of fine particles having an average secondary particle size of 40 µm or smaller and having an average primary particle size of 1 µm or smaller. The presence of fine particles having an average primary particle size of 1 µm or smaller enlarges the contact area with the electrolyte solution and enables more rapid diffusion of lithium ions between the electrode and the electrolyte solution, improving the output performance of the battery.

The positive electrode active material may be produced by any usual method of producing an inorganic compound. In particular, a spherical or ellipsoidal active material can be produced by various methods. For example, a material substance of transition metal is dissolved or crushed and dispersed in a solvent such as water, and the pH of the solution or dispersion is adjusted under stirring to form a spherical precursor. The precursor is recovered and, if necessary, dried. Then, a Li source such as LiOH, $Li_2CO_3$, or $LiNO_3$ is added thereto and the mixture is sintered at high temperature, thereby providing an active material.

In production of the positive electrode, the aforementioned positive electrode active materials may be used alone or in any combination of two or more thereof having different compositions at any ratio. Preferred examples of the combination in this case include a combination of $LiCoO_2$ and $LiMn_2O_4$ in which part of Mn may optionally be replaced by a different transition metal (e.g., $LiNi_{0.33}Co_{0.33}Mn_{0.33}O_2$), and a combination with $LiCoO_2$ in which part of Co may optionally be replaced by a different transition metal.

In order to achieve a high battery capacity, the amount of the positive electrode active material is preferably 50 to 99% by mass, more preferably 80 to 99% by mass, of the positive electrode mixture. The amount of the positive electrode active material in the positive electrode active material layer is preferably 80% by mass or more, more preferably 82% by mass or more, particularly preferably 84% by mass or more. The upper limit thereof is preferably 99% by mass or less, more preferably 98% by mass or less. Too small an amount of the positive electrode active material in the positive electrode active material layer may cause an insufficient electric capacity. In contrast, too large an amount thereof may cause insufficient strength of the positive electrode.

The positive electrode mixture preferably further contains a binder, a thickening agent, and a conductive material.

The binder may be any material that is safe against a solvent to be used in production of the electrode and the electrolyte solution. Examples thereof include resin polymers such as polyethylene, polypropylene, polyethylene terephthalate, polymethyl methacrylate, aromatic polyamide, chitosan, alginic acid, polyacrylic acid, polyimide, cellulose, and nitro cellulose; rubbery polymers such as SBR (styrene-butadiene rubber), isoprene rubber, butadiene rubber, fluoroelastomer, NBR (acrylonitrile-butadiene rubber), and ethylene-propylene rubber; styrene-butadiene-styrene block copolymers and hydrogenated products thereof; thermoplastic elastomeric polymers such as EPDM (ethylene-propylene-diene terpolymers), styrene-ethylene-butadiene-styrene copolymers, styrene-isoprene-styrene block copolymers and hydrogenated products thereof; soft resin polymers such as syndiotactic-1,2-polybutadiene, polyvinyl acetate, ethylene-vinyl acetate copolymers, and propylene-α-olefin copolymers; fluoropolymers such as polyvinylidene fluoride, polytetrafluoroethylene, vinylidene fluoride copolymers, and tetrafluoroethylene-ethylene copolymers; and polymer compositions having ion conductivity of alkali metal ions (especially, lithium ions). These may be used alone or in any combination of two or more at any ratio.

The amount of the binder, which is expressed as the proportion of the binder in the positive electrode active material layer, is usually 0.1% by mass or more, preferably 1% by mass or more, more preferably 1.5% by mass or more. The proportion is also usually 80% by mass or less, preferably 60% by mass or less, still more preferably 40% by mass or less, most preferably 10% by mass or less. Too low a proportion of the binder may fail to sufficiently hold the positive electrode active material and cause insufficient mechanical strength of the positive electrode, impairing the battery performance such as cycle characteristics. In contrast, too high a proportion thereof may cause reduction in battery capacity and conductivity.

Examples of the thickening agent include carboxymethyl cellulose, methyl cellulose, hydroxymethyl cellulose, ethyl cellulose, polyvinyl alcohol, oxidized starch, monostarch phosphate, casein, and salts thereof. These agents may be used alone or in any combination of two or more at any ratio.

The proportion of the thickening agent relative to the active material is usually 0.1% by mass or higher, preferably 0.2% by mass or higher, more preferably 0.3% by mass or higher, while usually 5% by mass or lower, preferably 3% by mass or lower, more preferably 2% by mass or lower. The thickening agent at a proportion lower than the above range may cause significantly poor easiness of application. The thickening agent at a proportion higher than the above range may cause a low proportion of the active material in the positive electrode active material layer, resulting in a low capacity of the battery and high resistance between the positive electrode active materials.

The conductive material may be any known conductive material. Specific examples thereof include metal materials such as copper and nickel, and carbon materials such as graphite, including natural graphite and artificial graphite, carbon black, including acetylene black, and amorphous carbon, including needle coke. These materials may be used alone or in any combination of two or more at any ratio. The conductive material is used in an amount of usually 0.01% by mass or more, preferably 0.1% by mass or more, more preferably 1% by mass or more, while usually 50% by mass or less, preferably 30% by mass or less, more preferably 15% by mass or less, in the positive electrode active material layer. The conductive material in an amount less than the above range may cause insufficient conductivity. In contrast, the conductive material in an amount more than the above range may cause a low battery capacity.

The solvent for forming slurry may be any solvent that can dissolve or disperse therein the positive electrode active material, the conductive material, and the binder, as well as a thickening agent used as appropriate. The solvent may be either an aqueous solvent or an organic solvent. Examples of the aqueous medium include water and solvent mixtures of an alcohol and water. Examples of the organic medium include aliphatic hydrocarbons such as hexane; aromatic hydrocarbons such as benzene, toluene, xylene, and methyl naphthalene; heterocyclic compounds such as quinoline and pyridine; ketones such as acetone, methyl ethyl ketone, and cyclohexanone; esters such as methyl acetate and methyl acrylate; amines such as diethylene triamine and N,N-dimethylaminopropylamine; ethers such as diethyl ether, propylene oxide, and tetrahydrofuran (THF); amides such as N-methylpyrrolidone (NMP), dimethyl formamide, and dimethyl acetamide; and aprotic polar solvents such as hexamethyl phosphoramide and dimethyl sulfoxide.

Examples of the material of the current collector for a positive electrode include metal materials such as aluminum, titanium, tantalum, stainless steel, and nickel, and alloys thereof; and carbon materials such as carbon cloth and carbon paper. Preferred is any metal material, especially aluminum or an alloy thereof.

In the case of a metal material, the current collector may be in the form of metal foil, metal cylinder, metal coil, metal plate, metal film, expanded metal, punched metal, metal foam, or the like. In the case of a carbon material, it may be in the form of carbon plate, carbon film, carbon cylinder, or the like. Preferred among these is a metal film. The film may be in the form of mesh, as appropriate. The film may have any thickness, and the thickness is usually 1 µm or greater, preferably 3 µm or greater, more preferably 5 µm or greater, while usually 1 mm or smaller, preferably 100 µm or smaller, more preferably 50 µm or smaller. The film having a thickness smaller than the above range may have insufficient strength as a current collector. In contrast, the film having a thickness greater than the above range may have poor handleability.

In order to reduce the electric contact resistance between the current collector and the positive electrode active material layer, the current collector also preferably has a conductive aid applied on the surface thereof. Examples of the conductive aid include carbon and noble metals such as gold, platinum, and silver.

The ratio between the thicknesses of the current collector and the positive electrode active material layer may be any value, and the ratio {(thickness of positive electrode active material layer on one side immediately before injection of electrolyte solution)/(thickness of current collector)} is preferably 20 or lower, more preferably 15 or lower, most preferably 10 or lower. The ratio is also preferably 0.5 or higher, more preferably 0.8 or higher, most preferably 1 or higher. The current collector and the positive electrode active material layer showing a ratio higher than the above range may cause the current collector to generate heat due to Joule heating during high-current-density charge and discharge. The current collector and the positive electrode active material layer showing a ratio lower than the above range may cause an increased ratio by volume of the current collector to the positive electrode active material, reducing the battery capacity.

The positive electrode may be produced by a usual method. An example of the production method is a method in which the positive electrode active material is mixed with the aforementioned binder, thickening agent, conductive material, solvent, and other components to form a slurry-like positive electrode mixture, and then this mixture is applied to a current collector, dried, and pressed so as to be densified.

The densification may be achieved using a manual press or a roll press, for example. The density of the positive electrode active material layer is preferably 1.5 g/cm$^3$ or higher, more preferably 2 g/cm$^3$ or higher, still more preferably 2.2 g/cm$^3$ or higher, while preferably 5 g/cm$^3$ or lower, more preferably 4.5 g/cm$^3$ or lower, still more preferably 4 g/cm$^3$ or lower. The positive electrode active material layer having a density higher than the above range may cause low permeability of the electrolyte solution toward the vicinity of the interface between the current collector and the active material, and poor charge and discharge characteristics particularly at a high current density, failing to provide high output. The positive electrode active material layer having a density lower than the above range may cause poor conductivity between the active materials and increase the battery resistance, failing to provide high output.

In order to improve the stability at high output and high temperature in the case of using the electrolyte solution of the invention, the area of the positive electrode active material layer is preferably large relative to the outer surface area of an external case of the battery. Specifically, the total area of the positive electrode is preferably 15 times or more, more preferably 40 times or more, greater than the surface area of the external case of the secondary battery. For closed, square-shaped cases, the outer surface area of an external case of the battery herein means the total area calculated from the dimensions of length, width, and thickness of the case portion into which a power-generating element is packed except for a protruding portion of a terminal. For closed, cylinder-like cases, the outer surface area of an external case of the battery herein means the geometric surface area of an approximated cylinder of the case portion into which a power-generating element is packed except for a protruding portion of a terminal. The total area of the positive electrode herein means the geometric surface area of the positive electrode mixture layer opposite to a mixture layer including the negative electrode active material. For structures including a current collector foil and positive electrode mixture layers on both sides of the current collector, the total area of the positive electrode is the sum of the areas calculated on the respective sides.

The positive electrode plate may have any thickness. In order to achieve a high capacity and high output, the lower limit of the thickness of the mixture layer on one side of the current collector excluding the thickness of the base metal foil is preferably 10 µm or greater, more preferably 20 µm or greater, while preferably 500 µm or smaller, more preferably 450 µm or smaller.

To a surface of the positive electrode plate may be attached a substance having a composition different from the positive electrode plate. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, and magnesium carbonate; and carbon.

<Negative Electrode>

The negative electrode includes a negative electrode active material layer containing a negative electrode active material and a current collector.

Examples of the negative electrode active material include carbonaceous materials that can occlude and release lithium such as pyrolysates of organic matter under various pyrolysis conditions, artificial graphite, and natural graphite; metal oxide materials that can occlude and release lithium such as tin oxide and silicon oxide; lithium metals; various lithium alloys; and lithium-containing metal complex oxide materials. Two or more of these negative electrode active materials may be used in admixture with each other.

The carbonaceous material that can occlude and release lithium is preferably artificial graphite produced by high-temperature treatment of easily graphitizable pitch from various materials, purified natural graphite, or a material obtained by surface treatment on such graphite with pitch or other organic matter and then carbonization of the surface-treated graphite. In order to achieve a good balance between the initial irreversible capacity and the high-current-density charge and discharge characteristics, the carbonaceous material is more preferably selected from carbonaceous materials obtained by heat-treating natural graphite, artificial graphite, artificial carbonaceous substances, or artificial graphite substances at 400° C. to 3200° C. once or more; carbonaceous materials which allow the negative electrode active material layer to include at least two or more carbonaceous matters having different crystallinities and/or have an interface between the carbonaceous matters having the different crystallinities; and carbonaceous materials which allow the negative electrode active material layer to have an interface between at least two or more carbonaceous matters having different orientations. These carbonaceous materials may be used alone or in any combination of two or more at any ratio.

Examples of the carbonaceous materials obtained by heat-treating artificial carbonaceous substances or artificial graphite substances at 400° C. to 3200° C. once or more include coal-based coke, petroleum-based coke, coal-based pitch, petroleum-based pitch, and those prepared by oxidizing these pitches; needle coke, pitch coke, and carbon materials prepared by partially graphitizing these cokes; pyrolysates of organic matter such as furnace black, acetylene black, and pitch-based carbon fibers; carbonizable organic matter and carbides thereof; and solutions prepared by dissolving carbonizable organic matter in a low-molecular-weight organic solvent such as benzene, toluene, xylene, quinoline, or n-hexane, and carbides thereof.

The metal material (excluding lithium-titanium complex oxides) to be used as the negative electrode active material may be any compound that can occlude and release lithium, and examples thereof include simple lithium, simple metals and alloys that constitute lithium alloys, and oxides, carbides, nitrides, silicides, sulfides, and phosphides thereof. The simple metals and alloys constituting lithium alloys are preferably materials containing any of metal and semi-metal elements in Groups 13 and 14, more preferably simple metal of aluminum, silicon, and tin (hereinafter, referred to as "specific metal elements"), and alloys and compounds containing any of these atoms. These materials may be used alone or in combination of two or more at any ratio.

Examples of the negative electrode active material containing at least one atom selected from the specific metal elements include simple metal of any one specific metal element, alloys of two or more specific metal elements, alloys of one or two or more specific metal elements and one or two or more other metal elements, compounds containing one or two or more specific metal elements, and composite compounds such as oxides, carbides, nitrides, silicides, sulfides, and phosphides of the compounds. Such a simple metal, alloy, or metal compound used as the negative electrode active material can lead to a high-capacity battery.

Examples thereof further include compounds in which any of the above composite compounds are complexly bonded with several elements such as simple metals, alloys, and nonmetal elements. Specifically, in the case of silicon or tin, for example, an alloy of this element and a metal that does not serve as a negative electrode may be used. In the case of tin, for example, a composite compound including a combination of 5 or 6 elements, including tin, a metal (excluding silicon) that serves as a negative electrode, a metal that does not serve as a negative electrode, and a nonmetal element, may be used.

Specific examples thereof include simple Si, $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_6Si$, $FeSi_2$, $MnSi_2$, $NbSi_2$, $TaSi_2$, $VSi_2$, $WSi_2$, $ZnSi_2$, SiC, $Si_3N_4$, $Si_2N_2O$, $SiO_v$ (0<v≤2), LiSiO, simple tin, $SnSiO_3$, LiSnO, $Mg_2Sn$, and $SnO_w$ (0<w≤2).

Examples thereof further include composite materials of Si or Sn used as a first constitutional element, and second and third constitutional elements. The second constitutional element is at least one selected from cobalt, iron, magnesium, titanium, vanadium, chromium, manganese, nickel, copper, zinc, gallium, and zirconium, for example. The third constitutional element is at least one selected from boron, carbon, aluminum, and phosphorus, for example.

In order to achieve a high battery capacity and excellent battery characteristics, the metal material is preferably simple silicon or tin (which may contain trace impurities), $SiO_v$ (0<v≤2), $SnO_w$ (0≤w≤2), a Si—Co—C composite material, a Si—Ni—C composite material, a Sn—Co—C composite material, or a Sn—Ni—C composite material.

The lithium-containing metal complex oxide material to be used as the negative electrode active material may be any material that can occlude and release lithium. In order to achieve good high-current-density charge and discharge characteristics, materials containing titanium and lithium are preferred, lithium-containing metal complex oxide materials containing titanium are more preferred, and complex oxides of lithium and titanium (hereinafter, abbreviated as "lithium titanium complex oxides") are still more preferred. In other words, use of a spinel-structured lithium titanium complex oxide in the negative electrode active material for an electrolyte battery is particularly preferred because this can markedly reduce the output resistance.

Preferred examples of the lithium titanium complex oxides include compounds represented by the following formula:

$$Li_xTi_yM_zO_4$$

wherein M is at least one element selected from the group consisting of Na, K, Co, Al, Fe, Ti, Mg, Cr, Ga, Cu, Zn, and Nb.

In order to achieve a good balance of the battery performance, particularly preferred among the above compositions are those satisfying any of the following:

(i) 1.2≤x≤1.4, 1.5≤y≤1.7, z=0
(ii) 0.9≤x≤1.1, 1.9≤y≤2.1, z=0
(iii) 0.7≤x≤0.9, 2.1≤y≤2.3, z=0.

Particularly preferred representative composition of the compound is $Li_{4/3}Ti_{5/3}O_4$ corresponding to the composition (i), $Li_1Ti_2O_4$ corresponding to the composition (ii), and $Li_{4/5}Ti_{11/5}O_4$ corresponding to the composition (iii). Preferred examples of the structure satisfying Z≠0 include $Li_{4/3}Ti_{4/3}Al_{1/3}O_4$.

The negative electrode mixture preferably further contains a binder, a thickening agent, and a conductive material.

Examples of the binder include the same binders as those mentioned for the positive electrode. The proportion of the binder is preferably 0.1% by mass or more, more preferably 0.5% by mass or more, particularly preferably 0.6% by mass or more, while preferably 20% by mass or less, more preferably 15% by mass or less, still more preferably 10% by mass or less, particularly preferably 8% by mass or less, relative to the negative electrode active material. The binder at a proportion relative to the negative electrode active material higher than the above range may lead to an increased proportion of the binder which fails to contribute to the battery capacity, causing a low battery capacity. The binder at a proportion lower than the above range may cause lowered strength of the negative electrode.

In particular, in the case of using a rubbery polymer typified by SBR as a main component, the proportion of the binder is usually 0.1% by mass or more, preferably 0.5% by mass or more, more preferably 0.6% by mass or more, while usually 5% by mass or less, preferably 3% by mass or less, more preferably 2% by mass or less, relative to the negative electrode active material. In the case of using a fluoropolymer typified by polyvinylidene fluoride as a main component, the proportion of the binder is usually 1% by mass or more, preferably 2% by mass or more, more preferably 3% by mass or more, while usually 15% by mass or less, preferably 10% by mass or less, more preferably 8% by mass or less, relative to the negative electrode active material.

Examples of the thickening agent include the same thickening agents as those mentioned for the positive electrode. The proportion of the thickening agent is usually 0.1% by mass or higher, preferably 0.5% by mass or higher, still more preferably 0.6% by mass or higher, while usually 5% by mass or lower, preferably 3% by mass or lower, still more preferably 2% by mass or lower, relative to the negative electrode active material. The thickening agent at a proportion relative to the negative electrode active material lower than the above range may cause significantly poor easiness of application. The thickening agent at a proportion higher than the above range may cause a small proportion of the negative electrode active material in the negative electrode active material layer, resulting in a low capacity of the battery and high resistance between the negative electrode active materials.

Examples of the conductive material of the negative electrode include metal materials such as copper and nickel; and carbon materials such as graphite and carbon black.

The solvent for forming slurry may be any solvent that can dissolve or disperse the negative electrode active material and the binder, as well as a thickening agent and a conductive material used as appropriate. The solvent may be either an aqueous solvent or an organic solvent.

Examples of the aqueous solvent include water and alcohols. Examples of the organic solvent include N-methylpyrrolidone (NMP), dimethyl formamide, dimethyl acetamide, methyl ethyl ketone, cyclohexanone, methyl acetate, methyl acrylate, diethyl triamine, N,N-dimethyl aminopropyl amine, tetrahydrofuran (THF), toluene, acetone, diethyl ether, dimethyl acetamide, hexamethyl phospharamide, dimethyl sulfoxide, benzene, xylene, quinoline, pyridine, methyl naphthalene, and hexane.

Examples of the material of the current collector for a negative electrode include copper, nickel, and stainless steel. In order to easily process the material into a film and to minimize the cost, copper foil is preferred.

The current collector usually has a thickness of 1 μm or greater, preferably 5 μm or greater, while usually 100 μm or smaller, preferably 50 μm or smaller. Too thick a negative electrode current collector may cause an excessive reduction in capacity of the whole battery, while too thin a current collector may be difficult to handle.

The negative electrode may be produced by a usual method. An example of the production method is a method in which the negative electrode material is mixed with the aforementioned binder, thickening agent, conductive material, solvent, and other components to form a slurry-like mixture, and then this mixture is applied to a current collector, dried, and pressed so as to be densified. In the case of using an alloyed material, a thin film layer containing the above negative electrode active material (negative electrode active material layer) may be produced by vapor deposition, sputtering, plating, or the like.

The electrode formed from the negative electrode active material may have any structure. The negative electrode active material existing on the current collector preferably has a density of 1 g·cm$^{-3}$ or higher, more preferably 1.2 g·cm$^{-3}$ or higher, particularly preferably 1.3 g·cm$^{-3}$ or higher, while preferably 2.2 g·cm$^{-3}$ or lower, more preferably 2.1 g·cm$^{-3}$ or lower, still more preferably 2.0 g·cm$^{-3}$ or lower, particularly preferably 1.9 g·cm$^{-3}$ or lower. The negative electrode active material existing on the current collector having a density higher than the above range may cause destruction of the negative electrode active material particles, resulting in a high initial irreversible capacity and poor high-current-density charge and discharge characteristics due to reduction in permeability of the electrolyte solution toward the vicinity of the interface between the current collector and the negative electrode active material. The negative electrode active material having a density below the above range may cause poor conductivity between the negative electrode active materials, high battery resistance, and a low capacity per unit volume.

The thickness of the negative electrode plate is a design matter in accordance with the positive electrode plate to be used, and may be any value. The thickness of the mixture layer excluding the thickness of the base metal foil is usually 15 μm or greater, preferably 20 μm or greater, more preferably 30 μm or greater, while usually 300 μm or smaller, preferably 280 μm or smaller, more preferably 250 μm or smaller.

To a surface of the negative electrode plate may be attached a substance having a composition different from the negative electrode plate. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; and carbonates such as lithium carbonate, calcium carbonate, and magnesium carbonate.

<Separator>

The lithium-ion secondary battery of the invention preferably further includes a separator.

The separator may be formed from any known material and may have any known shape as long as the resulting separator is stable to the electrolyte solution and is excellent in a liquid-retaining ability. The separator is preferably in the form of a porous sheet or a nonwoven fabric which is formed from a material stable to the electrolyte solution of the invention, such as resin, glass fiber, or inorganic matter, and which has an excellent liquid-retaining ability.

Examples of the material of a resin or glass-fiber separator include polyolefins such as polyethylene and polypropylene, aromatic polyamide, polytetrafluoroethylene, polyether sulfone, and glass filters. These materials may be used alone or in any combination of two or more at any ratio, for example, in the form of a polypropylene/polyethylene bilayer film or a polypropylene/polyethylene/polypropylene trilayer film. In order to achieve good permeability of the electrolyte solution and a good shut-down effect, the separator is preferably a porous sheet or a nonwoven fabric formed from a polyolefin such as polyethylene or polypropylene.

The separator may have any thickness, and the thickness is usually 1 μm or greater, preferably 5 μm or greater, more preferably 8 μm or greater, while usually 50 μm or smaller, preferably 40 μm or smaller, more preferably 30 μm or smaller. The separator thinner than the above range may have poor insulation and mechanical strength. The separator thicker than the above range may cause not only poor battery performance such as poor rate characteristics but also a low energy density of the whole electrolyte battery.

The separator which is a porous one such as a porous sheet or a nonwoven fabric may have any porosity. The porosity is usually 20% or higher, preferably 35% or higher, more preferably 45% or higher, while usually 90% or lower, preferably 85% or lower, more preferably 75% or lower. The separator having a porosity lower than the above range tends to have high film resistance, causing poor rate characteristics. The separator having a porosity higher than the above range tends to have low mechanical strength, causing poor insulation.

The separator may also have any average pore size. The average pore size is usually 0.5 μm or smaller, preferably 0.2 μm or smaller, while usually 0.05 μm or larger. The separator having an average pore size larger than the above range may easily cause short circuits. The separator having an average pore size smaller than the above range may have high film resistance, causing poor rate characteristics.

Examples of the inorganic matter include oxides such as alumina and silicon dioxide, nitrides such as aluminum nitride and silicon nitride, and sulfates such as barium sulfate and calcium sulfate, each in the form of particles or fibers.

The separator is in the form of a thin film such as a nonwoven fabric, a woven fabric, or a microporous film. The thin film favorably has a pore size of 0.01 to 1 μm and a thickness of 5 to 50 μm. Instead of the above separate thin film, the separator may have a structure in which a composite porous layer containing particles of the above inorganic matter is disposed on a surface of one or each of the positive and negative electrodes using a resin binder. For example, alumina particles having a 90% particle size of smaller than 1 μm may be applied to the respective surfaces of the positive electrode with fluororesin used as a binder to form a porous layer.

<Battery Design>

The electrode group may be either a laminate structure including the above positive and negative electrode plates with the above separator in between, or a wound structure including the above positive and negative electrode plates in spiral with the above separator in between. The proportion of the volume of the electrode group in the battery internal volume (hereinafter, referred to as an electrode group proportion) is usually 40% or higher, preferably 50% or higher, while usually 90% or lower, preferably 80% or lower.

The electrode group proportion lower than the above range may cause a low battery capacity. The electrode group proportion higher than the above range may cause small void space in the battery. Thus, if the battery temperature rises to high temperature and thereby the components swell and the liquid fraction of the electrolyte solution exhibits high vapor pressure to raise the internal pressure, the battery characteristics such as charge and discharge repeatability and high-temperature storageability may be impaired and a gas-releasing valve for releasing the internal pressure toward the outside may be actuated.

The current collecting structure may be any structure. In order to more effectively improve the high-current-density charge and discharge performance by the electrolyte solution of the invention, the current collecting structure is preferably a structure which reduces the resistances at wiring portions and jointing portions. Such reduction in internal resistance can particularly favorably lead to the effects achieved with the electrolyte solution of the invention.

In an electrode group having the laminate structure, the metal core portions of the respective electrode layers are preferably bundled and welded to a terminal. If an electrode has a large area, the internal resistance is high. Thus, multiple terminals may preferably be disposed in the electrode so as to reduce the resistance. In an electrode group having the wound structure, multiple lead structures may be disposed on each of the positive electrode and the negative electrode and bundled to a terminal. This can reduce the internal resistance.

The external case may be made of any material that is stable to an electrolyte solution to be used. Specific examples thereof include metals such as nickel-plated steel plates, stainless steel, aluminum and aluminum alloys, and magnesium alloys, and a layered film (laminate film) of resin and aluminum foil. In order to reduce the weight, a metal such as aluminum or an aluminum alloy or a laminate film is favorably used.

An external case made of metal may have a sealed-up structure formed by welding the metal by laser welding, resistance welding, or ultrasonic welding, or a caulking structure using the metal with a resin gasket in between. An external case made of a laminate film may have a sealed-up structure formed by hot-melting resin layers. In order to improve the sealability, a resin which is different from the resin of the laminate film may be disposed between the resin layers. Especially, in the case of forming a sealed-up structure by hot-melting the resin layers with current collecting terminals in between, metal and resin are to be bonded. Thus, the resin to be disposed between the resin layers is favorably a resin having a polar group or a modified resin having a polar group introduced therein.

The lithium-ion secondary battery of the invention may have any shape, such as a cylindrical shape, a square shape, a laminate shape, a coin shape, or a large-size shape. The shapes and the structures of the positive electrode, the negative electrode, and the separator may be changed in accordance with the shape of the battery.

A module including the lithium-ion secondary battery of the invention is also one aspect of the invention.

In a preferred embodiment, the lithium-ion secondary battery includes a positive electrode, a negative electrode, and the aforementioned electrolyte solution, the positive electrode including a positive electrode current collector and a positive electrode active material layer containing a positive electrode active material, the positive electrode active material containing Mn. The lithium-ion secondary battery including a positive electrode active material layer that contains a positive electrode active material containing Mn can have much better high-temperature storage characteristics.

In order to provide a high-power lithium-ion secondary battery having a high energy density, preferred as the positive electrode active material containing Mn are $LiMn_{1.5}Ni_{0.5}O_4$, $LiNi_{0.5}Co_{0.2}Mn_{0.3}O_2$, and $LiNi_{0.6}Co_{0.2}Mn_{0.2}O_2$.

The amount of the positive electrode active material in the positive electrode active material layer is preferably 80% by mass or more, more preferably 82% by mass or more, particularly preferably 84% by mass or more. The upper limit of the amount thereof is preferably 99% by mass or less, more preferably 98% by mass or less. Too small an amount of the positive electrode active material in the positive electrode active material layer may lead to an insufficient electric capacity. In contrast, too large an amount thereof may lead to insufficient strength of the positive electrode.

The positive electrode active material layer may further contain a conductive material, a thickening agent, and a binder.

The binder may be any material that is safe against a solvent to be used in production of electrodes and the electrolyte solution. Examples thereof include polyvinylidene fluoride, polytetrafluoroethylene, polyethylene, polypropylene, SBR (styrene-butadiene rubber), isoprene rubber, butadiene rubber, ethylene-acrylic acid copolymers, ethylene-methacrylic acid copolymers, polyethylene terephthalate, polymethyl methacrylate, polyimide, aromatic polyamide, cellulose, nitro cellulose, NBR (acrylonitrile-butadiene rubber), fluoroelastomer, ethylene-propylene rubber, styrene-butadiene-styrene block copolymers and hydrogenated products thereof, EPDM (ethylene-propylene-diene terpolymers), styrene-ethylene-butadiene-ethylene copolymers, styrene-isoprene-styrene block copolymers and hydrogenated products thereof, syndiotactic-1,2-polybutadiene, polyvinyl acetate, ethylene-vinyl acetate copolymers, propylene-α-olefin copolymers, fluorinated polyvinylidene fluoride, tetrafluoroethylene-ethylene copolymers, and polymer compositions having ion conductivity of alkali metal ions (especially, lithium ions). These substances may be used alone or in any combination of two or more at any ratio.

The amount of the binder, which is expressed as the proportion of the binder in the positive electrode active material layer, is usually 0.1% by mass or more, preferably 1% by mass or more, more preferably 1.5% by mass or more. The proportion is also usually 80% by mass or less, preferably 60% by mass or less, still more preferably 40% by mass or less, most preferably 10% by mass or less. Too low a proportion of the binder may fail to sufficiently hold the positive electrode active material and cause insufficient mechanical strength of the positive electrode, impairing the battery performance such as cycle characteristics. In contrast, too high a proportion thereof may cause reduction in battery capacity and conductivity.

Examples of the thickening agent include carboxymethyl cellulose, methyl cellulose, hydroxymethyl cellulose, ethyl cellulose, polyvinyl alcohol, oxidized starch, monostarch phosphate, casein, and salts thereof. These agents may be used alone or in any combination of two or more at any ratio.

The proportion of the thickening agent relative to the active material is usually 0.1% by mass or higher, preferably 0.2% by mass or higher, more preferably 0.3% by mass or higher, while usually 5% by mass or lower, preferably 3% by mass or lower, more preferably 2% by mass or lower. The thickening agent at a proportion lower than the above range may cause significantly poor easiness of application. The thickening agent at a proportion higher than the above range may cause a low proportion of the active material in the positive electrode active material layer, resulting in a low capacity of the battery and high resistance between the positive electrode active materials.

The conductive material may be any known conductive material. Specific examples thereof include metal materials such as copper and nickel, and carbon materials such as graphite, including natural graphite and artificial graphite, carbon black, including acetylene black, and amorphous carbon, including needle coke. These materials may be used alone or in any combination of two or more at any ratio. The conductive material is used in an amount of usually 0.01% by mass or more, preferably 0.1% by mass or more, more preferably 1% by mass or more, while usually 50% by mass or less, preferably 30% by mass or less, more preferably 15% by mass or less, in the positive electrode active material layer. The conductive material in an amount less than the above range may cause insufficient conductivity. In contrast, conductive material in an amount more than the above range may cause a low battery capacity.

In order to further improve the high-temperature storage characteristics, the positive electrode current collector is preferably formed from a valve metal or an alloy thereof. Examples of the valve metal include aluminum, titanium, tantalum, and chromium. The positive electrode current collector is more preferably formed from aluminum or an alloy of aluminum.

In order to further improve the high-temperature storage characteristics of the lithium-ion secondary battery, a portion in contact with the electrolyte solution among portions electrically coupled with the positive electrode current collector is also preferably formed from a valve metal or an alloy thereof. In particular, the external case of the battery and a portion that is electrically coupled with the positive electrode current collector and is in contact with the non-aqueous electrolyte solution among components accommodated in the external case of the battery, such as leads and a safety valve, are preferably formed from a valve metal or an alloy thereof. Stainless steel coated with a valve metal or an alloy thereof may also be used.

The positive electrode may be produced by the aforementioned method. An example of the production method is a method in which the positive electrode active material is mixed with the aforementioned binder, thickening agent, conductive material, solvent, and other components to form a slurry-like positive electrode mixture, and then this mixture is applied to a positive electrode current collector, dried, and pressed so as to be densified.

The structure of the negative electrode is as described above.

The invention may also relate to an electric double-layer capacitor including a positive electrode, a negative electrode, and the aforementioned electrolyte solution.

At least one selected from the positive electrode and the negative electrode is a polarizable electrode in the electric double-layer capacitor of the invention. Examples of the polarizable electrode and a non-polarizable electrode include the following electrodes specifically disclosed in JP H09-7896 A.

The polarizable electrode mainly containing activated carbon to be used in the invention preferably contains inactivated carbon having a large specific surface area and a conductive material, such as carbon black, providing electronic conductivity. The polarizable electrode may be formed by a variety of methods. For example, a polarizable electrode including activated carbon and carbon black can be produced by mixing activated carbon powder, carbon black, and phenolic resin, press-molding the mixture, and then sintering and activating the mixture in an inert gas atmosphere and water vapor atmosphere. Preferably, this polarizable electrode is bonded to a current collector using a conductive adhesive, for example.

Alternatively, a polarizable electrode can also be formed by kneading activated carbon powder, carbon black, and a binder in the presence of an alcohol, forming the mixture into a sheet, and then drying the sheet. The binder to be used may be polytetrafluoroethylene, for example. Alternatively, a polarizable electrode integrated with a current collector can be produced by mixing activated carbon powder, carbon black, a binder, and a solvent to form slurry, applying this slurry to metal foil of a current collector, and then drying the slurry.

The electric double-layer capacitor may have polarizable electrodes mainly containing activated carbon as the respective electrodes. Still, the electric double-layer capacitor may have a structure in which a non-polarizable electrode is used on one side. Examples of such a structure include a structure in which a positive electrode mainly containing an electrode active material such as a metal oxide is combined with a polarizable negative electrode mainly containing activated carbon; and a structure in which a negative electrode mainly containing a carbon material that can reversibly occlude and release lithium ions or a negative electrode of lithium metal or lithium alloy is combined with a polarizable positive electrode mainly containing activated carbon.

In place of or in combination with activated carbon, any carbonaceous material may be used, such as carbon black, graphite, expanded graphite, porous carbon, carbon nanotube, carbon nanohorn, and Ketjenblack.

The non-polarizable electrode is preferably an electrode mainly containing a carbon material that can reversibly occlude and release lithium ions, with this carbon material made to occlude lithium ions in advance. In this case, the electrolyte used is a lithium salt. The electric double-layer capacitor having such a structure can achieve a much higher withstand voltage exceeding 4 V.

The solvent used in preparation of the slurry in production of electrodes is preferably one that dissolves a binder. In accordance with the type of a binder, the solvent is appropriately selected from N-methylpyrrolidone, dimethyl formamide, toluene, xylene, isophorone, methyl ethyl ketone, ethyl acetate, methyl acetate, dimethyl phthalate, ethanol, methanol, butanol, and water.

Examples of the activated carbon used for the polarizable electrode include phenol resin-type activated carbon, coconut shell-type activated carbon, and petroleum coke-type activated carbon. In order to achieve a large capacity, petroleum coke-type activated carbon or phenol resin-type activated carbon is preferably used. Examples of methods of activating the activated carbon include steam activation and molten KOH activation. In order to achieve a larger capacity, activated carbon prepared by molten KOH activation is preferably used.

Preferred examples of the conductive agent used for the polarizable electrode include carbon black, Ketjenblack, acetylene black, natural graphite, artificial graphite, metal fiber, conductive titanium oxide, and ruthenium oxide. In order to achieve good conductivity (i.e., low internal resistance), and because too large an amount thereof may lead to a decreased capacity of the product, the amount of the conductive agent such as carbon black used for the polarizable electrode is preferably 1 to 50% by mass in the sum of the amounts of the activated carbon and the conductive agent.

In order to provide an electric double-layer capacitor having a large capacity and low internal resistance, the activated carbon used for the polarizable electrode preferably has an average particle size of 20 μm or smaller and a specific surface area of 1500 to 3000 $m^2/g$. Preferred examples of the carbon material for providing an electrode mainly containing a carbon material that can reversibly occlude and release lithium ions include natural graphite, artificial graphite, graphitized mesocarbon microsphere, graphitized whisker, vapor-grown carbon fiber, sintered furfuryl alcohol resin, and sintered novolak resin.

The current collector may be any chemically and electrochemically corrosion-resistant one. Preferred examples of the current collector used for the polarizable electrode mainly containing activated carbon include stainless steel, aluminum, titanium, and tantalum. Particularly preferred materials in terms of the characteristics and cost of the resulting electric double-layer capacitor are stainless steel and aluminum. Preferred examples of the current collector used for the electrode mainly containing a carbon material that can reversibly occlude and release lithium ions include stainless steel, copper, and nickel.

Examples of methods of allowing the carbon material that can reversibly occlude and release lithium ions to occlude lithium ions in advance include: (1) a method of mixing powdery lithium to a carbon material that can reversibly occlude and release lithium ions; (2) a method of placing lithium foil on an electrode including a carbon material that can reversibly occlude and release lithium ions and a binder so as to bring the lithium foil to be in electrical contact with the electrode, immersing this electrode in an electrolyte solution containing a lithium salt dissolved therein so as to ionize the lithium, and allowing the carbon material to take in the lithium ions; and (3) a method of placing an electrode including a carbon material that can reversibly occlude and release lithium ions and a binder on the minus side and placing a lithium metal on the plus side, immersing the electrodes in a non-aqueous electrolyte solution containing a lithium salt as an electrolyte, and supplying a current so that the carbon material is allowed to electrochemically take in the ionized lithium.

Examples of known electric double-layer capacitors include wound electric double-layer capacitors, laminated electric double-layer capacitors, and coin-type electric double-layer capacitors. The electric double-layer capacitor of the invention may also be any of these types.

For example, a wound electric double-layer capacitor may be assembled as follows. A positive electrode and a negative electrode each of which includes a laminate (electrode) of a current collector and an electrode layer are wound with a separator in between to provide a wound element. This wound element is put into a case made of aluminum, for example. The case is filled with an electrolyte solution, preferably a non-aqueous electrolyte solution, and then sealed with a rubber sealant.

A separator formed from a conventionally known material and having a conventionally known structure may be used also in the invention. Examples thereof include polyethylene porous membranes and nonwoven fabric of polypropylene fiber, glass fiber, or cellulose fiber.

In accordance with any known method, the electric double-layer capacitor may be prepared in the form of a laminated electric double-layer capacitor in which sheet-like positive and negative electrodes are stacked with an electrolyte solution and a separator in between or a coin-type electric double-layer capacitor in which positive and negative electrodes are fixed in a coin shape by a gasket with an electrolyte solution and a separator in between.

The electrolyte solution of the invention is useful as an electrolyte solution for large-size lithium-ion secondary batteries for hybrid vehicles or distributed generation, and for electric double-layer capacitors.

EXAMPLES

The invention is described with reference to examples, but the examples are not intended to limit the invention.

Synthesis Example 1 (Method of Synthesizing Compound (1a))

A 500-ml autoclave was charged with hydroxyacetone (70 g), pyridine (15 ml), and methylene chloride (40 ml). The components were cooled down to −100° C. with liquid nitrogen, and carbonyl fluoride (65 g) was introduced thereinto through a cylinder. The temperature was increased up to room temperature, and the components were heated at a temperature inside the container of 70° C. for 22 hours, whereby a black liquid was obtained. The resulting black liquid was mixed with methylene chloride and water. The mixture was then subjected to liquid separation, whereby the target product (compound (1a)) was obtained.

Synthesis Example 2 (Method of Synthesizing Compound (1b))

THF (1.7 g) was added to trifluoromethyl ethylene carbonate (100 mg), and the components were stirred at −78° C. Then, potassium t-butoxide (73.3 mg) and iodomethane (0.05 g) were added thereto and the components were stirred for 2 hours. The mixture was quenched with ice water. The reaction solution was roughly purified, and the resulting roughly purified product was purified by column chromatography. Thereby, 77.5 mg of the target product (compound (1b)) was obtained.

The following compounds (1c) to (1f) can be produced by known methods.

Examples 1 to 23 and Comparative Examples 1 to 7 (Preparation of Electrolyte Solution)

The components were mixed in accordance with the composition shown in one of Tables 1 to 3. $LiPF_6$ was added thereto so as to have a concentration of 1.0 mol/L, whereby a non-aqueous electrolyte solution was obtained.

The components shown in Tables 1 to 3 were as follows.

(Compound (1) group)

[Chem. 69]

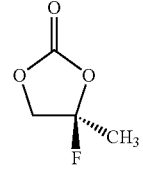

(1a)

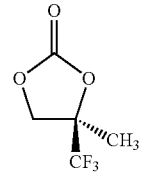

(1b)

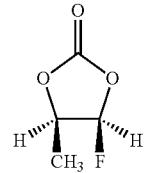

(1c)

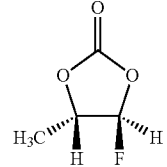

(1d)

-continued

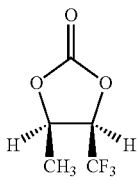

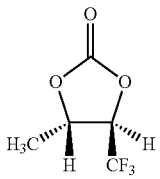

(Compound (2) group)

[Chem. 70]

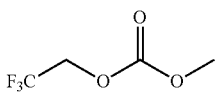

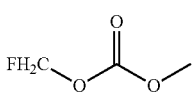

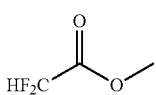

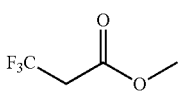

(Other components)

[Chem. 71]

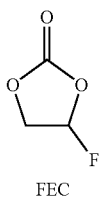
FEC

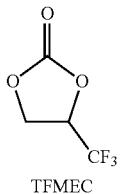
TFMEC

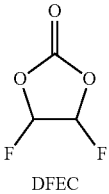
DFEC

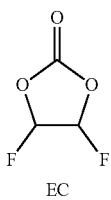
EC

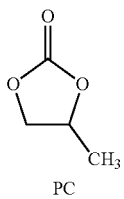
PC

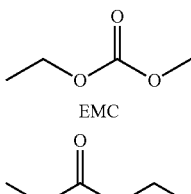
EMC　　DMC

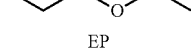
EP (Production of Aluminum Laminate-Type Lithium-Ion Secondary Battery)
(Production of Positive Electrode)

$LiNi_{0.5}Mn_{1.5}O_4$ serving as a positive electrode active material, acetylene black serving as a conductive material, and a dispersion of polyvinylidene fluoride (PVdF) in N-methyl-2-pyrrolidone serving as a binder were mixed to give slurry. Thereby, positive electrode mixture slurry was prepared. The positive electrode active material, the conductive material, and the binder had a solid content ratio of 93/2/5 (by mass %). This slurry was applied to one surface of 15-μm aluminum foil and dried. The workpiece was then roll-pressed using a press and cut out into a shape including an active material layer having a width of 50 mm and a length of 30 mm and an uncoated portion having a width of 5 mm and a length of 9 mm. Thereby, a positive electrode was produced.

(Production of Negative Electrode)

A carbonaceous material in an amount of 97 parts by mass was mixed with 1 part by mass of an aqueous dispersion of sodium carboxymethyl cellulose (concentration of sodium carboxymethyl cellulose: 1.5% by mass) and 1.5 parts by mass of an aqueous dispersion of styrene-butadiene rubber (concentration of styrene-butadiene rubber: 50% by mass) serving as a thickening agent and a binder. The components were mixed using a disperser to provide slurry. The resulting slurry was applied to 10-μm-thick copper foil and dried. The workpiece was rolled using a press and cut out into a shape including an active material layer having a width of 52 mm and a length of 32 mm and an uncoated portion having a width of 5 mm and a length of 9 mm. Thereby, a negative electrode was produced.

(Production of Aluminum Laminate Cell)

The positive electrode was placed to face the negative electrode with a 20-μm-thick porous polyethylene film (separator) in between. The non-aqueous electrolyte solution obtained above was poured into the workpiece and made to sufficiently permeate into the components such as the separator. The workpiece was then sealed, pre-charged, and aged, whereby a lithium-ion secondary battery was produced.

(Measurement of Battery Characteristics)

For the lithium-ion secondary battery, the high-temperature cycle characteristics, the amount of gas, and the IV resistance were examined as follows.

(Measurement of Battery Characteristics)
(Cycle Capacity Retention)

The secondary battery produced above in the state of being sandwiched and pressurized between plates was subjected to constant current-constant voltage charge (hereinafter, referred to as CC/CV charge) (0.1 C cut off) to 4.9 V at a current corresponding to 2 C at 60° C. Then, the battery was discharged to 3 V at a constant current of 1 C. This process was counted as one cycle. The initial discharge capacity was determined from the discharge capacity of the third cycle. Here, 1 C means the current value required for discharging the reference capacity of a battery in an hour. For example, 0.2 C indicates a ⅕ current value thereof. The cycle was again repeated, and the discharge capacity after 300 cycles was defined as the capacity after cycles. The ratio of the discharge capacity after 300 cycles to the initial discharge capacity was determined, which was regarded as the cycle capacity retention (%).

(Discharge capacity after 300 cycles)/(initial discharge capacity)×100=cycle capacity retention (%)

(Amount of Gas)

The volume of the lithium-ion secondary battery produced and the volume of the lithium-ion secondary battery after 300 cycles were measured. The amount of gas generated (ml) was calculated by the following formula.

(Volume after 300 cycles)−(Initial volume)=Amount of gas generated (ml)

(Evaluation of IV Resistance)

The battery after the evaluation of initial discharge capacity was charged at 25° C. and a constant current of 0.2 C up to half the initial discharge capacity. The battery was left at 25° C. and discharged at 2.0 C, and the voltage at the 10th second was measured. The resistance was calculated from the voltage drop in discharge, which was taken as the IV resistance.

TABLE 1

|  |  |  | Example 1 | Example 2 | Example 3 | Example 4 | Example 5 |
|---|---|---|---|---|---|---|---|
| Composition of electrolyte solution |  | Compound (1) Type Proportion (vol %) | 1a 40 | 1b 40 | 1c 40 | 1d 40 | 1e 40 |
|  |  | Compound (2) Type Proportion (vol %) | 2a 60 | 2a 60 | 2a 60 | 2a 60 | 2a 60 |
|  |  | Other components Type Proportion (vol %) | — | — | — | — | — |
| Battery characteristics | After storage of electrolyte solution | Cycle capacity retention (%) | 85 | 88 | 83 | 84 | 85 |
|  |  | IV resistance (Ω) | 2.8 | 3.1 | 2.9 | 2.8 | 3.3 |
|  |  | Amount of gas (ml) | 3.4 | 3.2 | 3.7 | 3.6 | 3.4 |
|  |  |  | Example 6 | Example 7 | Example 8 | Example 9 | Example 10 |
| Composition of electrolyte solution |  | Compound (1) Type Proportion (vol %) | 1f 40 | 1b 15 | 1b 55 | 1b 65 | 1a 40 |
|  |  | Compound (2) Type Proportion (vol %) | 2a 60 | 2a 85 | 2a 45 | 2a 35 | 2a 60 |
|  |  | Other components Type Proportion (vol %) | — | — | — | — | — |
| Battery characteristics | After storage of electrolyte solution | Cycle capacity retention (%) | 86 | 85 | 84 | 80 | 82 |
|  |  | IV resistance (Ω) | 3.2 | 3.2 | 3.2 | 3.5 | 2.7 |
|  |  | Amount of gas (ml) | 3.4 | 3.4 | 3.3 | 3.3 | 3.5 |

TABLE 2

|  |  |  | Example 11 | Example 12 | Example 13 | Example 14 | Example 15 |
|---|---|---|---|---|---|---|---|
| Composition of electrolyte solution |  | Compound (1) Type Proportion (vol %) | 1a 40 | 1a 40 | 1a 20 1b 20 | 1a 40 | 1b 30 |
|  |  | Compound (2) Type Proportion (vol %) | 2c 60 | 2d 60 | 2a 60 | 2a 30 2c 30 | 2a 60 |
|  |  | Other components Type Proportion (vol %) | — | — | — | — | FEC 10 |
| Battery characteristics | After storage of electrolyte solution | Cycle capacity retention (%) | 79 | 77 | 86 | 81 | 84 |
|  |  | IV resistance (Ω) | 2.5 | 2.7 | 3.0 | 3.0 | 3.0 |
|  |  | Amount of gas (ml) | 3.6 | 3.7 | 3.3 | 3.5 | 3.6 |
|  |  |  | Example 16 | Example 17 | Example 18 | Example 19 | Example 20 |
| Composition of electrolyte solution |  | Compound (1) Type Proportion (vol %) | 1b 30 | 1b 30 | 1b 30 | 1b 30 | 1b 15 |
|  |  | Compound (2) Type Proportion (vol %) | 2b 60 | 2c 60 | 2d 60 | 2d 60 | 2c 50 |

TABLE 2-continued

|  |  |  | TFMEC | DFEC | EC | PC | EMC |
|---|---|---|---|---|---|---|---|
|  |  | Other components Type Proportion (vol %) | 10 | 10 | 10 | 10 | 35 |
| Battery characteristics | After storage of electrolyte solution | Cycle capacity retention (%) | 86 | 85 | 82 | 81 | 84 |
|  |  | IV resistance (Ω) | 3.2 | 3.1 | 3.2 | 3.0 | 3.1 |
|  |  | Amount of gas (ml) | 3.3 | 3.0 | 3.3 | 3.2 | 3.5 |

TABLE 3

|  |  |  | Example 21 | Example 22 | Example 23 | Comparative Example 1 | Comparative Example 2 |
|---|---|---|---|---|---|---|---|
| Composition of electrolyte solution |  | Compound (1) | 1b | 1b | 1f | 1a | 1b |
|  |  | Type Proportion (vol %) | 15 | 15 | 0.5 | 40 | 40 |
|  |  | Compound (2) | 2c | 2c | 2a | — | — |
|  |  | Type Proportion (vol %) | 50 | 50 | 70 |  |  |
|  |  | Other components | DMC | EP | TFEMC | EMC | EMC |
|  |  | Type Proportion (vol %) | 35 | 35 | 29.5 | 60 | 60 |
| Battery characteristics | After storage of electrolyte solution | Cycle capacity retention (%) | 85 | 83 | 81 | 58 | 63 |
|  |  | IV resistance (Ω) | 3.0 | 3.1 | 3.5 | 6.6 | 6.9 |
|  |  | Amount of gas (ml) | 3.6 | 3.5 | 3.5 | 9.1 | 8.4 |

|  |  |  | Comparative Example 3 | Comparative Example 4 | Comparative Example 5 | Comparative Example 6 | Comparative Example 7 |
|---|---|---|---|---|---|---|---|
| Composition of electrolyte solution |  | Compound (1) | — | — | — | — | — |
|  |  | Type Proportion (vol %) |  |  |  |  |  |
|  |  | Compound (2) | 2c | 2a | — | 2c | 2c |
|  |  | Type Proportion (vol %) | 90 | 60 |  | 70 | 70 |
|  |  | Other components | FEC | FEC | FEC | TFMEC | DFEC |
|  |  | Type Proportion (vol %) | 10 | 40 | 40 EMC 60 | 30 | 30 |
| Battery characteristics | After storage of electrolyte solution | Cycle capacity retention (%) | 57 | 66 | 55 | 67 | 61 |
|  |  | IV resistance (Ω) | 4.1 | 5.4 | 5.1 | 8.1 | 8.0 |
|  |  | Amount of gas (ml) | 5.1 | 12.1 | 14.1 | 8.1 | 7.7 |

What is claimed is:

1. An electrolyte solution comprising a solvent, the solvent containing:
a compound (1a) represented by the following formula (1a); and

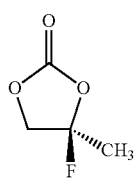

(1a)

a compound (2) represented by the following formula (2):

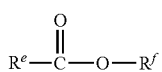

(2)

wherein $R^e$ is a C1-C5 linear or branched alkyl group optionally containing an ether bond; $R^f$ is a C1-C5 linear or branched alkyl group optionally containing an ether bond; and at least one of $R^e$ or $R^f$ contains a fluorine atom.

2. The electrolyte solution according to claim 1, wherein the compound (1a) is contained in an amount of 0.001 to 99.999% by volume relative to the solvent.

3. The electrolyte solution according to claim 1, wherein the compound (2) is contained in an amount of 0.001 to 99.999% by volume relative to the solvent.

4. The electrolyte solution according to claim 1, further comprising an electrolyte salt.

5. An electrochemical device comprising the electrolyte solution according to claim 1.

6. A lithium-ion secondary battery comprising the electrolyte solution according to claim 1.

7. A module comprising the electrochemical device according to claim 5.

8. A module comprising the lithium-ion secondary battery according to claim 6.

* * * * *